(12) United States Patent
Gils

(10) Patent No.: US 9,012,729 B2
(45) Date of Patent: Apr. 21, 2015

(54) PROCESS OF PRODUCING MALE STERILE MONOCOTYLEDONOUS PLANTS

(75) Inventor: Mario Gils, Quedlinburg (DE)

(73) Assignee: Nordsaat Saatzuchtgesellschaft mbH, Boehnshausen (DE)

(*) Notice: Subject to any disclaimer, the term of this patent is extended or adjusted under 35 U.S.C. 154(b) by 1169 days.

(21) Appl. No.: 12/996,364

(22) PCT Filed: Jun. 3, 2009

(86) PCT No.: PCT/EP2009/056825
§ 371 (c)(1),
(2), (4) Date: Mar. 23, 2011

(87) PCT Pub. No.: WO2009/147179
PCT Pub. Date: Dec. 10, 2009

(65) Prior Publication Data
US 2011/0167513 A1 Jul. 7, 2011

(30) Foreign Application Priority Data

Jun. 3, 2008 (EP) ..................................... 08157508

(51) Int. Cl.
C12N 15/10 (2006.01)
C12N 15/00 (2006.01)
C12N 15/82 (2006.01)
C12N 15/62 (2006.01)

(52) U.S. Cl.
CPC ............ *C12N 15/8213* (2013.01); *C12N 15/62* (2013.01); *C12N 15/8216* (2013.01); *C12N 15/8265* (2013.01); *C12N 15/8289* (2013.01)

(58) Field of Classification Search
None
See application file for complete search history.

(56) References Cited

FOREIGN PATENT DOCUMENTS

WO  WO 00/71701  11/2000
WO  WO 03/102197  12/2003

OTHER PUBLICATIONS

Plant Biotechnology Journal, (2008), 6, pp. 226-235.*
J. Biol. Chem., (1997), 272, pp. 15587-15590.*
J. Biol. Chem., (2002), 277, pp. 7790-7798.*
AM888351, "Transformation Vector pICH13688," Mar. 18, 2008 [online] [retrieved Jul. 23, 2012]. Retrieved from: NCBI Genbank database.
AP008208.2, "*Oryza sativa* Japonica Group DNA, chromosome 2, complete sequence, cultivar: Nipponbare," Aug. 7, 2009 [online] [retrieved on Jul. 23, 2012]. Retrieved from: NCBI Genbank database.
Bernd-Souza, RB, et al., "A rat pancreatic ribonuclease fused to a late cotton pollen promoter severely reduces pollen viability in tobacco plants," Genetics and Molecular Biology, 2000, 23(2): 435-443.
Burgess, D, et al., "A novel, two-component system for cell lethality and its use in engineering nuclear male-sterility in plants," Plant Journal, Jan. 1, 2002, 31(1): 113-125.
Chen, L, et al., "Herbicide resistance from a divided EPSPS protein: the split *Synechocystis* DnaE intein as an in vivo affinity domain," Gene, 2001, 263: 39-48.
Chin, HG, et al., "Protein trans-splicing in transgenic plant chloroplast: Reconstruction of herbicide resistance from split genes," PNAS, Apr. 15, 2003, 100(8): 4510-4515.
Cho, HJ, et al., "Production of Transgenic Male Sterile Tobacco Plants with the cDNA Encoding a Ribosome Inactivating Protein in *Dianthus sinensis* L.," Mol Cells, 2001, 11(3): 326-333.
Chong, S, and Xu, MQ, "Protein Splicing of the *Saccharomyces cervisiae* VMA Intein without the Endonuclease Motifs," J Biol Chem, Jun. 20, 1997, 272(25): 15567-15590.
De Block, M, et al., "The development of a nuclear male sterility system in wheat. Expression of the *Barnase* gene under the control of tapetum specific promoters," Theor Appl Genet, 1997, 95:125-131.
Denis, M, et al., "Expression of Engineered Nuclear Male Sterility in *Brassica napus* Genetics, Morphology, Cytology, and Sensitivity to Temperature," Plant Physiol, 1993, 101: 1295-1304.
Evans, T, et al. "Protein splicing elements and plants: From transgene containment to protein purification," Annual Review of Plant Biology, 2005, 56: 375-392.
Gils, M., "Research Group: Hyprid Wheat," in: Leibniz-Institut Für Pflanzengenetik und Kulturpflanzenforschung, *Annual Report* 2007, (Leibniz Gemeinschaft, Gatersleben, 2008), pp. 116-117, 166.
Gils, M, et al. "The 'Split Gene Approach' for plants: Divided genes for maximum yield. GABI-FUTURE-Bridge Project 'Hybrid Wheat': Estaplishment of a novel transgenic system for hybrid wheat seed production," Genomxpress, Dec. 2007, vol. 7, No. 4, pp. 7-10.
Gils, M, et al. "A novel hybrid seed system for plants," Plant Biotechnology Journal, Apr. 2008, 6(3) :226-235.
Jones, J, "Effective vectors for transformation, expression of heterologous genes, and assaying transposon excision in transgenic plants," Transgenic Research, 1992, 1: 285-297.
Kempe, K, et al., "Intein-mediated protein assembly in transgenic wheat: production of active barnase and acetolactate synthase from split genes," Plant Biotechnology Journal, Apr. 2009, 7: 283-297.
Kuvshinov, V, et al., "Molecular control of transgene escape from genetically modified plants," Plant Science, Jan. 1, 2001, 160: 517-522.
Mariani, C, et al., "Induction of male sterility in plants by a chimaeric ribonuclease gene," Nature, Oct. 25, 1990, 347: 737-741.
Mariani, C, et al., "A chimaeric ribonuclease-inhibitor gene restores fertility to male sterile plant," Nature, Jun. 4, 1992, 357: 384-387.
McElroy, D, et al., "Isolation of an Efficient Actin Promoter for Use in Rice Transformation," Plant Cell, Feb. 1990, 2: 163-171.
Perler, F, "Protein Splicing of Inteins and Hedgehog Autoproteolysis: Stucture, Function, and Evolution," Cell, Jan. 9, 1998, 92:1-4.
Perler, F, "InBase: the Intein Database," Nucleic Acids Research, 2002, 30(1): 383-384.
Rubtsova, M, "Expression of active *Streptomyces* phage phiC31 integrase in transgenic wheat plants," Plant Cell Rep, Dec. 2008, 27(12) 1821-1831.

(Continued)

Primary Examiner — Brent T Page
Assistant Examiner — Jared Shapiro
(74) Attorney, Agent, or Firm — Hahn Loeser & Parks LLP

(57) ABSTRACT

The present invention relates to a process of producing male sterile monocotyledonous plants by introducing into said plants fragments of a nucleotide sequence coding for a protein which provides for male sterility and reconstituting the complete protein which provides for male sterility by intein-mediated trans-splicing.

4 Claims, 19 Drawing Sheets

(56) References Cited

OTHER PUBLICATIONS

Saleh, L, and Perler, F, "Protein Splicing *In Cis* and *In Trans*," Chemical Record, 2006, 6: 183-193.

Southworth, M, et al., "Control of protein splicing by intein fragment reassembly," EMBO Journal, 1998, 17(4) 918-926.

Sun, L, et al., "Protein trans-splicing to produce herbicide-resistant acetolactate synthase," Applied and Environmental Microbiology, Mar. 1, 2001, 67(3): 1025-1029.

Tan, S, et al., "Imidazolinone-tolerant crops: history, current status and future," Pest Management Science, Jan. 1, 2005, 61(3): 246-257.

Tsuchiya, T, et al., "Tapetum-Specific Expression of the Gene for an Endo-β-1,3-glucanase Causes Male Sterility in Transgenic Tobacco," Plant Cell Physiol, 1995, 36(3): 487-494.

Wu H, et al., "Protein *trans*-splicing by a split intein encoded in a split DnaE gene of *Synechocystis* sp. PCC6803," Proc. Natl. Acad. Sci. USA, Aug. 1998, 95: 9226-9231.

International Search Report, in related application No. PCT/EP2009/056825, published Feb. 18, 2010.

\* cited by examiner b)                 pICH24581 c)

d) pICH27371 e) pICH25881 c)

d)

SEQUENCE LISTING

```
<160> NUMBER OF SEQ ID NOS: 71

<210> SEQ ID NO 1
<211> LENGTH: 447
<212> TYPE: DNA
<213> ORGANISM: Bacillus amyloliquefaciens
<220> FEATURE:
<221> NAME/KEY: misc_feature
<222> LOCATION: (1)..(447)
<223> OTHER INFORMATION: native sequence of the barnase enzyme from
      Bacillus amyloliquefaciens

<400> SEQUENCE: 1
atgaaaaaac gattatcgtg gatttccgtt tgtttactgg tgcttgtctc cgcggcgggg      60
atgctgtttt caacagctgc caaaacggaa acatcttctc acaaggcaca cacagaagca     120
caggttatca acacgtttga cggggttgcg gattatcttc agacatatca taagctacct     180
gataattaca ttacaaaatc agaagcacaa gccctcggct gggtggcatc aaaagggaac     240
cttgcagacg tcgctccggg gaaaagcatc ggcggagaca tcttctcaaa cagggaaggc     300
aaactcccgg gcaaaagcgg acgaacatgg cgtgaagcgg atattaacta tacatcaggc     360
ttcagaaatt cagaccggat tctttactca agcgactggc tgatttacaa aacaacggac     420
cattatcaga cctttacaaa aatcaga                                         447

<210> SEQ ID NO 2
<211> LENGTH: 149
<212> TYPE: PRT
<213> ORGANISM: Bacillus amyloliquefaciens
<220> FEATURE:
<221> NAME/KEY: SIGNAL
<222> LOCATION: (1)..(39)
<223> OTHER INFORMATION: leader peptide of the mature protein
<220> FEATURE:
<221> NAME/KEY: MISC_FEATURE
<222> LOCATION: (1)..(149)
<223> OTHER INFORMATION: native sequence of the barnase enzyme from
      Bacillus amyloliquefaciens

<400> SEQUENCE: 2
```

Met Lys Lys Arg Leu Ser Trp Ile Ser Val Cys Leu Leu Val Leu Val
1               5                   10                  15

Ser Ala Ala Gly Met Leu Phe Ser Thr Ala Ala Lys Thr Glu Thr Ser
                20                  25                  30

Ser His Lys Ala His Thr Glu Ala Gln Val Ile Asn Thr Phe Asp Gly
            35                  40                  45

Val Ala Asp Tyr Leu Gln Thr Tyr His Lys Leu Pro Asp Asn Tyr Ile
        50                  55                  60

Thr Lys Ser Glu Ala Gln Ala Leu Gly Trp Val Ala Ser Lys Gly Asn
65                  70                  75                  80

Leu Ala Asp Val Ala Pro Gly Lys Ser Ile Gly Gly Asp Ile Phe Ser
                85                  90                  95

Asn Arg Glu Gly Lys Leu Pro Gly Lys Ser Gly Arg Thr Trp Arg Glu
                100                 105                 110

Ala Asp Ile Asn Tyr Thr Ser Gly Phe Arg Asn Ser Asp Arg Ile Leu
            115                 120                 125

Tyr Ser Ser Asp Trp Leu Ile Tyr Lys Thr Thr Asp His Tyr Gln Thr
    130                 135                 140

Phe Thr Lys Ile Arg
145

<210> SEQ ID NO 3
<211> LENGTH: 108
<212> TYPE: DNA
<213> ORGANISM: Artificial
<220> FEATURE:
<221> NAME/KEY: misc_feature
<222> LOCATION: (1)..(108)
<223> OTHER INFORMATION: non-optimized N-terminus of the barnase
      sequence used in vector pICH13688

<400> SEQUENCE: 3
atggcacagg ttatcaacac gtttgacggg gttgcggatt atcttcagac atatcataag    60
ctacctgata attacattac aaaatcagaa gcacaagccc tcggctgg              108

<210> SEQ ID NO 4
<211> LENGTH: 36
<212> TYPE: PRT
<213> ORGANISM: Artificial
<220> FEATURE:
<221> NAME/KEY: MISC_FEATURE
<222> LOCATION: (1)..(36)
<223> OTHER INFORMATION: non-optimized N-terminus of the barnase
      sequence used in vector pICH13688

<400> SEQUENCE: 4

Met Ala Gln Val Ile Asn Thr Phe Asp Gly Val Ala Asp Tyr Leu Gln
1               5                   10                  15

Thr Tyr His Lys Leu Pro Asp Asn Tyr Ile Thr Lys Ser Glu Ala Gln
                20                  25                  30

Ala Leu Gly Trp
        35

<210> SEQ ID NO 5
<211> LENGTH: 225
<212> TYPE: DNA
<213> ORGANISM: Artificial
<220> FEATURE:
<221> NAME/KEY: misc_feature
<222> LOCATION: (1)..(225)
<223> OTHER INFORMATION: non-optimized C-terminus of the barnase -continued sequence used in vector pICH13688

<400> SEQUENCE: 5

```
gtcgcatcaa aagggaacct tgcagacgtc gctccgggga aaagcatcgg cggagacatc        60
ttctcaaaca gggaaggcaa actcccgggc aaaagcggac gaacatggcg tgaagcggat       120
attaactata catcaggctt cagaaattca gaccggattc tttactcaag cgactggctg       180
atttacaaaa caacggacca ttatcagacc tttacaaaaa tcaga                      225
```

<210> SEQ ID NO 6
<211> LENGTH: 75
<212> TYPE: PRT
<213> ORGANISM: Artificial
<220> FEATURE:
<221> NAME/KEY: MISC_FEATURE
<222> LOCATION: (1)..(75)
<223> OTHER INFORMATION: non-optimized C-terminus of the barnase
      sequence used in vector pICH13688

<400> SEQUENCE: 6

```
Val Ala Ser Lys Gly Asn Leu Ala Asp Val Ala Pro Gly Lys Ser Ile
1               5                   10                  15

Gly Gly Asp Ile Phe Ser Asn Arg Glu Gly Lys Leu Pro Gly Lys Ser
            20                  25                  30

Gly Arg Thr Trp Arg Glu Ala Asp Ile Asn Tyr Thr Ser Gly Phe Arg
        35                  40                  45

Asn Ser Asp Arg Ile Leu Tyr Ser Ser Asp Trp Leu Ile Tyr Lys Thr
    50                  55                  60

Thr Asp His Tyr Gln Thr Phe Thr Lys Ile Arg
65                  70                  75
```

<210> SEQ ID NO 7
<211> LENGTH: 1287
<212> TYPE: DNA
<213> ORGANISM: Synechocystis sp.
<220> FEATURE:
<221> NAME/KEY: gene
<222> LOCATION: (1)..(1287)

<400> SEQUENCE: 7

```
tgcatcagtg gagatagttt gatcagcttg gcgagcacag gaaaaagagt ttctattaaa        60
gatttgttag atgaaaaaga ttttgaaata tgggcaatta tgaacagac gatgaagcta       120 gaatcagcta agttagtcg tgtattttgt actggcaaaa agctagttta tattttaaaa       180
actcgactag gtagaactat caaggcaaca gcaaatcata gattttaac tattgatggt       240 tggaaaagat tagatgagct atcttttaaaa gagcatattg ctctaccccg taaactagaa       300
agctcctctt tacaattaat gagtgatgag gaactaggat tactagggca tctaattggt       360
gatggctgta ctttaccctcg ccatgctatt caatatacaa gcaataaaat agaattagct       420
gaaaaggtag tcgaattagc aaaagcagtt tttggcgacc aaattaatcc tcgtatcagc       480
caagaaaggc aatggtacca agtttatatc cctgctagtt atcggctaac ccataacaaa       540
aaaaatccga ttacaaaatg gctagagaat ttagacgtat tcggactgcg ttcctacgaa       600
aaatttgttc ctaatcaagt ttttgaacaa ccacagaggg cgatcgccat ttttctaaga       660
catttatgga gtacagatgg ttgcgtcaaa ttaatagtag aaaaatcatc tagaccggta       720
gcttattacg caactagtag cgagaagtta gcaaaggatg tacagtcgtt actcttgaaa       780
ttaggcatta acgcacgtct atcaaaaata agtcagaatg gcaaaggcag ggataactat       840
```

-continued

```
catgtaacca ttacagggca agctgattta caaatctttg ttgatcaaat tggcgctgtt    900
gacaaagaca acaggcaag tgttgaggaa attaaaaccc atatcgctca acatcaagca     960
aacactaaca gggatgtcat tccaaaacaa atttggaaga cctatgtgtt gccacaaatt   1020
caaataaaag ggataactac tcgcgacttg caaatgagac ttggtaatgc ctactgtggg   1080
acagctcttt ataaacataa tttgagtagg gaaagagcag caaaaatagc cactattacc   1140
caatcaccag aaatagaaaa gttgtctcag agtgatattt actgggactc catcgtttct   1200
attacggaga ctggagtcga agaggttttt gatttgactg tgccaggacc acataacttt   1260
gtcgccaatg acatcattgt ccataac                                       1287
```

<210> SEQ ID NO 8
<211> LENGTH: 429
<212> TYPE: PRT
<213> ORGANISM: Synechocystis sp.
<220> FEATURE:
<221> NAME/KEY: MISC_FEATURE
<222> LOCATION: (1)..(429)
<223> OTHER INFORMATION: complete amino acid sequence of DnaB from
     Synechocystis sp.

<400> SEQUENCE: 8

```
Cys Ile Ser Gly Asp Ser Leu Ile Ser Leu Ala Ser Thr Gly Lys Arg
1               5                   10                  15

Val Ser Ile Lys Asp Leu Leu Asp Glu Lys Asp Phe Glu Ile Trp Ala
            20                  25                  30

Ile Asn Glu Gln Thr Met Lys Leu Glu Ser Ala Lys Val Ser Arg Val
        35                  40                  45

Phe Cys Thr Gly Lys Lys Leu Val Tyr Ile Leu Lys Thr Arg Leu Gly
    50                  55                  60

Arg Thr Ile Lys Ala Thr Ala Asn His Arg Phe Leu Thr Ile Asp Gly
65                  70                  75                  80

Trp Lys Arg Leu Asp Glu Leu Ser Leu Lys Glu His Ile Ala Leu Pro
                85                  90                  95

Arg Lys Leu Glu Ser Ser Ser Leu Gln Leu Met Ser Asp Glu Glu Leu
            100                 105                 110

Gly Leu Leu Gly His Leu Ile Gly Asp Gly Cys Thr Leu Pro Arg His
        115                 120                 125

Ala Ile Gln Tyr Thr Ser Asn Lys Ile Glu Leu Ala Glu Lys Val Val
    130                 135                 140

Glu Leu Ala Lys Ala Val Phe Gly Asp Gln Ile Asn Pro Arg Ile Ser
145                 150                 155                 160

Gln Glu Arg Gln Trp Tyr Gln Val Tyr Ile Pro Ala Ser Tyr Arg Leu
                165                 170                 175

Thr His Asn Lys Lys Asn Pro Ile Thr Lys Trp Leu Glu Asn Leu Asp
            180                 185                 190

Val Phe Gly Leu Arg Ser Tyr Glu Lys Phe Val Pro Asn Gln Val Phe
        195                 200                 205

Glu Gln Pro Gln Arg Ala Ile Ala Ile Phe Leu Arg His Leu Trp Ser
    210                 215                 220

Thr Asp Gly Cys Val Lys Leu Ile Val Glu Lys Ser Ser Arg Pro Val
225                 230                 235                 240

Ala Tyr Tyr Ala Thr Ser Ser Glu Lys Leu Ala Lys Asp Val Gln Ser
                245                 250                 255

Leu Leu Leu Lys Leu Gly Ile Asn Ala Arg Leu Ser Lys Ile Ser Gln
            260                 265                 270
```

-continued

Asn Gly Lys Gly Arg Asp Asn Tyr His Val Thr Ile Thr Gly Gln Ala
        275                 280                 285

Asp Leu Gln Ile Phe Val Asp Gln Ile Gly Ala Val Asp Lys Asp Lys
    290                 295                 300

Gln Ala Ser Val Glu Glu Ile Lys Thr His Ile Ala Gln His Gln Ala
305                 310                 315                 320

Asn Thr Asn Arg Asp Val Ile Pro Lys Gln Ile Trp Lys Thr Tyr Val
            325                 330                 335

Leu Pro Gln Ile Gln Ile Lys Gly Ile Thr Thr Arg Asp Leu Gln Met
        340                 345                 350

Arg Leu Gly Asn Ala Tyr Cys Gly Thr Ala Leu Tyr Lys His Asn Leu
        355                 360                 365

Ser Arg Glu Arg Ala Ala Lys Ile Ala Thr Ile Thr Gln Ser Pro Glu
    370                 375                 380

Ile Glu Lys Leu Ser Gln Ser Asp Ile Tyr Trp Asp Ser Ile Val Ser
385                 390                 395                 400

Ile Thr Glu Thr Gly Val Glu Glu Val Phe Asp Leu Thr Val Pro Gly
            405                 410                 415

Pro His Asn Phe Val Ala Asn Asp Ile Ile Val His Asn
        420                 425

<210> SEQ ID NO 9
<211> LENGTH: 336
<212> TYPE: DNA
<213> ORGANISM: Artificial
<220> FEATURE:
<221> NAME/KEY: misc_feature
<222> LOCATION: (1)..(6)
<223> OTHER INFORMATION: sequence coding for the amino acids aspartate
      and valine; both have been inserted into vector pICH13688 as a
      result of the cloning strategies
<220> FEATURE:
<221> NAME/KEY: misc_feature
<222> LOCATION: (7)..(15)
<223> OTHER INFORMATION: dnaB intein exon sequence RES
<220> FEATURE:
<221> NAME/KEY: misc_feature
<222> LOCATION: (7)..(18)
<223> OTHER INFORMATION: dnaB intein exon sequence RESG
<220> FEATURE:
<221> NAME/KEY: misc_feature
<222> LOCATION: (19)..(336)
<223> OTHER INFORMATION: N-terminal part of the dnaB intein from
      Synechocystis sp.

<400> SEQUENCE: 9
gacgtcagag agagtggatg catcagtgga gatagtttga tcagcttggc gagcacagga      60
aaaagagttt ctattaaaga tttgttagat gaaaaagatt ttgaaatatg gcaattaat     120 gaacagacga tgaagctaga atcagctaaa gttagtcgtg tattttgtac tggcaaaaag    180 ctagttttata ttttaaaaac tcgactaggt agaactatca aggcaacagc aaatcataga   240
tttttaacta ttgatggttg gaaaagatta gatgagctat cttttaaaga gcatattgct    300
ctaccccgta aactagaaag ctcctctta caatta                               336

<210> SEQ ID NO 10
<211> LENGTH: 112
<212> TYPE: PRT
<213> ORGANISM: Artificial
<220> FEATURE:
<221> NAME/KEY: MISC_FEATURE
<222> LOCATION: (1)..(2)
<223> OTHER INFORMATION: insertion of the amino acids aspartate and valine as a result of the cloning strategies
<220> FEATURE:
<221> NAME/KEY: MISC_FEATURE
<222> LOCATION: (3)..(5)
<223> OTHER INFORMATION: DnaB intein exon sequence RES
<220> FEATURE:
<221> NAME/KEY: MISC_FEATURE
<222> LOCATION: (3)..(6)
<223> OTHER INFORMATION: DnaB intein exon sequence RESG
<220> FEATURE:
<221> NAME/KEY: MISC_FEATURE
<222> LOCATION: (7)..(112)
<223> OTHER INFORMATION: N-terminal part of DnaB intein from
     Synechocystis sp.

<400> SEQUENCE: 10

Asp Val Arg Glu Ser Gly Cys Ile Ser Gly Asp Ser Leu Ile Ser Leu
1               5                   10                  15

Ala Ser Thr Gly Lys Arg Val Ser Ile Lys Asp Leu Leu Asp Glu Lys
            20                  25                  30

Asp Phe Glu Ile Trp Ala Ile Asn Glu Gln Thr Met Lys Leu Glu Ser
        35                  40                  45

Ala Lys Val Ser Arg Val Phe Cys Thr Gly Lys Lys Leu Val Tyr Ile
    50                  55                  60

Leu Lys Thr Arg Leu Gly Arg Thr Ile Lys Ala Thr Ala Asn His Arg
65                  70                  75                  80

Phe Leu Thr Ile Asp Gly Trp Lys Arg Leu Asp Glu Leu Ser Leu Lys
                85                  90                  95

Glu His Ile Ala Leu Pro Arg Lys Leu Glu Ser Ser Ser Leu Gln Leu
            100                 105                 110

<210> SEQ ID NO 11
<211> LENGTH: 168
<212> TYPE: DNA
<213> ORGANISM: Artificial
<220> FEATURE:
<221> NAME/KEY: misc_feature
<222> LOCATION: (1)..(147)
<223> OTHER INFORMATION: C-terminal part of dnaB intein from
     Synechocystis sp.
<220> FEATURE:
<221> NAME/KEY: misc_feature
<222> LOCATION: (148)..(168)
<223> OTHER INFORMATION: dnaB exon sequence SEEQDHG

<400> SEQUENCE: 11
atgagcccag aaatagaaaa gttgtctcag agtgatattt actgggactc catcgtttct        60
attacggaga ctggagtcga agaggttttt gatttgactg tgccaggacc acataacttt       120
gtcgccaatg acatcattgt ccataacagt gaagagcaag accatggc                    168

<210> SEQ ID NO 12
<211> LENGTH: 56
<212> TYPE: PRT
<213> ORGANISM: Artificial
<220> FEATURE:
<221> NAME/KEY: MISC_FEATURE
<222> LOCATION: (1)..(49)
<223> OTHER INFORMATION: C-terminal part of DnaB intein from
     Synechocystis sp.
<220> FEATURE:
<221> NAME/KEY: MISC_FEATURE
<222> LOCATION: (50)..(56)
<223> OTHER INFORMATION: DnaB exon sequence

<400> SEQUENCE: 12

Met Ser Pro Glu Ile Glu Lys Leu Ser Gln Ser Asp Ile Tyr Trp Asp

```
                1               5                   10                  15
Ser Ile Val Ser Ile Thr Glu Thr Gly Val Glu Glu Val Phe Asp Leu
                        20                  25                  30

Thr Val Pro Gly Pro His Asn Phe Val Ala Asn Asp Ile Ile Val His
            35                  40                  45

Asn Ser Glu Glu Gln Asp His Gly
        50                  55
```

<210> SEQ ID NO 13
<211> LENGTH: 108
<212> TYPE: DNA
<213> ORGANISM: Artificial
<220> FEATURE:
<221> NAME/KEY: misc_feature
<222> LOCATION: (1)..(108)
<223> OTHER INFORMATION: codon-optimized N-terminus of the barnase
      sequence from Bacillus amyloliquefaciens

<400> SEQUENCE: 13

```
atggcccaag tgattaacac cttcgacggc gtggccgact acctccagac ctaccacaag    60
ctcccggaca actacatcac caagtccgag gcccaggccc tcggctgg                108
```

<210> SEQ ID NO 14
<211> LENGTH: 36
<212> TYPE: PRT
<213> ORGANISM: Artificial
<220> FEATURE:
<221> NAME/KEY: MISC_FEATURE
<222> LOCATION: (1)..(36)
<223> OTHER INFORMATION: codon-optimized N-terminus of the barnase
      sequence from Bacillus amyloliquefaciens

<400> SEQUENCE: 14

```
Met Ala Gln Val Ile Asn Thr Phe Asp Gly Val Ala Asp Tyr Leu Gln
1               5                   10                  15

Thr Tyr His Lys Leu Pro Asp Asn Tyr Ile Thr Lys Ser Glu Ala Gln
            20                  25                  30

Ala Leu Gly Trp
        35
```

<210> SEQ ID NO 15
<211> LENGTH: 12
<212> TYPE: DNA
<213> ORGANISM: Synechocystis sp.
<220> FEATURE:
<221> NAME/KEY: misc_feature
<222> LOCATION: (1)..(12)
<223> OTHER INFORMATION: dnaB extein part, N-terminal

<400> SEQUENCE: 15

```
agggagtccg gc                                                        12
```

<210> SEQ ID NO 16
<211> LENGTH: 4
<212> TYPE: PRT
<213> ORGANISM: Synechocystis sp.
<220> FEATURE:
<221> NAME/KEY: MISC_FEATURE
<222> LOCATION: (1)..(4)
<223> OTHER INFORMATION: DnaB extein part, N-terminal

<400> SEQUENCE: 16

```
Arg Glu Ser Gly
1
```

<210> SEQ ID NO 17
<211> LENGTH: 318
<212> TYPE: DNA
<213> ORGANISM: Synechocystis sp.
<220> FEATURE:
<221> NAME/KEY: misc_feature
<222> LOCATION: (1)..(318)
<223> OTHER INFORMATION: codon-optimized N-terminus of dnaB intein

<400> SEQUENCE: 17

```
tgcatctccg gcgactccct catctccctc gcctccaccg gcaagcgcgt gtccatcaag      60
gacctcctcg acgagaagga cttcgagatt tgggccatca acgagcagac catgaagctg     120
gagtccgcca aggtgtcccg cgtgttctgc accggcaaga agctcgtcta tatcctcaag     180
acccgcctcg gcaggaccat caaggccacc gccaaccacc gcttcctcac catcgacggc     240
tggaagcgcc tcgacgagct gtccctcaag gagcacatcg ccctcccgcg caagctcgaa     300
tcctcctccc tccagctc                                                   318
```

<210> SEQ ID NO 18
<211> LENGTH: 106
<212> TYPE: PRT
<213> ORGANISM: Synechocystis sp.
<220> FEATURE:
<221> NAME/KEY: MISC_FEATURE
<222> LOCATION: (1)..(106)
<223> OTHER INFORMATION: codon-optimized N-terminus of DnaB intein

<400> SEQUENCE: 18

```
Cys Ile Ser Gly Asp Ser Leu Ile Ser Leu Ala Ser Thr Gly Lys Arg
 1               5                  10                  15

Val Ser Ile Lys Asp Leu Leu Asp Glu Lys Asp Phe Glu Ile Trp Ala
            20                  25                  30

Ile Asn Glu Gln Thr Met Lys Leu Glu Ser Ala Lys Val Ser Arg Val
        35                  40                  45

Phe Cys Thr Gly Lys Lys Leu Val Tyr Ile Leu Lys Thr Arg Leu Gly
    50                  55                  60

Arg Thr Ile Lys Ala Thr Ala Asn His Arg Phe Leu Thr Ile Asp Gly
65                  70                  75                  80

Trp Lys Arg Leu Asp Glu Leu Ser Leu Lys Glu His Ile Ala Leu Pro
                85                  90                  95

Arg Lys Leu Glu Ser Ser Ser Leu Gln Leu
            100                 105
```

<210> SEQ ID NO 19
<211> LENGTH: 147
<212> TYPE: DNA
<213> ORGANISM: Synechocystis sp.
<220> FEATURE:
<221> NAME/KEY: misc_feature
<222> LOCATION: (1)..(147)
<223> OTHER INFORMATION: codon-optimized C-terminus of dnaB intein

<400> SEQUENCE: 19

```
atgagcccgg agatcgagaa gctctcccag tccgacatct actgggactc catcgtgtcc      60
atcaccgaaa cggggcgtgga ggaggtgttc gacctcaccg tgccaggccc gcacaacttc    120
gtggccaacg acatcatcgt gcacaac                                         147
```

<210> SEQ ID NO 20
<211> LENGTH: 49
<212> TYPE: PRT

```
<213> ORGANISM: Synechocystis sp.
<220> FEATURE:
<221> NAME/KEY: MISC_FEATURE
<222> LOCATION: (1)..(49)
<223> OTHER INFORMATION: codon-optimized C-terminus of DnaB intein

<400> SEQUENCE: 20

Met Ser Pro Glu Ile Glu Lys Leu Ser Gln Ser Asp Ile Tyr Trp Asp
1               5                   10                  15

Ser Ile Val Ser Ile Thr Glu Thr Gly Val Glu Glu Val Phe Asp Leu
            20                  25                  30

Thr Val Pro Gly Pro His Asn Phe Val Ala Asn Asp Ile Ile Val His
        35                  40                  45

Asn

<210> SEQ ID NO 21
<211> LENGTH: 15
<212> TYPE: DNA
<213> ORGANISM: Synechocystis sp.
<220> FEATURE:
<221> NAME/KEY: misc_feature
<222> LOCATION: (1)..(15)
<223> OTHER INFORMATION: dnaB extein part, C-terminal

<400> SEQUENCE: 21
tccatcgagc aggac                                                    15

<210> SEQ ID NO 22
<211> LENGTH: 5
<212> TYPE: PRT
<213> ORGANISM: Synechocystis sp.
<220> FEATURE:
<221> NAME/KEY: MISC_FEATURE
<222> LOCATION: (1)..(5)
<223> OTHER INFORMATION: DnaB extein part, C-terminal

<400> SEQUENCE: 22

Ser Ile Glu Gln Asp
1               5

<210> SEQ ID NO 23
<211> LENGTH: 30
<212> TYPE: DNA
<213> ORGANISM: Artificial
<220> FEATURE:
<221> NAME/KEY: CDS
<222> LOCATION: (1)..(30)
<223> OTHER INFORMATION: GGGGS-spacer used for vectors pICH25301 and
      pICH25881

<400> SEQUENCE: 23 gga ggc gga gga agt gga ggc ggt gga tca                             30
Gly Gly Gly Gly Ser Gly Gly Gly Gly Ser
1               5                   10

<210> SEQ ID NO 24
<211> LENGTH: 10
<212> TYPE: PRT
<213> ORGANISM: Artificial
<220> FEATURE:
<223> OTHER INFORMATION: Synthetic Construct

<400> SEQUENCE: 24

Gly Gly Gly Gly Ser Gly Gly Gly Gly Ser
1               5                   10
```

<210> SEQ ID NO 25
<211> LENGTH: 45
<212> TYPE: DNA
<213> ORGANISM: Artificial
<220> FEATURE:
<221> NAME/KEY: CDS
<222> LOCATION: (1)..(45)
<223> OTHER INFORMATION: GGGGS-spacer used for vector pICH27371

<400> SEQUENCE: 25

```
gga ggc ggt gga agt gga ggc ggt gga tca gga ggc ggt ggc tca      45
Gly Gly Gly Gly Ser Gly Gly Gly Gly Ser Gly Gly Gly Gly Ser
1               5                   10                  15
```

<210> SEQ ID NO 26
<211> LENGTH: 15
<212> TYPE: PRT
<213> ORGANISM: Artificial
<220> FEATURE:
<223> OTHER INFORMATION: Synthetic Construct

<400> SEQUENCE: 26

```
Gly Gly Gly Gly Ser Gly Gly Gly Gly Ser Gly Gly Gly Gly Ser
1               5                   10                  15
```

<210> SEQ ID NO 27
<211> LENGTH: 225
<212> TYPE: DNA
<213> ORGANISM: Bacillus amyloliquefaciens
<220> FEATURE:
<221> NAME/KEY: misc_feature
<222> LOCATION: (1)..(225)
<223> OTHER INFORMATION: codon-optimized C-terminus of the barnase
      sequence

<400> SEQUENCE: 27

```
gtggcctcca agggcaacct cgccgacgtg gccccaggga agtccatcgg cggcgacatc      60
ttctccaacc gcgagggcaa gctcccaggc aagtcgggca ggacctggag ggaggccgac     120
atcaactaca cctccggctt ccgcaactcc gaccgcatcc tctactcctc cgactggctc     180
atctacaaga ccaccgacca ctaccagacc ttcaccaaga tccgc                     225
```

<210> SEQ ID NO 28
<211> LENGTH: 75
<212> TYPE: PRT
<213> ORGANISM: Bacillus amyloliquefaciens
<220> FEATURE:
<221> NAME/KEY: MISC_FEATURE
<222> LOCATION: (1)..(75)
<223> OTHER INFORMATION: codon-optimized C-terminus of the barnase
      sequence

<400> SEQUENCE: 28

```
Val Ala Ser Lys Gly Asn Leu Ala Asp Val Ala Pro Gly Lys Ser Ile
1               5                   10                  15

Gly Gly Asp Ile Phe Ser Asn Arg Glu Gly Lys Leu Pro Gly Lys Ser
                20                  25                  30

Gly Arg Thr Trp Arg Glu Ala Asp Ile Asn Tyr Thr Ser Gly Phe Arg
            35                  40                  45

Asn Ser Asp Arg Ile Leu Tyr Ser Ser Asp Trp Leu Ile Tyr Lys Thr
        50                  55                  60

Thr Asp His Tyr Gln Thr Phe Thr Lys Ile Arg
65                  70                  75
```

<210> SEQ ID NO 29

<211> LENGTH: 1932
<212> TYPE: DNA
<213> ORGANISM: Oryza sativa
<220> FEATURE:
<221> NAME/KEY: misc_feature
<222> LOCATION: (1)..(1932)
<223> OTHER INFORMATION: ALS (acetolactate synthase) sequence from Oryza sativa
<300> PUBLICATION INFORMATION:
<308> DATABASE ACCESSION NUMBER: Genbank / AP008208
<309> DATABASE ENTRY DATE: 2005-02-02
<313> RELEVANT RESIDUES IN SEQ ID NO: (1)..(1932)

<400> SEQUENCE: 29

```
atggctacga ccgccgcggc cgcggccgcc gccctgtccg ccgccgcgac ggccaagacc     60
ggccgtaaga ccaccagcg acaccacgtc cttcccgctc gaggccgggt ggggggcggcg    120
gcggtcaggt gctcggcggt gtccccggtc acccgccgt ccccggcgcc gccggccacg    180
ccgctccggc cgtggggggcc ggccgagccc cgcaagggcg cggacatcct cgtggaggcg   240
ctggagcggt gcggcgtcag cgacgtgttc gcctacccgg cgccgcgtc catggagatc    300
caccaggcgc tgacgcgctc cccggtcatc accaaccacc tcttccgcca cgagcagggc   360
gaggcgttcg cggcgtccgg gtacgcgcgc cgtccggcc cgtcggggt ctgcgtcgcc    420
acctccggcc ccggggcaac caacctcgtg tccgcgctcg ccgacgcgct gctcgactcc    480
gtcccgatgg tcgccatcac gggccaggtc ccccgccgca tgatcggcac cgacgccttc    540
caggagacgc ccatagtcga ggtcacccgc tccatcacca agcacaatta ccttgtcctt    600
gatgtggagg acatccccg cgtcatacag gaagccttct tcctcgcgtc ctcgggccgt    660
cctggcccgg tgctggtcga catccccaag gacatccagc agcagatggc cgtgccggtc    720
tgggacacct cgatgaatct accagggtac atcgcacgcc tgcccaagcc acccgcgaca    780
gaattgcttg agcaggtctt gcgtctggtt ggcgagtcac ggcgcccgat tctctatgtc    840
ggtggtggct gctctgcatc tggtgacgaa ttgcgctggt ttgttgagct gactggtatc    900
ccagttacaa ccactctgat gggcctcggc aatttcccca gtgacgaccc gttgtccctg    960
cgcatgcttg ggatgcatgg cacggtgtac gcaaattatg ccgtggataa ggctgacctg   1020
ttgcttgcgt ttggtgtgcg gtttgatgat cgtgtgacag ggaaaattga ggcttttgca   1080
agcagggcca agattgtgca cattgacatt gatccagcag agattggaaa gaacaagcaa   1140
ccacatgtgt caatttgcgc agatgttaag cttgctttac agggcttgaa tgctctgcta   1200
caacagagca acaaagac aagttctgat tttagtgcat ggcacaatga gttggaccag   1260
cagaagaggg agtttcctct ggggtacaaa acttttggtg aagagatccc accgcaatat   1320
gccattcagg tgctggatga gctgacgaaa ggtgaggcaa tcatcgctac tggtgttggg   1380
cagcaccaga tgtgggcggc acaatattac acctacaagc ggccacggca gtggctgtct   1440
tcggctggtc tgggcgcaat gggatttggg ctgcctgctg cagctggtgc ttctgtggct   1500
aacccaggtg tcacagttgt tgatattgat gggatggta gcttcctcat gaacattcag   1560
gagctggcat tgatccgcat tgagaacctc cctgtgaagg tgatggtgtt gaacaaccaa   1620
catttgggta tggtggtgca atgggaggat aggttttaca aggcgaatag gcgcatacca   1680
tacttgggca cccggaatg tgagagcgag atatatccag attttgtgac tattgctaag   1740
gggttcaata ttcctgcagt ccgtgtaaca aagaagagtg aagtccgtgc cgccatcaag   1800
aagatgctcg agactccagg gccatacttg ttggatatca tcgtcccgca ccaggagcat   1860
gtgctgccta tgatcccaag tgggggcgca ttcaaggaca tgatcctgga tggtgatggc   1920
```
aggactgtgt at                                                                              1932

<210> SEQ ID NO 30
<211> LENGTH: 644
<212> TYPE: PRT
<213> ORGANISM: Oryza sativa
<220> FEATURE:
<221> NAME/KEY: MISC_FEATURE
<222> LOCATION: (1)..(644)
<223> OTHER INFORMATION: ALS (acetolactate synthase) sequence from Oryza
      sativa

<400> SEQUENCE: 30

```
Met Ala Thr Thr Ala Ala Ala Ala Ala Ala Leu Ser Ala Ala Ala
1               5                   10                  15

Thr Ala Lys Thr Gly Arg Lys Asn His Gln Arg His His Val Leu Pro
            20                  25                  30

Ala Arg Gly Arg Val Gly Ala Ala Val Arg Cys Ser Ala Val Ser
        35                  40                  45

Pro Val Thr Pro Pro Ser Pro Ala Pro Pro Ala Thr Pro Leu Arg Pro
    50                  55                  60

Trp Gly Pro Ala Glu Pro Arg Lys Gly Ala Asp Ile Leu Val Glu Ala
65                  70                  75                  80

Leu Glu Arg Cys Gly Val Ser Asp Val Phe Ala Tyr Pro Gly Gly Ala
                85                  90                  95

Ser Met Glu Ile His Gln Ala Leu Thr Arg Ser Pro Val Ile Thr Asn
            100                 105                 110

His Leu Phe Arg His Glu Gln Gly Glu Ala Phe Ala Ala Ser Gly Tyr
        115                 120                 125

Ala Arg Ala Ser Gly Arg Val Gly Val Cys Val Ala Thr Ser Gly Pro
    130                 135                 140

Gly Ala Thr Asn Leu Val Ser Ala Leu Ala Asp Ala Leu Leu Asp Ser
145                 150                 155                 160

Val Pro Met Val Ala Ile Thr Gly Gln Val Pro Arg Arg Met Ile Gly
                165                 170                 175

Thr Asp Ala Phe Gln Glu Thr Pro Ile Val Glu Val Thr Arg Ser Ile
            180                 185                 190

Thr Lys His Asn Tyr Leu Val Leu Asp Val Glu Asp Ile Pro Arg Val
        195                 200                 205

Ile Gln Glu Ala Phe Phe Leu Ala Ser Ser Gly Arg Pro Gly Pro Val
    210                 215                 220

Leu Val Asp Ile Pro Lys Asp Ile Gln Gln Gln Met Ala Val Pro Val
225                 230                 235                 240

Trp Asp Thr Ser Met Asn Leu Pro Gly Tyr Ile Ala Arg Leu Pro Lys
                245                 250                 255

Pro Pro Ala Thr Glu Leu Leu Glu Gln Val Leu Arg Leu Val Gly Glu
            260                 265                 270

Ser Arg Arg Pro Ile Leu Tyr Val Gly Gly Gly Cys Ser Ala Ser Gly
        275                 280                 285

Asp Glu Leu Arg Trp Phe Val Glu Leu Thr Gly Ile Pro Val Thr Thr
    290                 295                 300

Thr Leu Met Gly Leu Gly Asn Phe Pro Ser Asp Asp Pro Leu Ser Leu
305                 310                 315                 320

Arg Met Leu Gly Met His Gly Thr Val Tyr Ala Asn Tyr Ala Val Asp
                325                 330                 335

Lys Ala Asp Leu Leu Leu Ala Phe Gly Val Arg Phe Asp Asp Arg Val
```

340                 345                 350
Thr Gly Lys Ile Glu Ala Phe Ala Ser Arg Ala Lys Ile Val His Ile
                355                 360                 365
Asp Ile Asp Pro Ala Glu Ile Gly Lys Asn Lys Gln Pro His Val Ser
        370                 375                 380
Ile Cys Ala Asp Val Lys Leu Ala Leu Gln Gly Leu Asn Ala Leu Leu
385                 390                 395                 400
Gln Gln Ser Thr Thr Lys Thr Ser Ser Asp Phe Ser Ala Trp His Asn
                405                 410                 415
Glu Leu Asp Gln Gln Lys Arg Glu Phe Pro Leu Gly Tyr Lys Thr Phe
            420                 425                 430
Gly Glu Glu Ile Pro Pro Gln Tyr Ala Ile Gln Val Leu Asp Glu Leu
            435                 440                 445
Thr Lys Gly Glu Ala Ile Ile Ala Thr Gly Val Gly Gln His Gln Met
        450                 455                 460
Trp Ala Ala Gln Tyr Tyr Thr Tyr Lys Arg Pro Arg Gln Trp Leu Ser
465                 470                 475                 480
Ser Ala Gly Leu Gly Ala Met Gly Phe Gly Leu Pro Ala Ala Ala Gly
                485                 490                 495
Ala Ser Val Ala Asn Pro Gly Val Thr Val Val Asp Ile Asp Gly Asp
            500                 505                 510
Gly Ser Phe Leu Met Asn Ile Gln Glu Leu Ala Leu Ile Arg Ile Glu
        515                 520                 525
Asn Leu Pro Val Lys Val Met Val Leu Asn Asn Gln His Leu Gly Met
        530                 535                 540
Val Val Gln Trp Glu Asp Arg Phe Tyr Lys Ala Asn Arg Ala His Thr
545                 550                 555                 560
Tyr Leu Gly Asn Pro Glu Cys Glu Ser Glu Ile Tyr Pro Asp Phe Val
                565                 570                 575
Thr Ile Ala Lys Gly Phe Asn Ile Pro Ala Val Arg Val Thr Lys Lys
            580                 585                 590
Ser Glu Val Arg Ala Ala Ile Lys Lys Met Leu Glu Thr Pro Gly Pro
        595                 600                 605
Tyr Leu Leu Asp Ile Ile Val Pro His Gln Glu His Val Leu Pro Met
        610                 615                 620
Ile Pro Ser Gly Gly Ala Phe Lys Asp Met Ile Leu Asp Gly Asp Gly
625                 630                 635                 640
Arg Thr Val Tyr

<210> SEQ ID NO 31
<211> LENGTH: 1932
<212> TYPE: DNA
<213> ORGANISM: Artificial
<220> FEATURE:
<221> NAME/KEY: misc_feature
<222> LOCATION: (1)..(1932)
<223> OTHER INFORMATION: mutated version of ALS (acetolactate synthase)
      used in vectors pICH24581, pICH25301, pICH23731 and pICH25881

<400> SEQUENCE: 31

| | | | | |
|---|---|---|---|---|
| atggctacga | ccgccgcggc | cgcggccgcc | gccctgtccg | ccgccgcgac ggccaagacc | 60 |
| ggccgtaaga | accaccagcg | acaccacgtc | cttcccgctc | gaggccgggt gggggcggcg | 120 |
| gcggtcaggt | gctcggcggt | gtccccggtc | acccgccgt | cccggcgcc gccggccacg | 180 |
| ccgctccggc | cgtgggggcc | ggccgagccc | cgcaagggcg | cggacatcct cgtggaggcg | 240 |

-continued

```
ctggagcggt gcggcgtcag cgacgtgttc gcctacccgg gcggcgcgtc catggagatc    300
caccaggcgc tgacgcgctc cccggtcatc accaaccacc tcttccgcca cgagcagggc    360
gaggcgttcg cggcgtccgg gtacgcgcgc gcgtccggcc gcgtcggggt ctgcgtcgcc    420
acctccggcc ccggggcaac caacctcgtg tccgcgctcg ccgacgcgct gctcgactcc    480
gtcccgatgg tcgccatcac gggccaggtc ccccgccgca tgatcggcac cgacgccttc    540
caggagacgc ccatagtcga ggtcacccgc tccatcacca agcacaatta ccttgtcctt    600
gatgtggagg acatcccccg cgtcatacag gaagccttct tcctcgcgtc ctcgggccgt    660
cctggcccgg tgctggtcga catccccaag gacatccagc agcagatggc cgtgccggtc    720
tgggacacct cgatgaatct accagggtac atcgcacgcc tgcccaagcc acccgcgaca    780
gaattgcttg agcaggtctt gcgtctggtt ggcgagtcac ggcgcccgat tctctatgtc    840
ggtggtggct gctctgcatc tggtgacgaa ttgcgctggt tgttgagct gactggtatc    900 ccagttacaa ccactctgat gggcctcggc aatttcccca gtgacgaccc gttgtccctg    960
cgcatgcttg gatgcatgg cacggtgtac gcaaattatg ccgtggataa ggctgacctg   1020
ttgcttgcgt ttggtgtgcg gtttgatgat cgtgtgacag ggaaaattga ggcttttgca   1080
agcagggcca agattgtgca cattgacatt gatccagcag agattggaaa gaacaagcaa   1140
ccacatgtgt caatttgcgc agatgttaag cttgctttac agggcttgaa tgctctgcta   1200
caacagagca caacaaagac aagttctgat tttagtgcat ggcacaatga gttggaccag   1260
cagaagaggg agtttcctct ggggtacaaa actttggtg aagagatccc accgcaatat   1320
gccattcagg tgctggatga gctgacgaaa ggtgaggcaa tcatcgctac tggtgttggg   1380
cagcaccaga tgtgggcggc acaatattac acctacaagc ggccacggca gtggctgtct   1440
tcggctggtc tgggcgcaat gggatttggg ctgcctgctg cagctggtgc ttctgtggct   1500
aacccaggtg tcacagttgt tgatattgat ggggatggta gcttcctcat gaacattcag   1560
gagctggcat tgatccgcat tgagaacctc cctgtgaagg tgatggtgtt gaacaaccaa   1620
catttgggta tggtggtgca acttgaggat aggttttaca aggcgaatag ggcgcataca   1680
tacttgggca acccggaatg tgagagcgag atatatccag attttgtgac tattgctaag   1740
gggttcaata ttcctgcagt ccgtgtaaca aagaagagtg aagtccgtgc cgccatcaag   1800
aagatgctcg agactccagg gccatacttg ttggatatca tcgtcccgca ccaggagcat   1860
gtgctgccta tgatcccaag tggggggcgca ttcaaggaca tgatcctgga tggtgatggc   1920
aggactgtgt ac                                                       1932
```

<210> SEQ ID NO 32
<211> LENGTH: 644
<212> TYPE: PRT
<213> ORGANISM: Artificial
<220> FEATURE:
<221> NAME/KEY: MISC_FEATURE
<222> LOCATION: (1)..(644)
<223> OTHER INFORMATION: mutated version of ALS (acetolactate synthase)
      used in vectors pICH24581, pICH25301, pICH23731 and pICH25881

<400> SEQUENCE: 32

```
Met Ala Thr Thr Ala Ala Ala Ala Ala Ala Leu Ser Ala Ala Ala
1               5                   10                  15

Thr Ala Lys Thr Gly Arg Lys Asn His Gln Arg His His Val Leu Pro
                20                  25                  30

Ala Arg Gly Arg Val Gly Ala Ala Ala Val Arg Cys Ser Ala Val Ser
            35                  40                  45
```

```
Pro Val Thr Pro Pro Ser Pro Ala Pro Ala Thr Pro Leu Arg Pro
    50                  55                  60

Trp Gly Pro Ala Glu Pro Arg Lys Gly Ala Asp Ile Leu Val Glu Ala
65                  70                  75                  80

Leu Glu Arg Cys Gly Val Ser Asp Val Phe Ala Tyr Pro Gly Gly Ala
                85                  90                  95

Ser Met Glu Ile His Gln Ala Leu Thr Arg Ser Pro Val Ile Thr Asn
            100                 105                 110

His Leu Phe Arg His Glu Gln Gly Glu Ala Phe Ala Ala Ser Gly Tyr
        115                 120                 125

Ala Arg Ala Ser Gly Arg Val Gly Val Cys Val Ala Thr Ser Gly Pro
    130                 135                 140

Gly Ala Thr Asn Leu Val Ser Ala Leu Ala Asp Ala Leu Leu Asp Ser
145                 150                 155                 160

Val Pro Met Val Ala Ile Thr Gly Gln Val Pro Arg Arg Met Ile Gly
                165                 170                 175

Thr Asp Ala Phe Gln Glu Thr Pro Ile Val Glu Val Thr Arg Ser Ile
            180                 185                 190

Thr Lys His Asn Tyr Leu Val Leu Asp Val Glu Asp Ile Pro Arg Val
        195                 200                 205

Ile Gln Glu Ala Phe Phe Leu Ala Ser Ser Gly Arg Pro Gly Pro Val
    210                 215                 220

Leu Val Asp Ile Pro Lys Asp Ile Gln Gln Gln Met Ala Val Pro Val
225                 230                 235                 240

Trp Asp Thr Ser Met Asn Leu Pro Gly Tyr Ile Ala Arg Leu Pro Lys
                245                 250                 255

Pro Pro Ala Thr Glu Leu Leu Glu Gln Val Leu Arg Leu Val Gly Glu
            260                 265                 270

Ser Arg Arg Pro Ile Leu Tyr Val Gly Gly Gly Cys Ser Ala Ser Gly
        275                 280                 285

Asp Glu Leu Arg Trp Phe Val Glu Leu Thr Gly Ile Pro Val Thr Thr
    290                 295                 300

Thr Leu Met Gly Leu Gly Asn Phe Pro Ser Asp Asp Pro Leu Ser Leu
305                 310                 315                 320

Arg Met Leu Gly Met His Gly Thr Val Tyr Ala Asn Tyr Ala Val Asp
                325                 330                 335

Lys Ala Asp Leu Leu Leu Ala Phe Gly Val Arg Phe Asp Asp Arg Val
            340                 345                 350

Thr Gly Lys Ile Glu Ala Phe Ala Ser Arg Ala Lys Ile Val His Ile
        355                 360                 365

Asp Ile Asp Pro Ala Glu Ile Gly Lys Asn Lys Gln Pro His Val Ser
    370                 375                 380

Ile Cys Ala Asp Val Lys Leu Ala Leu Gln Gly Leu Asn Ala Leu Leu
385                 390                 395                 400

Gln Gln Ser Thr Thr Lys Thr Ser Ser Asp Phe Ser Ala Trp His Asn
                405                 410                 415

Glu Leu Asp Gln Gln Lys Arg Glu Phe Pro Leu Gly Tyr Lys Thr Phe
            420                 425                 430

Gly Glu Glu Ile Pro Pro Gln Tyr Ala Ile Gln Val Leu Asp Glu Leu
        435                 440                 445

Thr Lys Gly Glu Ala Ile Ile Ala Thr Gly Val Gly Gln His Gln Met
    450                 455                 460
```

```
Trp Ala Ala Gln Tyr Tyr Thr Tyr Lys Arg Pro Arg Gln Trp Leu Ser
465                 470                 475                 480

Ser Ala Gly Leu Gly Ala Met Gly Phe Gly Leu Pro Ala Ala Ala Gly
            485                 490                 495

Ala Ser Val Ala Asn Pro Gly Val Thr Val Val Asp Ile Asp Gly Asp
        500                 505                 510

Gly Ser Phe Leu Met Asn Ile Gln Glu Leu Ala Leu Ile Arg Ile Glu
        515                 520                 525

Asn Leu Pro Val Lys Val Met Val Leu Asn Asn Gln His Leu Gly Met
        530                 535                 540

Val Val Gln Leu Glu Asp Arg Phe Tyr Lys Ala Asn Arg Ala His Thr
545                 550                 555                 560

Tyr Leu Gly Asn Pro Glu Cys Glu Ser Glu Ile Tyr Pro Asp Phe Val
            565                 570                 575

Thr Ile Ala Lys Gly Phe Asn Ile Pro Ala Val Arg Val Thr Lys Lys
        580                 585                 590

Ser Glu Val Arg Ala Ala Ile Lys Lys Met Leu Glu Thr Pro Gly Pro
        595                 600                 605

Tyr Leu Leu Asp Ile Ile Val Pro His Gln Glu His Val Leu Pro Met
610                 615                 620

Ile Pro Ser Gly Gly Ala Phe Lys Asp Met Ile Leu Asp Gly Asp Gly
625                 630                 635                 640

Arg Thr Val Tyr
```

<210> SEQ ID NO 33
<211> LENGTH: 1209
<212> TYPE: DNA
<213> ORGANISM: Artificial
<220> FEATURE:
<221> NAME/KEY: misc_feature
<222> LOCATION: (1)..(1209)
<223> OTHER INFORMATION: codon-optimized N-terminus of ALS (acetolactate synthase) from Oryza sativa

<400> SEQUENCE: 33

```
atggctacga ccgccgcggc cgcggccgcc gccctgtccg ccgccgcgac ggccaagacc    60
ggccgtaaga ccaccagcg acaccacgtc cttcccgctc gaggccgggt ggggggcggcg   120
gcggtcaggt gctcggcggt gtccccggtc accccgccgt ccccggcgcc gccggccacg   180
ccgctccggc cgtgggggcc ggccgagccc cgcaagggcg cggacatcct cgtggaggcg   240
ctggagcggt gcggcgtcag cgacgtgttc gcctacccgg cggcgcgtc catggagatc   300
caccaggcgc tgacgcgctc cccggtcatc accaaccacc tcttccgcca cgagcagggc   360
gaggcgttcg cggcgtccgg gtacgcgcgc cgtccggcc cgtcggggt ctgcgtcgcc   420
acctccggcc ccgggcaac caacctcgtg tccgcgctcg ccgacgcgct gctcgactcc   480
gtcccgatgg tcgccatcac gggccaggtc cccgccgca tgatcggcac cgacgccttc   540
caggagacgc ccatagtcga ggtcacccgc tccatcacca gcacaatta ccttgtcctt   600
gatgtggagg acatcccccg cgtcatacag gaagccttct tcctcgcgtc ctcgggccgt   660
cctggcccgg tgctggtcga catccccaag gacatccagc agcagatggc cgtgccggtc   720
tgggacacct cgatgaatct accagggtac atcgcacgcc tgcccaagcc acccgcgaca   780
gaattgcttg agcaggtctt gcgtctggtt ggcgagtcac ggcgcccgat tctctatgtc   840
ggtggtggct gctctgcatc tggtgacgaa ttgcgctggt tgttgagct gactggtatc   900
ccagttacaa ccactctgat gggcctcggc aatttcccca gtgacgaccc gttgtccctg   960
```

-continued

```
cgcatgcttg ggatgcatgg cacggtgtac gcaaattatg ccgtggataa ggctgacctg      1020
ttgcttgcgt ttggtgtgcg gtttgatgat cgtgtgacag ggaaaattga ggcttttgca      1080
agcagggcca agattgtgca cattgacatt gatccagcag agattggaaa gaacaagcaa      1140
ccacatgtgt caatttgcgc agatgttaag cttgctttac agggcttgaa tgctctgcta      1200
caacagagc                                                              1209
```

<210> SEQ ID NO 34
<211> LENGTH: 403
<212> TYPE: PRT
<213> ORGANISM: Artificial
<220> FEATURE:
<221> NAME/KEY: MISC_FEATURE
<222> LOCATION: (1)..(403)
<223> OTHER INFORMATION: codon-optimized N-terminus of ALS (acetolactate synthase) from Oryza sativa

<400> SEQUENCE: 34

```
Met Ala Thr Thr Ala Ala Ala Ala Ala Ala Leu Ser Ala Ala Ala
1               5                   10                  15

Thr Ala Lys Thr Gly Arg Lys Asn His Gln Arg His His Val Leu Pro
            20                  25                  30

Ala Arg Gly Arg Val Gly Ala Ala Val Arg Cys Ser Ala Val Ser
        35                  40                  45

Pro Val Thr Pro Pro Ser Pro Ala Pro Ala Thr Pro Leu Arg Pro
    50                  55                  60

Trp Gly Pro Ala Glu Pro Arg Lys Gly Ala Asp Ile Leu Val Glu Ala
65                  70                  75                  80

Leu Glu Arg Cys Gly Val Ser Asp Val Phe Ala Tyr Pro Gly Gly Ala
                85                  90                  95

Ser Met Glu Ile His Gln Ala Leu Thr Arg Ser Pro Val Ile Thr Asn
            100                 105                 110

His Leu Phe Arg His Glu Gln Gly Glu Ala Phe Ala Ala Ser Gly Tyr
        115                 120                 125

Ala Arg Ala Ser Gly Arg Val Gly Val Cys Val Ala Thr Ser Gly Pro
    130                 135                 140

Gly Ala Thr Asn Leu Val Ser Ala Leu Ala Asp Ala Leu Leu Asp Ser
145                 150                 155                 160

Val Pro Met Val Ala Ile Thr Gly Gln Val Pro Arg Arg Met Ile Gly
                165                 170                 175

Thr Asp Ala Phe Gln Glu Thr Pro Ile Val Glu Val Thr Arg Ser Ile
            180                 185                 190

Thr Lys His Asn Tyr Leu Val Leu Asp Val Glu Asp Ile Pro Arg Val
        195                 200                 205

Ile Gln Glu Ala Phe Phe Leu Ala Ser Ser Gly Arg Pro Gly Pro Val
    210                 215                 220

Leu Val Asp Ile Pro Lys Asp Ile Gln Gln Gln Met Ala Val Pro Val
225                 230                 235                 240

Trp Asp Thr Ser Met Asn Leu Pro Gly Tyr Ile Ala Arg Leu Pro Lys
                245                 250                 255

Pro Pro Ala Thr Glu Leu Leu Glu Gln Val Leu Arg Leu Val Gly Glu
            260                 265                 270

Ser Arg Arg Pro Ile Leu Tyr Val Gly Gly Gly Cys Ser Ala Ser Gly
        275                 280                 285

Asp Glu Leu Arg Trp Phe Val Glu Leu Thr Gly Ile Pro Val Thr Thr
```

```
                290                 295                 300
Thr Leu Met Gly Leu Gly Asn Phe Pro Ser Asp Asp Pro Leu Ser Leu
305                 310                 315                 320

Arg Met Leu Gly Met His Gly Thr Val Tyr Ala Asn Tyr Ala Val Asp
                325                 330                 335

Lys Ala Asp Leu Leu Ala Phe Gly Val Arg Phe Asp Asp Arg Val
                340                 345                 350

Thr Gly Lys Ile Glu Ala Phe Ala Ser Arg Ala Lys Ile Val His Ile
            355                 360                 365

Asp Ile Asp Pro Ala Glu Ile Gly Lys Asn Lys Gln Pro His Val Ser
        370                 375                 380

Ile Cys Ala Asp Val Lys Leu Ala Leu Gln Gly Leu Asn Ala Leu Leu
385                 390                 395                 400

Gln Gln Ser
```

<210> SEQ ID NO 35
<211> LENGTH: 21
<212> TYPE: DNA
<213> ORGANISM: Synechocystis sp.
<220> FEATURE:
<221> NAME/KEY: misc_feature
<222> LOCATION: (1)..(21)
<223> OTHER INFORMATION: dnaE extein part, N-terminal

<400> SEQUENCE: 35
gacgtcaagt ttgcggaata t                                              21

<210> SEQ ID NO 36
<211> LENGTH: 7
<212> TYPE: PRT
<213> ORGANISM: Synechocystis sp.
<220> FEATURE:
<221> NAME/KEY: MISC_FEATURE
<222> LOCATION: (1)..(7)
<223> OTHER INFORMATION: DnaE extein part, N-terminal

<400> SEQUENCE: 36

Asp Val Lys Phe Ala Glu Tyr
1               5

<210> SEQ ID NO 37
<211> LENGTH: 369
<212> TYPE: DNA
<213> ORGANISM: Synechocystis sp.
<220> FEATURE:
<221> NAME/KEY: misc_feature
<222> LOCATION: (1)..(369)
<223> OTHER INFORMATION: N-terminus of dnaE intein

<400> SEQUENCE: 37
tgcctcagtt ttggcaccga aattttaacc gttgagtacg gcccattgcc cattggcaaa    60
attgtgagtg aagaaattaa ttgttctgtg tacagtgttg atccagaagg gagagtttac   120
acccaggcga tcgcccaatg gcatgaccgg ggagagcagg aagtattgga atatgaattg   180
gaagatggtt cagtaatccg agctacctct gaccaccgct ttttaaccac cgattatcaa   240
ctgttggcga tcgaagaaat ttttgctagg caactggact tgttgacttt agaaaatatt   300
aagcaaactg aagaagctct tgacaaccat cgtcttccct ttccattact tgacgctggg   360
acaattaaa                                                           369

<210> SEQ ID NO 38

<211> LENGTH: 123
<212> TYPE: PRT
<213> ORGANISM: Synechocystis sp.
<220> FEATURE:
<221> NAME/KEY: MISC_FEATURE
<222> LOCATION: (1)..(123)
<223> OTHER INFORMATION: N-terminus of DnaE intein

<400> SEQUENCE: 38

```
Cys Leu Ser Phe Gly Thr Glu Ile Leu Thr Val Glu Tyr Gly Pro Leu
1               5                   10                  15

Pro Ile Gly Lys Ile Val Ser Glu Glu Ile Asn Cys Ser Val Tyr Ser
            20                  25                  30

Val Asp Pro Glu Gly Arg Val Tyr Thr Gln Ala Ile Ala Gln Trp His
        35                  40                  45

Asp Arg Gly Glu Gln Glu Val Leu Glu Tyr Glu Leu Glu Asp Gly Ser
    50                  55                  60

Val Ile Arg Ala Thr Ser Asp His Arg Phe Leu Thr Thr Asp Tyr Gln
65                  70                  75                  80

Leu Leu Ala Ile Glu Glu Ile Phe Ala Arg Gln Leu Asp Leu Leu Thr
                85                  90                  95

Leu Glu Asn Ile Lys Gln Thr Glu Glu Ala Leu Asp Asn His Arg Leu
            100                 105                 110

Pro Phe Pro Leu Leu Asp Ala Gly Thr Ile Lys
        115                 120
```

<210> SEQ ID NO 39
<211> LENGTH: 108
<212> TYPE: DNA
<213> ORGANISM: Synechocystis sp.
<220> FEATURE:
<221> NAME/KEY: misc_feature
<222> LOCATION: (1)..(108)
<223> OTHER INFORMATION: C-terminus of dnaE intein

<400> SEQUENCE: 39

```
atggttaaag ttatcggtcg tcgttccctc ggagtgcaaa gaatatttga tattggtctt    60
ccccaagacc ataattttct gctagccaat ggggcgatcg ccgccaat                108
```

<210> SEQ ID NO 40
<211> LENGTH: 36
<212> TYPE: PRT
<213> ORGANISM: Synechocystis sp.
<220> FEATURE:
<221> NAME/KEY: MISC_FEATURE
<222> LOCATION: (1)..(36)
<223> OTHER INFORMATION: C-terminus of DnaE intein

<400> SEQUENCE: 40

```
Met Val Lys Val Ile Gly Arg Arg Ser Leu Gly Val Gln Arg Ile Phe
1               5                   10                  15

Asp Ile Gly Leu Pro Gln Asp His Asn Phe Leu Leu Ala Asn Gly Ala
            20                  25                  30

Ile Ala Ala Asn
        35
```

<210> SEQ ID NO 41
<211> LENGTH: 15
<212> TYPE: DNA
<213> ORGANISM: Synechocystis sp.
<220> FEATURE:
<221> NAME/KEY: misc_feature
<222> LOCATION: (1)..(15)

```
<223> OTHER INFORMATION: dnaE extein part, C-terminal

<400> SEQUENCE: 41
tgttttaacc atggg                                                      15

<210> SEQ ID NO 42
<211> LENGTH: 5
<212> TYPE: PRT
<213> ORGANISM: Synechocystis sp.
<220> FEATURE:
<221> NAME/KEY: MISC_FEATURE
<222> LOCATION: (1)..(5)
<223> OTHER INFORMATION: DnaE extein part, C-terminal

<400> SEQUENCE: 42

Cys Phe Asn His Gly
1               5

<210> SEQ ID NO 43
<211> LENGTH: 723
<212> TYPE: DNA
<213> ORGANISM: Oryza sativa
<220> FEATURE:
<221> NAME/KEY: misc_feature
<222> LOCATION: (1)..(723)
<223> OTHER INFORMATION: codon-optimized C-terminus of ALS (acetolactate
      synthase)

<400> SEQUENCE: 43
acaacaaaga caagttctga ttttagtgca tggcacaatg agttggacca gcagaagagg       60
gagtttcctc tggggtacaa aacttttggt gaagagatcc caccgcaata tgccattcag      120
gtgctggatg agctgacgaa aggtgaggca atcatcgcta ctggtgttgg gcagcaccag      180
atgtgggcgg cacaatatta cacctacaag cggccacggc agtggctgtc ttcggctggt      240
ctgggcgcaa tgggatttgg gctgcctgct gcagctggtg cttctgtggc taacccaggt      300
gtcacagttg ttgatattga tggggatggt agcttcctca tgaacattca ggagctggca      360
ttgatccgca ttgagaacct ccctgtgaag gtgatggtgt tgaacaacca acatttgggt      420
atggtggtgc aacttgagga taggttttac aaggcgaata gggcgcatac atacttgggc      480
aacccggaat gtgagagcga gatatatcca gattttgtga ctattgctaa ggggttcaat      540
attcctgcag tccgtgtaac aaagaagagt gaagtccgtg ccgccatcaa gaagatgctc      600
gagactccag ggccatactt gttggatatc atcgtcccgc accaggagca tgtgctgcct      660
atgatcccaa gtggggcgc attcaaggac atgatcctgg atggtgatgg caggactgtg      720
tac                                                                   723

<210> SEQ ID NO 44
<211> LENGTH: 241
<212> TYPE: PRT
<213> ORGANISM: Oryza sativa
<220> FEATURE:
<221> NAME/KEY: MISC_FEATURE
<222> LOCATION: (1)..(241)
<223> OTHER INFORMATION: codon-optimized C-terminus of ALS (acetolactate
      synthase)

<400> SEQUENCE: 44

Thr Thr Lys Thr Ser Ser Asp Phe Ser Ala Trp His Asn Glu Leu Asp
1               5                  10                  15

Gln Gln Lys Arg Glu Phe Pro Leu Gly Tyr Lys Thr Phe Gly Glu Glu
            20                  25                  30
```

Ile Pro Pro Gln Tyr Ala Ile Gln Val Leu Asp Glu Leu Thr Lys Gly
        35                  40                  45

Glu Ala Ile Ile Ala Thr Gly Val Gly Gln His Gln Met Trp Ala Ala
 50                  55                  60

Gln Tyr Tyr Thr Tyr Lys Arg Pro Arg Gln Trp Leu Ser Ser Ala Gly
65                  70                  75                  80

Leu Gly Ala Met Gly Phe Gly Leu Pro Ala Ala Gly Ala Ser Val
                85                  90                  95

Ala Asn Pro Gly Val Thr Val Val Asp Ile Asp Gly Asp Gly Ser Phe
            100                 105                 110

Leu Met Asn Ile Gln Glu Leu Ala Leu Ile Arg Ile Glu Asn Leu Pro
            115                 120                 125

Val Lys Val Met Val Leu Asn Asn Gln His Leu Gly Met Val Val Gln
130                 135                 140

Leu Glu Asp Arg Phe Tyr Lys Ala Asn Arg Ala His Thr Tyr Leu Gly
145                 150                 155                 160

Asn Pro Glu Cys Glu Ser Glu Ile Tyr Pro Asp Phe Val Thr Ile Ala
                165                 170                 175

Lys Gly Phe Asn Ile Pro Ala Val Arg Val Thr Lys Lys Ser Glu Val
            180                 185                 190

Arg Ala Ala Ile Lys Lys Met Leu Glu Thr Pro Gly Pro Tyr Leu Leu
            195                 200                 205

Asp Ile Ile Val Pro His Gln Glu His Val Leu Pro Met Ile Pro Ser
            210                 215                 220

Gly Gly Ala Phe Lys Asp Met Ile Leu Asp Gly Asp Gly Arg Thr Val
225                 230                 235                 240

Tyr

<210> SEQ ID NO 45
<211> LENGTH: 13833
<212> TYPE: DNA
<213> ORGANISM: Artificial
<220> FEATURE:
<221> NAME/KEY: misc_feature
<222> LOCATION: (1)..(13833)
<223> OTHER INFORMATION: complete sequence of vector pICH24581

<400> SEQUENCE: 45
ctacgccccc aactgagaga actcaaaggt taccccagtt ggggcacggc gcgccacact    60
cgagaattcg gcgccttttt tttacacagt tcaaagtgaa ttttggttaa aaccctcagg   120
ttgtatttgg ataatgggga ataatgtggg tgggaattgg gattgggaaa tgaacgaagg   180
gttaggatta aatggaagaa ggagaataaa tggttaaaat ttaaagatgt cttttagtgg   240
gtgggaaatg atttcccttt cccattagcc aaacggggcc tcagtatatt ttcaattaac   300
agaagtttaa tacttaataa tttaaatgac agttcaatat tttagccatg acacatggca   360
tccaatgaaa gggtcgtcca ctagaaataa aggtgacaga cggtcactga ataggtacac   420
ccataccagc cacctttcta ttgtctttgc acttgggatt gaaaaggtgg tcaccaaggg   480
gttaaaaccc tgtattcatt cgggaaatgt ttttgccaca caatgagtt ccaaatacac   540 tgagtgacac tacgggtcag tccctaaaat ttctgaaatg ttgttaccta cccgtctctt   600
tgtccaaaaa taaccaaac ccgtacggtg tgaatatacc ttcaatgtta cctacactgt   660
acaaggttag cttattttgt aacggaggga acatacatct ttccgatacc cagcattaat   720
aattgttgtg ccgccttggt tcagttcaaa tttcttttta caaaattccg cttgcatctt   780

```
tgtcccggcg cggcaaaaaa aaaatccaca ataaaggtat catataaaaa caatgatggc    840
agttaatcag tttaggttgg tcactatctt aatagatgca aattaagttg ggttgtagcg    900
aaaccaacga acggcatttg ttttgtgctc ccacgataca atcccttaaa tcagcacaca    960
cgcacaatgc atgcaccaca ttttagatcg atttcgtaga gaatatttcg atcacatagc   1020
cacaattaat ctacattcta gaagctccaa caaacttatt taattagttc ctgcaaatta   1080
acatttacaa atatctcaaa ctgaagaaat aactttaatt gcaatgccgg cagccaaccc   1140
ggcgtgtatg cttccatttg ttcggatgta aaaggtgctg tttatccata ggaagaggtg   1200
taatattaat aactactcca tccgtttcta aatatttgac gtcattgact atttgtttaa   1260
atatgtttga atgttcgtct tattttaaaa aaatttaagt aattattaat tattttctat   1320
cattttgatt tattggttaa ataccttta tatgtataca tatagttttta catatttcac   1380 aaaagttttt gaatatgacg aaaggttaaa catgtgctaa aaagtcaatg gtatcaaata   1440
tttagaaacg gagggagtat gtttgttgaa aatgttttac cttctctcaa tcttaataaa   1500
tttggtcagg gcaggcaccg gaaaaaaaaa acaggaaggc ataacagcaa aacaaaaaca   1560
gtggaaatta agcattgcta attacaaact tttctgatca ttcacaccat tttcatgttt   1620
gatcccgctc aaacttcact tcaacagctt agacactctt agctagcaaa agtcctaatc   1680
acaggcatta taaatggcac aggcaattag cctcatctac acacactgcc atcactccaa   1740
ttaaccaaag ctaattaagc atcgattcat gagcccggag atcgagaagc tctcccagtc   1800
cgacatctac tgggactcca tcgtgtccat caccgaaacg ggcgtggagg aggtgttcga   1860
cctcaccgtg ccaggcccgc acaacttcgt ggccaacgac atcatcgtgc acaactccat   1920
cgagcaggac gtggcctcca agggcaacct cgccgacgtg ccccaggga agtccatcgg   1980 cggcgacatc ttctccaacc gcgagggcaa gctcccaggc aagtcgggca ggacctggag   2040
ggaggccgac atcaactaca cctccggctt ccgcaactcc gaccgcatcc tctactcctc   2100
cgactggctc atctacaaga ccaccgacca ctaccagacc ttcaccaaga tccgctgagg   2160
atcctctaga gtcctgcttt aatgagatat gcgagacgcc tatgatcgca tgatatttgc   2220
tttcaattct gttgtgcacg ttgtaaaaaa cctgagcatg tgtagctcag atccttaccg   2280
ccggtttcgg ttcattctaa tgaatatatc acccgttact atcgtatttt tatgaataat   2340
attctccgtt caattactg attgtaccct actacttata tgtacaatat taaaatgaaa   2400
acaatatatt gtgctgaata ggtttatagc gacatctatg atagagcgcc acaataacaa   2460
acaattgcgt tttattatta caaatccaat ttaaaaaaaa gcggcagaac cggtcaaacc   2520
taaaagactg attacataaa tcttattcaa atttcaaaag tgccccaggg gctagtatct   2580 acgcacacc gagcggcgaa ctaataacgc tcactgaagg gaactccggt tccccgccgg   2640
cgcgcatggg tgagattcct tgaagttgag tattggccgt ccgctctacc gaaagttacg   2700
ggcaccattc aacccggtcc agcacggcgg ccgggtaacc gacttgctgc cccgagaatt   2760
atgcagcatt tttttggtgt atgtgccaaa tgaagtgcag gtcaaacctt gacagtgacg   2820
acaaatcgtt gggcgggtcc agggcgaatt ttgcgacaac atgtcgaggc tcagcaggac   2880
ctgcaggtac cacaactagt gatggtgag gtggagtacg cgcccgggga gcccaagggc   2940
acgccctggc acccgcaccg cggcttcgag ctcgagtgca ggtcgatcta gtaacataga   3000
tgacaccgcg cgcgataatt tatcctagtt tgcgcgctat attttgtttt ctatcgcgta   3060
ttaaatgtat aattgcggga ctctaatcat aaaaacccat ctcataaata acgtcatgca   3120
ttacatgtta attattacat gcttaacgta attcaacaga aattatatga taatcatcgc   3180
```

```
aagaccggca acaggattca atcttaagaa actttattgc caaatgtttg aacgatctgc    3240
ttgactctag agcttagcat tagtacacag tcctgccatc accatccagg atcatgtcct    3300
tgaatgcgcc cccacttggg atcataggca gcacatgctc ctggtgcggg acgatgatat    3360
ccaacaagta tggccctgga gtctcgagca tcttcttgat ggcggcacgg acttcactct    3420
tctttgttac acggactgca ggaatattga accccttagc aatagtcaca aaatctggat    3480
atatctcgct ctcacattcc gggttgccca agtatgtatg cgccctattc gccttgtaaa    3540
acctatcctc aagttgcacc accatacccaaatgttggtt gttcaacacc atcaccttca    3600
cagggaggtt ctcaatgcgg atcaatgcca gctcctgaat gttcatgagg aagctaccat    3660
ccccatcaat atcaacaact gtgacacctg ggttagccac agaagcacca gctgcagcag    3720
gcagcccaaa tcccattgcg cccagaccag ccgaagacag ccactgccgt ggccgcttgt    3780
aggtgtaata ttgtgccgcc cacatctggt gctgcccaac accagtagcg atgattgcct    3840
cacctttcgt cagctcatcc agcacctgaa tggcatattg cggtgggatc tcttcaccaa    3900
aagttttgta ccccagagga aactccctct tctgctggtc caactcattg tgccatgcac    3960
taaaatcaga acttgtcttt gttgtgctct gttgtagcag agcattcaag ccctgtaaag    4020
caagcttaac atctgcgcaa attgacacat gtggttgctt gttctttcca atctctgctg    4080
gatcaatgtc aatgtgcaca atcttggccc tgcttgcaaa agcctcaatt ttccctgtca    4140
cacgatcatc aaaccgcaca ccaaacgcaa gcaacaggtc agccttatcc acggcataat    4200
ttgcgtacac cgtgccatgc atcccaagca tgcgcaggga caacgggtcg tcactgggga    4260
aattgccgag gcccatcaga gtggttgtaa ctgggatacc agtcagctca acaaaccagc    4320
gcaattcgtc accagatgca gagcagccac caccgacata gagaatcggg cgccgtgact    4380
cgccaaccag acgcaagacc tgctcaagca attctgtcgc gggtggcttg ggcaggcgtg    4440
cgatgtaccc tggtagattc atcgaggtgt cccagaccgg cacggccatc tgctgctgga    4500
tgtccttggg gatgtcgacc agcaccgggc caggacggcc cgaggacgcg aggaagaagg    4560
cttcctgtat gacgcggggg atgtcctcca catcaaggac aaggtaattg tgcttggtga    4620
tggagcgggt gacctcgact atgggcgtct cctggaaggc gtcggtgccg atcatgcggc    4680
gggggacctg gcccgtgatg gcgaccatcg ggacggagtc gagcagcgcg tcggcgagcg    4740
cggacacgag gttggttgcc ccggggccgg aggtggcgac gcagaccccg acgcggccgg    4800
acgcgcgcgc gtacccggac gccgcgaacg cctcgccctg ctcgtggcgg aagaggtggt    4860
tggtgatgac cggggagcgc gtcagcgcct ggtggatctc catggacgcg ccgcccgggt    4920
aggcgaacac gtcgctgacg ccgcaccgct ccagcgcctc cacgaggatg tccgcgccct    4980 tgcgggctc ggccggcccc cacggccgga gcggcgtggc cggcggcgcc ggggacggcg    5040
gggtgaccgg ggacaccgcc gagcacctga ccgccgccgc cccacccgg cctcgagcgg    5100 gaaggacgtg gtgtcgctgg tggttcttac ggccggtctt ggccgtcgcg gcggcggaca    5160
gggcggcggc cgcggccgcg gcggtcgtag ccatggttta tcgatagctt atcgtctacc    5220
tacaaaaaag ctccgcacga ggctgcattt gtcacaaatc atgaaaagaa aaactaccga    5280
tgaacaatgc tgagggattc aaattctacc cacaaaaaga agaaagaaag atctagcaca    5340
tctaagcctg acgaagcagc agaaatatat aaaaatataa accatagtgc ccttttcccc    5400
tcttcctgat cttgtttagc atggcggaaa ttttaaaccc cccatcatct cccccaacaa    5460
cggcggatcg cagatctaca tccgagagcc ccattccccg cgagatccgg gccggatcca    5520
```

```
cgccggcgag agccccagcc gcgagatccc gccccctcccg cgcaccgatc tgggcgcgca      5580
cgaagccgcc tctcgcccac ccaaactacc aaggccaaag atcgagaccg agacggaaaa      5640
aaaaaacgga gaaagaaaga ggagaggggc ggggtggtta ccggcgcggc ggcggcggag      5700
ggggaggggg gaggagctcg tcgtccggca gcgaggggggg aggaggtgga ggtggtggtg    5760
gtggtggtgg tagggttggg gggatgggag gagaggggggg ggtatgtata tagtggcgat    5820
ggggggcgtt tctttggaag cggagggagg gccggcctcg tcgctggctc gcgatcctcc     5880
tcgcgtttcc ggcccccacg acccggaccc acctgctgtt ttttcttttt cttttttttc    5940
tttcttttt tttttttggc tgcgagacgt gcggtgcgtg cggacaactc acggtgatag      6000
tggggggtg tggagactat tgtccagttg gctggactgg ggtgggttgg gttgggttgg     6060
gttgggctgg gcttgctatg gatcgtggat agcactttgg gctttaggaa ctttaggggt   6120
tgtttttgta aatgttttga gtctaagttt atctttatt tttactagaa aaatacccca      6180
tgcgctgcaa cgggggaaag ctattttaat cttattattg ttcattgtga gaattcgcct    6240
gaatatatat ttttctcaaa aattatgtca aattagcata tgggtttttt taaagatatt    6300
tcttatacaa atccctctgt atttacaaaa gcaaacgaac ttaaaacccg actcaaatac    6360
agatatgcat ttccaaaagc gaataaactt aaaaaccaat tcatacaaaa atgacgtatc    6420
aaagtaccga caaaaacatc ctcaattttt ataatagtag aaaagagtaa atttcactt    6480
gggccaccttt ttattaccga tattttactt tataccacct tttaactgat gttttcactt  6540
ttgaccaggt aatcttacct ttgttttat ttggactatc ccgactctct tctcaagcat    6600
atgaatgacc tcgaccggca tgcagatctg gcgcgccatg caggtcctgc tgagcctcga    6660
catgttgtcg caaaattcgc cctggacccg cccaacgatt tgtcgtcact gtcaaggttt    6720
gacctgcact tcatttggca catacaccaa aaaaatgctg cataattctc ggggcagcaa    6780
gtcggttacc cggccgccgt gctggaccgg gttgaatggt gcccgtaact ttcggtagag    6840
cggacggcca atactcaact tcaaggaatc tcacccatgc gcgccggcgg ggaaccggag    6900
ttcccttcag tgagcgttat tagttcgccg ctcggtgtgt cgtagatact agcccctggg    6960
gcactttga aatttgaata agatttatgt aatcagtctt ttaggtttga ccggttctgc     7020
cgctttttt aaaattggat ttgtaataat aaaacgcaat tgtttgttat tgtggcgctc    7080
tatcatagat gtcgctataa acctattcag cacaatatat tgttttcatt ttaatattgt    7140
acatataagt agtagggtac aatcagtaaa ttgaacggag aatattattc ataaaaatac    7200
gatagtaacg ggtgatatat tcattagaat gaaccgaaac cggcggtaag gatctgagct   7260
acacatgctc aggtttttta caacgtgcac aacagaattg aaagcaaata tcatgcgatc    7320
ataggcgtct cgcatatctc attaaagcag gactctagac tgcagtcaga gctggaggga   7380
ggaggattcg agcttgcgcg ggagggcgat gtgctccttg agggacagct cgtcgaggcg    7440
cttccagccg tcgatggtga ggaagcggtg gttggcggtg gccttgatgg tcctgccgag    7500
gcgggtcttg aggatataga cgagcttctt gccggtgcag aacacgcggg acaccttggc    7560
ggactccagc ttcatggtct gctcgttgat ggcccaaatc tcgaagtcct tctcgtcgag    7620
gaggtccttg atggacacgc gcttgccggt ggaggcgagg gagatgaggg agtcgccgga    7680
gatgcagccg gactccctcc agccgagggc ctgggcctcg gacttggtga tgtagttgtc    7740
cgggagcttg tggtaggtct ggaggtagtc ggccacgccg tcgaaggtgt taatcacttg    7800
ggccatatcg atgcttaatt agctttggtt aattggagtg atgggagtgt gtgtagatga    7860
ggctaattgc ttgtgtctat ttataatggc tgtgattagg acttttgcta gctaagagtg    7920
```

```
ttctaagctg ttgtagtgaa gtttgagctg gatcaaacat gaaaatggtg tgaatgatca    7980
gaaaagtttg taattagcaa tgcttaattt ccactgtttt tgttttgctg ttatgtcttc    8040
ctgttttttt tttctgtgcc tgccctgacc aaatttatta agattgagag aaggtaaaac    8100
attttcaaca aatatactcc ctccgttcct aaatatttga taccattgac tttttagcac    8160
atatttaacc gttcgtcata ttcaaaaact tttgtgaaat atgtaaaact atatgtatac    8220
atataagtat atttaacaat aaatcaaatg atagaaaaat aattaataat tacttaaatt    8280
tttttaaata agatgaacat tcaaacatat ttaaaaaaaa atcaatggcg tcaaatattt    8340
agaaactgat ggagtagtta ttaatattac atctcttcct atggataaac agcactttac    8400
atcgaacaaa tggaagcata cacgccgggt tggctgccgg cattgcaatt aaagttattt    8460
cttcagtttg agatatttgt aaatgttaat ttgcaggaac taattaaata agttgttgg     8520
agcttctaga atgtagatta attgtggcta tgtgatcgaa atattctcta cgaaatcgat    8580
ctaaaatgtg gtgcatgcat tgtgcgtgtg tgctgattta agggattgta tcgtgggagc    8640
acaaaacaaa tgccgttcgt tggtttcgct acaacccaac ttaatttgca tctattaaga    8700
tagtgaccaa cctaaactga ttaactgcca tcattgtttt tatatgatac ctttattgtg    8760
gattttttt tttgccgcgc cgggacaaag atgcaagcgg aattttgtaa aaagaaattt     8820
gaactgaacc aaggcggcac aacaattata gtgttatcga aagatgtatg ttccctccgt    8880
tacaaaataa gctaatcttg tacagtgtag gtaacattga agatgtattc acaccgtacg    8940
agtttggttt attttttggac aaagagacga gtaggtaaca acatttcaga aattttagtg   9000
actgacccgt agtgtcactc agtgtatttg gagctcattt gtgtggcaaa acatttccg     9060
aatgattcag ggtttttaacc cttgtgacca ctcttcaatc caagtgcaaa gacaatagaa   9120
aggtggctgg tatgggtgta cctattcagt gatcgtctgt cacctttatt tctagtggac    9180
gaccctttca ttggatgcca tgtgtcatgg ctaaaatatt gaactgtcat ttaaattatt    9240
aagtattaaa cttctgttaa ttggaaatat actgaggccc cgtttggcta atgggaaagg    9300
aaaatcattt cccacccact aaaagacatc tttaaatctt aacctttat tctccttctt     9360
ccatttaatc ctaacccttc atttatttcc caatcccaat tccaccacat atttcccatt    9420
gtccaaatac aacctgaggg ttttaaccaa aattcacttt gaactgtgta aaaaaaggc     9480
gccgaattcc ctacgccccc aactgagaga actcaaaggt tacccagtt ggggcacaga     9540
tctgtcgagt agcttagatc agattgtcgt ttcccgcctt cagtttaaac tatcagtgtt    9600
tgacaggata tattggcggg taaacctaag agaaaagagc gtttattaga ataatcggat    9660
atttaaaagg gcgtgaaaag gtttatccgt tcgtccattt gtatgtgcat gccaaccaca    9720
gggttcccca gatcaggcgc tggctgctga acccccagcc ggaactgacc ccacaaggcc    9780
ctagcgtttg caatgcacca ggtcatcatt gacccaggcg tgttccacca ggccgctgcc    9840
tcgcaactct tcgcaggctt cgccgacctg ctcgcgccac ttcttcacgc gggtggaatc    9900
cgatccgcac atgaggcgga aggtttccag cttgagcggg tacggctccc ggtgcgagct    9960
gaaatagtcg aacatccgtc gggccgtcgg cgacagcttg cggtacttct cccatatgaa    10020
tttcgtgtag tggtcgccag caaacagcac gacgatttcc tcgtcgatca ggacctggca    10080
acgggacgtt ttcttgccac ggtccaggac gcggaagcgg tgcagcagcg acaccgattc    10140
caggtgccca acgcggtcgg acgtgaagcc catcgccgtc gcctgtaggc gcgacaggca    10200
ttcctcggcc ttcgtgtaat accggccatt gatcgaccag cccaggtcct ggcaaagctc    10260
```

```
gtagaacgtg aaggtgatcg gctcgccgat aggggtgcgc ttcgcgtact ccaacacctg   10320
ctgccacacc agttcgtcat cgtcggcccg cagctcgacg ccgtgtagg tgatcttcac    10380 gtccttgttg acgtggaaaa tgaccttgtt ttgcagcgcc tcgcgcggga ttttcttgtt   10440
gcgcgtggtg aacagggcag agcgggccgt gtcgtttggc atcgctcgca tcgtgtccgg   10500
ccacggcgca atatcgaaca aggaaagctg catttccttg atctgctgct tcgtgtgttt   10560
cagcaacgcg gcctgcttgg cctcgctgac ctgttttgcc aggtcctcgc cggcggtttt   10620
tcgcttcttg gtcgtcatag ttcctcgcgt gtcgatggtc atcgacttcg ccaaacctgc   10680
cgcctcctgt tcgagacgac gcgaacgctc cacggcggcc gatggcgcgg gcagggcagg   10740
gggagccagt tgcacgctgt cgcgctcgat cttggccgta gcttgctgga ccatcgagcc   10800
gacggactgg aaggtttcgc ggggcgcacg catgacggtg cggcttgcga tggtttcggc   10860
atcctcggcg gaaaaccccg cgtcgatcag ttcttgcctg tatgccttcc ggtcaaacgt   10920
ccgattcatt caccctcctt gcgggattgc cccgactcac gccggggcaa tgtgcccta    10980 ttcctgattt gacccgcctg gtgccttggt gtccagataa tccaccttat cggcaatgaa   11040
gtcggtcccg tagaccgtct ggccgtcctt ctcgtacttg gtattccgaa tcttgccctg   11100
cacgaatacc agcgacccct tgcccaaata cttgccgtgg gcctcggcct gagagccaaa   11160
acacttgatg cggaagaagt cggtgcgctc ctgcttgtcg ccggcatcgt tgcgccacat   11220
ctaggatctg ccaggaaccg taaaaaggcc gcgttgctgg cgttttcca taggctccgc    11280 cccctgacg agcatcacaa aaatcgacgc tcaagtcaga ggtggcgaaa cccgacagga    11340
ctataaagat accaggcgtt tccccctgga agctccctcg tgcgctctcc tgttccgacc   11400
ctgccgctta ccggatacct gtccgccttt ctcccttcgg aagcgtggc gctttctcat    11460 agctcacgct gtaggtatct cagttcgtg taggtcgttc gctccaagct gggctgtgtg    11520
cacgaacccc ccgttcagcc cgaccgctgc gccttatccg gtaactatcg tcttgagtcc   11580
aacccggtaa gacacgactt atcgccactg gcagcagcca ctggtaacag gattagcaga   11640
gcgaggtatg taggcggtgc tacagagttc ttgaagtggt ggcctaacta cggctacact   11700
agaaggacag tatttggtat ctgcgctctg ctgaagccag ttaccttcgg aaaaagagtt   11760
ggtagctctt gatccggcaa acaaaccacc gctggtagcg gtggtttttt tgtttgcaag   11820
cagcagatta cgcgcagaaa aaaaggatct caagaagatc ctttgatctt ttctacgggg   11880
tctgacgctc agtggaacga aaactcacgt taagggattt tggtcatgag attatcaaaa   11940
aggatcttca cctagatcct tttaaattaa aaatgaagtt ttaaatcaat ctaaagtata   12000
tatgagtaaa cttggtctga cagctaaaac aattcatcca gtaaatata atatttatt     12060 ttctcccaat caggcttgat ccccagtaag tcaaaaaata gctcgacata ctgttcttcc   12120
ccgatatcct ccctgatcga ccggacgcag aaggcaatgt cataccactt gtccgccctg   12180
ccgcttctcc caagatcaat aaagccactt actttgccat cttttcacaaa gatgttgctg   12240 tctcccaggt cgccgtggga aaagacaagt tcctcttcgg gcttttccgt ctttaaaaaa   12300
tcatacagct cgcgcggatc tttaaatgga gtgtcttctt cccagttttc gcaatccaca   12360
tcggccagat cgttattcag taagtaatcc aattcggcta agcggctgtc taagctattc   12420
gtatagggac aatccgatat gtcgatggag tgaaagagcc tgatgcactc cgcatacagc   12480
tcgataatct tttcagggct ttgttcatct tcatactctt ccgagcaaag gacgccatcg   12540
gcctcactca tgagcagatt gctccagcca tcatgccgtt caaagtgcag gacctttgga   12600
acaggcagct ttccttccag ccatagcatc atgtcctttt cccgttccac atcataggtg   12660
```

```
gtcccttat    accggctgtc   cgtcatttt    aaatataggt   tttcatttc    tcccaccagc    12720 ttatatacct   tagcaggaga   cattccttcc   gtatctttta   cgcagcggta   tttttcgatc    12780
agttttttca   attccggtga   tattctcatt   ttagccatac   tcttccttt    tcaatattat    12840 tgaagcattt   atcagggtta   ttgtctcatg   agcggataca   tatttgaatg   tatttagaaa    12900
aataaacaaa   taggggttcc   gcgcacgaat   tggccagcgc   tgccatttt    ggggtgaggc    12960 cgttcgcggc   cgaggggcgc   agcccctggg   gggatgggag   gcccgcgtta   gcggggccggg   13020 agggttcgag   aaggggggc    accccccttc   ggcgtgcgcg   gtcacgcgca   cagggcgcag    13080
ccctggttaa   aaacaaggtt   tataaatatt   ggtttaaaag   caggttaaaa   gacaggttag    13140
cggtggccga   aaaacgggcg   gaaacccttg   caaatgctgg   attttctgcc   tgtggacagc    13200
ccctcaaatg   tcaataggtg   cgcccctcat   ctgtcagcac   tctgcccctc   aagtgtcaag    13260
gatcgcgccc   ctcatctgtc   agtagtcgcg   cccctcaagt   gtcaataccg   cagggcactt    13320
atccccaggc   ttgtccacat   catctgtggg   aaactcgcgt   aaaatcaggc   gttttcgccg    13380
atttgcgagg   ctggccagct   ccacgtcgcc   ggccgaaatc   gagcctgccc   ctcatctgtc    13440
aacgccgcgc   cgggtgagtc   ggcccctcaa   gtgtcaacgt   ccgcccctca   tctgtcagtg    13500
agggccaagt   tttccgcgag   gtatccacaa   cgccggcggc   cgcggtgtct   cgcacacggc    13560
ttcgacggcg   tttctggcgc   gtttgcaggg   ccatagacgg   ccgccagccc   agcggcgagg    13620
gcaaccagcc   cggtgagcgt   cgcaaaggag   atcctgatct   gactgatggg   ctgcctgtat    13680
cgagtggtga   ttttgtgccg   agctgccggt   cggggagctg   ttggctggct   ggtggcagga    13740
tatattgtgg   tgtaaacaaa   ttgacgctta   gacaacttaa   taacacattg   cggacgtttt    13800
taatgtactg   gggtggatgc   actctagcgg   gcc                                     13833
```

<210> SEQ ID NO 46
<211> LENGTH: 13863
<212> TYPE: DNA
<213> ORGANISM: Artificial
<220> FEATURE:
<221> NAME/KEY: misc_feature
<222> LOCATION: (1)..(13863)
<223> OTHER INFORMATION: complete sequence of vector pICH25301

<400> SEQUENCE: 46

```
cacaactagt   gatgggtgag   gtggagtacg   cgcccgggga   gcccaagggc   acgccctggc     60
acccgcaccg   cggcttcgag   ctcgagtgca   ggtcgatcta   gtaacataga   tgacaccgcg    120
cgcgataatt   tatcctagtt   tgcgcgctat   attttgtttt   ctatcgcgta   ttaaatgtat    180
aattgcggga   ctctaatcat   aaaaacccat   ctcataaata   acgtcatgca   ttacatgtta    240
attattacat   gcttaacgta   attcaacaga   aattatatga   taatcatcgc   aagaccggca    300
acaggattca   atcttaagaa   actttattgc   caaatgtttg   aacgatctgc   ttgactctag    360
agcttagcat   tagtacacag   tcctgccatc   accatccagg   atcatgtcct   tgaatgcgcc    420
cccacttggg   atcataggca   gcacatgctc   ctggtgcggg   acgatgatat   ccaacaagta    480
tggccctgga   gtctcgagca   tcttcttgat   ggcggcacgg   acttcactct   tctttgttac    540
acggactgca   ggaatattga   acccttagc    aatagtcaca   aaatctggat   atatctcgct    600
ctcacattcc   gggttgccca   agtatgtatg   cgccctattc   gccttgtaaa   acctatcctc    660
aagttgcacc   accatacca   aatgttggtt   gttcaacacc   atcaccttca   cagggaggtt    720
ctcaatgcgg   atcaatgcca   gctcctgaat   gttcatgagg   aagctaccat   ccccatcaat    780
```

```
atcaacaact gtgacacctg ggttagccac agaagcacca gctgcagcag gcagcccaaa    840
tcccattgcg cccagaccag ccgaagacag ccactgccgt ggccgcttgt aggtgtaata    900
ttgtgccgcc cacatctggt gctgcccaac accagtagcg atgattgcct cacctttcgt    960
cagctcatcc agcacctgaa tggcatattg cggtgggatc tcttcaccaa aagttttgta   1020
ccccagagga aactccctct tctgctggtc caactcattg tgccatgcac taaaatcaga   1080
acttgtcttt gttgtgctct gttgtagcag agcattcaag ccctgtaaag caagcttaac   1140
atctgcgcaa attgacacat gtggttgctt gttctttcca atctctgctg gatcaatgtc   1200
aatgtgcaca atcttggccc tgcttgcaaa agcctcaatt ttccctgtca cacgatcatc   1260
aaaccgcaca ccaaacgcaa gcaacaggtc agccttatcc acggcataat ttgcgtacac   1320
cgtgccatgc atcccaagca tgcgcaggga caacgggtcg tcactgggga aattgccgag   1380
gcccatcaga gtggttgtaa ctgggatacc agtcagctca acaaaccagc gcaattcgtc   1440
accagatgca gagcagccac caccgacata gagaatcggg cgccgtgact cgccaaccag   1500
acgcaagacc tgctcaagca attctgtcgc gggtggcttg gcaggcgtg cgatgtaccc    1560
tggtagattc atcgaggtgt cccagaccgg cacggccatc tgctgctgga tgtccttggg   1620
gatgtcgacc agcaccgggc caggacggcc cgaggacgcg aggaagaagg cttcctgtat   1680
gacgcggggg atgtcctcca catcaaggac aaggtaattg tgcttggtga tggagcgggt   1740
gacctcgact atgggcgtct cctggaaggc gtcggtgccg atcatgcggc gggggacctg   1800
gcccgtgatg cgaccatcg ggacggagtc gagcagcgcg tcggcgagcg cggacacgag    1860
gttggttgcc ccggggccgg aggtggcgac gcagaccccg acgcggccgg acgcgcgcgc   1920
gtacccggac gccgcgaacg cctcgccctg ctcgtggcgg aagaggtggt tggtgatgac   1980
cggggagcgc gtcagcgcct ggtggatctc catggacgcg ccgcccgggt aggcgaacac   2040
gtcgctgacg ccgcaccgct ccagcgcctc cacgaggatg tccgcgccct gcggggctc    2100
ggccggcccc cacggccgga gcggcgtggc cggcggcgcc ggggacggcg gggtgaccgg   2160
ggacaccgcc gagcacctga ccgccgccgc ccccacccgg cctcgagcgg aaggacgtg    2220
gtgtcgctgg tggttcttac ggccggtctt ggccgtcgcg gcggcggaca gggcggcggc   2280
cgcggccgcg gcggtcgtag ccatggttta tcgatagctt atcgtctacc tacaaaaaag   2340
ctccgcacga ggctgcattt gtcacaaatc atgaaaagaa aaactaccga tgaacaatgc   2400
tgagggattc aaattctacc cacaaaaaga agaaagaaag atctagcaca tctaagcctg   2460
acgaagcagc agaaatatat aaaaatataa accatagtgc ccttttcccc tcttcctgat   2520
cttgtttagc atggcggaaa ttttaaaccc cccatcatct cccccaacaa cggcggatcg   2580
cagatctaca tccgagagcc ccattccccg cgagatccgg gccggatcca cgccggcgag   2640
agccccagcc gcgagatccc gcccctcccg cgcaccgatc tgggcgcgca cgaagccgcc   2700
tctcgcccac ccaaactacc aaggccaaag atcgagaccg agacggaaaa aaaaaacgga   2760
gaaagaaaga ggagagggc ggggtggtta ccggcgcggc ggcggcggag ggggaggggg    2820
gaggagctcg tcgtccggca gcgagggggg aggaggtgga ggtggtggtg gtggtggtgg   2880
tagggttggg gggatgggag gagagggggg ggtatgtata tagtggcgat gggggcgtt    2940
tctttggaag cggagggagg gccggcctcg tcgctggctc gcgatcctcc tcgcgtttcc   3000
ggcccccacg acccgacccc acctgctgtt ttttctttt cttttttttc tttcttttt    3060
tttttttggc tgcgagacgt gcggtgcgtg cggacaactc acggtgatag tggggggtg    3120
tggagactat tgtccagttg gctggactgg ggtgggttgg gttggttgg gttgggctgg    3180
```

```
gcttgctatg gatcgtggat agcactttgg gctttaggaa ctttaggggt tgttttttgta   3240 aatgttttga gtctaagttt atcttttatt tttactagaa aaaataccca tgcgctgcaa   3300
cgggggaaag ctattttaat cttattattg ttcattgtga gaattcgcct gaatatatat   3360
ttttctcaaa aattatgtca aattagcata tgggtttttt taaagatatt tcttatacaa   3420
atccctctgt atttacaaaa gcaaacgaac ttaaaacccg actcaaatac agatatgcat   3480
ttccaaaagc gaataaactt aaaaaccaat tcatacaaaa atgacgtatc aaagtaccga   3540
caaaaacatc ctcaattttt ataatagtag aaaagagtaa atttcacttt gggccacctt   3600
ttattaccga tattttactt tataccacct tttaactgat gttttcactt ttgaccaggt   3660
aatcttacct ttgttttatt ttggactatc ccgactctct tctcaagcat atgaatgacc   3720
tcgaccggca tgcagatctg gcgcgccatg caggtcctgc tgagcctcga catgttgtcg   3780
caaaattcgc cctggacccg cccaacgatt tgtcgtcact gtcaaggttt gacctgcact   3840
tcatttggca catacaccaa aaaatgctg cataattctc ggggcagcaa gtcggttacc   3900
cggccgccgt gctggaccgg gttgaatggt gcccgtaact ttcggtagag cggacggcca   3960
atactcaact tcaaggaatc tcacccatgc gcgccggcgg ggaaccggag ttcccttcag   4020
tgagcgttat tagttcgccg ctcggtgtgt cgtagatact agcccctggg gcacttttga   4080
aatttgaata agatttatgt aatcagtctt ttaggtttga ccggttctgc cgcttttttt   4140
aaaattggat ttgtaataat aaaacgcaat tgtttgttat tgtggcgctc tatcatagat   4200
gtcgctataa acctattcag cacaatatat tgttttcatt ttaatattgt acatataagt   4260
agtagggtac aatcagtaaa ttgaacggag aatattattc ataaaaatac gatagtaacg   4320
ggtgatatat tcattagaat gaaccgaaac cggcggtaag gatctgagct acacatgctc   4380 aggttttta caacgtgcac aacagaattg aaagcaaata tcatgcgatc ataggcgtct   4440
cgcatatctc attaaagcag gactctagac tgcagtcaga gctggaggga ggaggattcg   4500
agcttgcgcg ggagggcgat gtgctccttg agggacagct cgtcgaggcg cttccagccg   4560
tcgatggtga ggaagcggtg gttggcggtg gccttgatgg tcctgccgag gcgggtcttg   4620
aggatataga cgagcttctt gccggtgcag aacacgcggg acaccttggc ggactccagc   4680
ttcatggtct gctcgttgat ggcccaaatc tcgaagtcct tctcgtcgag gaggtccttg   4740
atggacacgc gcttgccggt ggaggcgagg gagatgaggg agtcgccgga gatgcagccg   4800
gactccctcc agccgagggc ctgggcctcg gacttggtga tgtagttgtc cgggagcttg   4860
tggtaggtct ggaggtagtc ggccacgccg tcgaaggtgt taatcacttg gccatatcg   4920 atgcttaatt agctttggtt aattggagtg atgggagtgt gtgtagatga ggctaattgc   4980
ttgtgtctat ttataatggc tgtgattagg acttttgcta gctaagagtg ttctaagctg   5040
ttgtagtgaa gtttgagctg gatcaaacat gaaaatggtg tgaatgatca gaaaagtttg   5100
taattagcaa tgcttaattt ccactgtttt tgttttgctg ttatgtcttc ctgtttttt   5160 tttctgtgcc tgccctgacc aaatttatta agattgagag aaggtaaaac attttcaaca   5220
aatatactcc ctccgtttct aaatatttga taccattgac ttttttagcac atatttaacc   5280 gttcgtcata ttcaaaaact tttgtgaaat atgtaaaact atatgtatac atataagtat   5340
atttaacaat aaatcaaatg atagaaaaat aattaataat tacttaaatt tttttaaata   5400
agatgaacat tcaaacatat ttaaaaaaaa atcaatggcg tcaaatattt agaaactgat   5460
ggagtagtta ttaatattac atctcttcct atggataaac agcactttac atcgaacaaa   5520
```

```
tggaagcata cacgccgggt tggctgccgg cattgcaatt aaagttattt cttcagtttg    5580
agatatttgt aaatgttaat ttgcaggaac taattaaata agtttgttgg agcttctaga    5640
atgtagatta attgtggcta tgtgatcgaa atattctcta cgaaatcgat ctaaaatgtg    5700
gtgcatgcat tgtgcgtgtg tgctgattta agggattgta tcgtgggagc acaaaacaaa    5760
tgccgttcgt tggtttcgct acaacccaac ttaatttgca tctattaaga tagtgaccaa    5820
cctaaactga ttaactgcca tcattgtttt tatatgatac ctttattgtg gattttttt     5880 tttgccgcgc cgggacaaag atgcaagcgg aattttgtaa aaagaaattt gaactgaacc    5940
aaggcggcac aacaattata gtgttatcga aagatgtatg ttccctccgt tacaaaataa    6000
gctaatcttg tacagtgtag gtaacattga agatgtattc acaccgtacg agtttggttt    6060 attttttggac aaagagacga gtaggtaaca acatttcaga aatttagtg actgacccgt    6120 agtgtcactc agtgtatttg gagctcattt gtgtggcaaa aacatttccg aatgattcag    6180
ggttttaacc cttgtgacca ctcttcaatc caagtgcaaa gacaatagaa aggtggctgg    6240
tatgggtgta cctattcagt gatcgtctgt caccttatt tctagtggac gacccttca     6300 ttggatgcca tgtgtcatgg ctaaaatatt gaactgtcat ttaaattatt aagtattaaa    6360
cttctgttaa ttggaaatat actgaggccc cgtttggcta atgggaaagg aaaatcattt    6420
cccacccact aaaagacatc tttaaatctt aaccttttat tctccttctt ccatttaatc    6480
ctaacccttc atttatttcc caatcccaat tccaccacat atttcccatt gtccaaatac    6540
aacctgaggg ttttaaccaa aattcacttt gaactgtgta aaaaaaggc gccgaattcc     6600 ctacgccccc aactgagaga actcaaaggt taccccagtt ggggcacaga tctgtcgagt    6660
agcttagatc agattgtcgt ttcccgcctt cagtttaaac tatcagtgtt tgacaggata    6720
tattggcggg taaacctaag agaaaagagc gtttattaga ataatcggat atttaaaagg    6780
gcgtgaaaag gtttatccgt tcgtccattt gtatgtgcat gccaaccaca gggttcccca    6840
gatcaggcgc tggctgctga acccccagcc ggaactgacc ccacaaggcc ctagcgtttg    6900
caatgcacca ggtcatcatt gacccaggcg tgttccacca ggccgctgcc tcgcaactct    6960
tcgcaggctt cgccgacctg ctcgcgccac ttcttcacgc gggtggaatc cgatccgcac    7020
atgaggcgga aggtttccag cttgagcggg tacggctccc ggtgcgagct gaaatagtcg    7080
aacatccgtc gggccgtcgg cgacagcttg cggtacttct cccatatgaa tttcgtgtag    7140
tggtcgccag caaacagcac gacgatttcc tcgtcgatca ggacctggca acgggacgtt    7200
ttcttgccac ggtccaggac gcggaagcgg tgcagcagcg acaccgattc caggtgccca    7260
acgcggtcgg acgtgaagcc catcgccgtc gcctgtaggc gcgacaggca ttcctcggcc    7320
ttcgtgtaat accggccatt gatcgaccag cccaggtcct ggcaaagctc gtagaacgtg    7380
aaggtgatcg gctcgccgat aggggtgcgc ttcgcgtact ccaacacctg ctgccacacc    7440
agttcgtcat cgtcggcccg cagctcgacg ccggtgtagg tgatcttcac gtccttgttg    7500
acgtggaaaa tgaccttgtt ttgcagcgcc tcgcgcggga ttttcttgtt gcgcgtggtg    7560
aacagggcag agcgggccgt gtcgtttggc atcgctcgca tcgtgtccgg ccacggcgca    7620
atatcgaaca aggaaagctg catttccttg atctgctgct tcgtgtgttt cagcaacgcg    7680
gcctgcttgg cctcgctgac ctgttttgcc aggtcctcgc cggcggtttt tcgcttcttg    7740
gtcgtcatag ttcctcgcgt gtcgatggtc atcgacttcg ccaaacctgc cgcctcctgt    7800
tcgagacgac gcgaacgctc cacggcgcc gatggcgcgg gcagggcagg gggagccagt     7860
tgcacgctgt cgcgctcgat cttggccgta gcttgctgga ccatcgagcc gacggactgg    7920
```

```
aaggtttcgc ggggcgcacg catgacggtg cggcttgcga tggtttcggc atcctcggcg    7980
gaaaacccccg cgtcgatcag ttcttgcctg tatgccttcc ggtcaaacgt ccgattcatt    8040
caccctcctt gcgggattgc cccgactcac gccggggcaa tgtgcccctta ttcctgattt    8100
gacccgcctg gtgccttggt gtccagataa tccaccttat cggcaatgaa gtcggtcccg    8160
tagaccgtct ggccgtcctt ctcgtacttg gtattccgaa tcttgccctg cacgaatacc    8220
agcgacccct tgcccaaata cttgccgtgg gcctcggcct gagagccaaa acacttgatg    8280
cggaagaagt cggtgcgctc ctgcttgtcg ccggcatcgt tgcgccacat ctaggatctg    8340
ccaggaaccg taaaaaggcc gcgttgctgg cgttttttcca taggctccgc cccctgacg    8400
agcatcacaa aaatcgacgc tcaagtcaga ggtggcgaaa cccgacagga ctataaagat    8460
accaggcgtt tccccctgga agctccctcg tgcgctctcc tgttccgacc ctgccgctta    8520
ccggatacct gtccgccttt ctcccttcgg gaagcgtggc gctttctcat agctcacgct    8580
gtaggtatct cagttcggtg taggtcgttc gctccaagct gggctgtgtg cacgaacccc    8640
ccgttcagcc cgaccgctgc gccttatccg gtaactatcg tcttgagtcc aacccggtaa    8700
gacacgactt atcgccactg gcagcagcca ctggtaacag gattagcaga gcgaggtatg    8760
taggcggtgc tacagagttc ttgaagtggt ggcctaacta cggctacact agaaggacag    8820
tatttggtat ctgcgctctg ctgaagccag ttaccttcgg aaaaagagtt ggtagctctt    8880
gatccggcaa acaaaccacc gctggtagcg gtggtttttt tgtttgcaag cagcagatta    8940
cgcgcagaaa aaaaggatct caagaagatc ctttgatctt ttctacgggg tctgacgctc    9000
agtggaacga aaactcacgt taagggattt tggtcatgag attatcaaaa aggatcttca    9060
cctagatcct tttaaattaa aaatgaagtt ttaaatcaat ctaaagtata tatgagtaaa    9120
cttggtctga cagctaaaac aattcatcca gtaaaatata atatttttatt ttctcccaat    9180
caggcttgat ccccagtaag tcaaaaaata gctcgacata ctgttcttcc ccgatatcct    9240
ccctgatcga ccggacgcag aaggcaatgt cataccactt gtccgccctg ccgcttctcc    9300
caagatcaat aaaagccactt actttgccat cttttcacaaa gatgttgctg tctcccaggt    9360
cgccgtggga aaagacaagt tcctcttcgg gcttttccgt ctttaaaaaa tcatacagct    9420
cgcgcggatc tttaaatgga gtgtcttctt cccagttttc gcaatccaca tcggccagat    9480
cgttattcag taagtaatcc aattcggcta agcggctgtc taagctattc gtataggac    9540
aatccgatat gtcgatggag tgaaagagcc tgatgcactc cgcatacagc tcgataatct    9600
tttcagggct ttgttcatct tcatactctt ccgagcaaag gacgccatcg gcctcactca    9660
tgagcagatt gctccagcca tcatgccgtt caaagtgcag gacctttgga acaggcagct    9720
ttccttccag ccatagcatc atgtcctttt cccgttccac atcataggtg gtccctttat    9780
accggctgtc cgtcattttt aaatataggt tttcattttc tcccaccagc ttatatacct    9840
tagcaggaga cattccttcc gtatcttttta cgcagcggta ttttttcgatc agttttttca    9900
attccggtga tattctcatt ttagccatac tcttcctttt tcaatattat tgaagcattt    9960
atcagggtta ttgtctcatg agcggataca tatttgaatg tatttagaaa aataaacaaa   10020
tagggggttcc gcgcacgaat tggccagcgc tgccattttt ggggtgaggc cgttcgcggc   10080
cgaggggcgc agcccctggg gggatgggag gcccgcgtta gcgggccggg agggttcgag   10140
aagggggggc accccccttc ggcgtgcgcg gtcacgcgca cagggcgcag ccctggttaa   10200
aaacaaggtt tataaatatt ggtttaaaag caggttaaaa gacaggttag cggtggccga   10260
```

```
aaaacgggcg gaaacccttg caaatgctgg attttctgcc tgtggacagc ccctcaaatg    10320
tcaataggtg cgcccctcat ctgtcagcac tctgccnctc aagtgtcaag gatcgcgccc    10380
ctcatctgtc agtagtcgcg cccctcaagt gtcaataccg cagggcactt atccccaggc    10440
ttgtccacat catctgtggg aaactcgcgt aaaatcaggc gttttcgccg atttgcgagg    10500
ctggccagct ccacgtcgcc ggccgaaatc gagcctgccc ctcatctgtc aacgccgcgc    10560
cgggtgagtc ggcccctcaa gtgtcaacgt ccgcccctca tctgtcagtg agggccaagt    10620
tttccgcgag gtatccacaa cgccggcggc cgcggtgtct cgcacacggc ttcgacggcg    10680
tttctgcgcg ctttgcaggg ccatagacgg ccgccagccc agcggcgagg caaccagcc    10740 cggtgagcgt cgcaaaggag atcctgatct gactgatggg ctgcctgtat cgagtggtga    10800
ttttgtgccg agctgccggt cggggagctg ttggctggct ggtggcagga tatattgtgg    10860
tgtaaacaaa ttgacgctta gacaacttaa taacacattg cggacgtttt taatgtactg    10920
gggtggatgc actctagcgg gccctacgcc cccaactgag agaactcaaa ggttacccca    10980
gttggggcac ggcgcgccac actcgagaat tcggcgcctt ttttttacac agttcaaagt    11040
gaattttggt taaaaccctc aggttgtatt tggataatgg ggaataatgt gggtgggaat    11100
tgggattggg aaatgaacga agggttagga ttaaatggaa gaaggagaat aaatggttaa    11160
aatttaaaga tgtctttttag tgggtgggaa atgatttccc tttcccatta gccaaacggg    11220
gcctcagtat attttcaatt aacagaagtt taatacttaa taatttaaat gacagttcaa    11280
tattttagcc atgacacatg gcatccaatg aaagggtcgt ccactagaaa taaaggtgac    11340
agacggtcac tgaataggta cacccatacc agccaccttt ctattgtctt tgcacttggg    11400
attgaaaagg tggtcaccaa ggggttaaaa ccctgtattc attcgggaaa tgttttgcc    11460 acacaaatga gttccaaata cactgagtga cactacgggt cagtccctaa aatttctgaa    11520
atgttgttac ctacccgtct ctttgtccaa aaataaacca aacccgtacg gtgtgaatat    11580
accttcaatg ttacctacac tgtacaaggt tagcttattt tgtaacggag gaacataca    11640 tctttccgat acccagcatt aataattgtt gtgccgcctt ggttcagttc aaatttcttt    11700
ttacaaaatt ccgcttgcat cttttgtcccg gcgcggcaaa aaaaaaatcc acaataaagg    11760
tatcatataa aaacaatgat ggcagttaat cagtttaggt tggtcactat cttaatagat    11820
gcaaattaag ttgggttgta gcgaaaccaa cgaacggcat ttgttttgtg ctcccacgat    11880
acaatccctt aaatcagcac acacgcacaa tgcatgcacc acattttaga tcgatttcgt    11940
agagaatatt tcgatcacat agccacaatt aatctacatt ctagaagctc aacaaaactt    12000
atttaattag ttcctgcaaa ttaacattta caaatatctc aaactgaaga aataacttta    12060
attgcaatgc cggcagccaa cccggcgtgt atgcttccat ttgttcggat gtaaaaggtg    12120
ctgtttatcc ataggaagag gtgtaatatt aataactact ccatccgttt ctaaatattt    12180
gacgtcattg actatttgtt taaatatgtt tgaatgttcg tcttatttta aaaaatta    12240 agtaattatt aattattttc tatcattttg atttattggt taaatatacc ttatatgtat    12300
acatatagtt ttacatattt cacaaaagtt tttgaatatg acgaaaggtt aaacatgtgc    12360
taaaaagtca atggtatcaa atatttagaa acggagggag tatgtttgtt gaaatgtttt    12420
taccttctct caatcttaat aaatttggtc agggcaggca ccggaaaaaa aaaacaggaa    12480
ggcataacag caaaacaaaa acagtggaaa ttaagcattg ctaattacaa acttttctga    12540 tcattccacac cattttcatg tttgatcccg ctcaaacttc acttcaacag cttagacact    12600
cttagctagc aaaagtccta atcacaggca ttataaatgg cacaggcaat tagcctcatc    12660
```

```
tacacacact gccatcactc caattaacca aagctaatta agcatcgatt catgagcccg   12720
gagatcgaga agctctccca gtccgacatc tactgggact ccatcgtgtc catcaccgaa   12780
acgggcgtgg aggaggtgtt cgacctcacc gtgccaggcc cgcacaactt cgtggccaac   12840
gacatcatcg tgcacaactc catcgagcag gacggaggcg gaggaagtgg aggcggtgga   12900
tcagtggcct ccaagggcaa cctcgccgac gtggccccag ggaagtccat cggcggcgac   12960
atcttctcta accgcgaggg caagctccca ggcaagtcgg gcaggacctg gagggaggcc   13020
gacatcaact acacctccgg cttccgcaac tccgaccgca tcctctactc ctccgactgg   13080
ctcatctaca agaccaccga ccactaccag accttcacca agatccgctg aggatcctct   13140
agagtcctgc tttaatgaga tatgcgagac gcctatgatc gcatgatatt tgctttcaat   13200
tctgttgtgc acgttgtaaa aaacctgagc atgtgtagct cagatcctta ccgccggttt   13260
cggttcattc taatgaatat atcacccgtt actatcgtat ttttatgaat aatattctcc   13320
gttcaattta ctgattgtac cctactactt atatgtacaa tattaaaatg aaaacaatat   13380
attgtgctga ataggtttat agcgacatct atgatagagc gccacaataa caaacaattg   13440
cgttttatta ttacaaatcc aatttttaaaa aaagcggcag aaccggtcaa acctaaaaga   13500
ctgattacat aaatcttatt caaatttcaa aagtgcccca ggggctagta tctacgacac   13560
accgagcggc gaactaataa cgctcactga agggaactcc ggttcccgc cggcgcgcat    13620
gggtgagatt ccttgaagtt gagtattggc cgtccgctct accgaaagtt acgggcacca   13680
ttcaacccgg tccagcacgg cggccgggta accgacttgc tgccccgaga attatgcagc   13740
atttttttgg tgtatgtgcc aaatgaagtg caggtcaaac cttgacagtg acgacaaatc   13800
gttgggcggg tccagggcga attttgcgac aacatgtcga ggctcagcag gacctgcagg   13860
tac                                                                 13863
```

<210> SEQ ID NO 47
<211> LENGTH: 13878
<212> TYPE: DNA
<213> ORGANISM: Artificial
<220> FEATURE:
<221> NAME/KEY: misc_feature
<222> LOCATION: (1)..(13878)
<223> OTHER INFORMATION: complete sequence of vector pICH27371

<400> SEQUENCE: 47

```
ctacgccccc aactgagaga actcaaaggt taccccagtt ggggcacggc gcgccacact    60
cgagaattcg gcgcctttt tttacacagt tcaaagtgaa ttttggttaa aaccctcagg    120
ttgtatttgg ataatgggga ataatgtggg tgggaattgg gattgggaaa tgaacgaagg   180
gttaggatta aatggaagaa ggagaataaa tggttaaaat ttaaagatgt cttttagtgg   240
gtgggaaatg atttcccttt cccattagcc aaacggggcc tcagtatatt ttcaattaac   300
agaagtttaa tacttaataa tttaaatgac agttcaatat tttagccatg acacatggca   360
tccaatgaaa gggtcgtcca ctagaaataa aggtgacaga cggtcactga ataggtacac   420
ccataccagc caccttttcta ttgtctttgc acttgggatt gaaaaggtgg tcaccaaggg   480
gttaaaaccc tgtattcatt cgggaaatgt ttttgccaca caaatgagtt ccaaatacac   540
tgagtgacac tacgggtcag tccctaaaat ttctgaaatg ttgttaccta cccgtctctt   600
tgtccaaaaa taaccaaac ccgtacggtg tgaatatacc ttcaatgtta cctacactgt   660
acaaggttag cttatttttgt aacggaggga acatacatct ttccgatacc cagcattaat   720
```

-continued

```
aattgttgtg ccgccttggt tcagttcaaa tttctttta caaaattccg cttgcatctt    780
tgtcccggcg cggcaaaaaa aaatccaca ataaaggtat catataaaaa caatgatggc    840
agttaatcag tttaggttgg tcactatctt aatagatgca aattaagttg ggttgtagcg    900
aaaccaacga acggcatttg ttttgtgctc ccacgataca atcccttaaa tcagcacaca    960
cgcacaatgc atgcaccaca ttttagatcg atttcgtaga gaatatttcg atcacatagc   1020
cacaattaat ctacattcta gaagctccaa caaacttatt taattagttc ctgcaaatta   1080
acatttacaa atatctcaaa ctgaagaaat aactttaatt gcaatgccgg cagccaaccc   1140
ggcgtgtatg cttccatttg ttcggatgta aaaggtgctg tttatccata ggaagaggtg   1200
taatattaat aactactcca tccgtttcta aatatttgac gtcattgact atttgtttaa   1260
atatgtttga atgttcgtct tatttaaaa aaatttaagt aattattaat tattttctat    1320
cattttgatt tattggttaa atatacctta tatgtataca tatagttta catatttcac    1380 aaaagttttt gaatatgacg aaaggttaaa catgtgctaa aaagtcaatg gtatcaaata   1440
tttagaaacg gagggagtat gtttgttgaa aatgtttac cttctctcaa tcttaataaa    1500
tttggtcagg gcaggcaccg gaaaaaaaaa acaggaaggc ataacagcaa aacaaaaaca   1560
gtggaaatta agcattgcta attacaaact tttctgatca ttcacaccat tttcatgttt   1620
gatcccgctc aaacttcact tcaacagctt agacactctt agctagcaaa agtcctaatc   1680
acaggcatta taaatggcac aggcaattag cctcatctac acacactgcc atcactccaa   1740
ttaaccaaag ctaattaagc atcgattcat gagcccggag atcgagaagc tctcccagtc   1800
cgacatctac tgggactcca tcgtgtccat caccgaaacg ggcgtggagg aggtgttcga   1860
cctcaccgtg ccaggcccgc acaacttcgt ggccaacgac atcatcgtgc acaactccat   1920
cgagcaggac ggaggcggtg gaagtggagg cggtggatca ggaggcggtg gctcagtggc   1980
ctccaagggc aacctcgccg acgtggcccc agggaagtcc atcggcggcg acatcttctc   2040
caaccgcgag ggcaagctcc caggcaagtc gggcaggacc tggagggagg ccgacatcaa   2100
ctacacctcc ggcttccgca actccgaccg catcctctac tcctccgact ggctcatcta   2160
caagaccacc gaccactacc agaccttcac caagatccgc tgaggatcct ctagagtcct   2220
gctttaatga gatatgcgag acgcctatga tcgcatgata tttgctttca attctgttgt   2280
gcacgttgta aaaaacctga gcatgtgtag ctcagatcct taccgccggt ttcggttcat   2340
tctaatgaat atatcacccg ttactatcgt attttatga ataatattct ccgttcaatt    2400
tactgattgt accctactac ttatatgtac aatattaaaa tgaaaacaat atattgtgct   2460
gaataggttt atagcgacat ctatgataga gcgccacaat aacaaacaat tgcgttttat   2520
tattacaaat ccaattttaa aaaagcggc agaaccggtc aaacctaaaa gactgattac    2580
ataaatctta ttcaaatttc aaaagtgccc caggggctag tatctacgac acaccgagcg   2640
gcgaactaat aacgctcact gaagggaact ccggttcccc gccggcgcgc atgggtgaga   2700
ttccttgaag ttgagtattg gccgtccgct ctaccgaaag ttacgggcac cattcaaccc   2760
ggtccagcac ggcggccggg taaccgactt gctgccccga gaattatgca gcattttttt   2820
ggtgtatgtg ccaaatgaag tgcaggtcaa accttgacag tgacgacaaa tcgttgggcg   2880
ggtccagggc gaattttgcg acaacatgtc gaggctcagc aggacctgca ggtaccacaa   2940
ctagtgatgg gtgaggtgga gtacgcgccc ggggagccca agggcacgcc ctggcacccg   3000
caccgcggct tcgagctcga gtgcaggtcg atctagtaac atagatgaca ccgcgcgcga   3060
taatttatcc tagtttgcgc gctatatttt gttttctatc gcgtattaaa tgtataattg   3120
```

```
cgggactcta atcataaaaa cccatctcat aaataacgtc atgcattaca tgttaattat    3180
tacatgctta acgtaattca acagaaatta tatgataatc atcgcaagac cggcaacagg    3240
attcaatctt aagaaacttt attgccaaat gtttgaacga tctgcttgac tctagagctt    3300
agcattagta cacagtcctg ccatcaccat ccaggatcat gtccttgaat gcgccccac     3360 ttgggatcat aggcagcaca tgctcctggt gcgggacgat gatatccaac aagtatggcc    3420
ctggagtctc gagcatcttc ttgatggcgg cacggacttc actcttcttt gttacacgga    3480
ctgcaggaat attgaacccc ttagcaatag tcacaaaatc tggatatatc tcgctctcac    3540
attccgggtt gcccaagtat gtatgcgccc tattcgcctt gtaaaaccta tcctcaagtt    3600
gcaccaccat acccaaatgt tggttgttca acaccatcac cttcacaggg aggttctcaa    3660
tgcggatcaa tgccagctcc tgaatgttca tgaggaagct accatcccca tcaatatcaa    3720
caactgtgac acctgggtta gccacagaag caccagctgc agcaggcagc ccaaatccca    3780
ttgcgcccag accagccgaa gacagccact gccgtggccg cttgtaggtg taatattgtg    3840
ccgcccacat ctggtgctgc ccaacaccag tagcgatgat tgcctcacct ttcgtcagct    3900
catccagcac ctgaatggca tattgcggtg ggatctcttc accaaaagtt ttgtacccca    3960
gaggaaactc cctcttctgc tggtccaact cattgtgcca tgcactaaaa tcagaacttg    4020
tctttgttgt gctctgttgt agcagagcat tcaagccctg taaagcaagc ttaacatctg    4080
cgcaaattga cacatgtggt tgcttgttct ttccaatctc tgctggatca atgtcaatgt    4140
gcacaatctt ggccctgctt gcaaaagcct caatttttccc tgtcacacga tcatcaaacc    4200
gcacaccaaa cgcaagcaac aggtcagcct tatccacggc ataatttgcg tacaccgtgc    4260
catgcatccc aagcatgcgc agggacaacg ggtcgtcact ggggaaattg ccgaggccca    4320
tcagagtggt tgtaactggg ataccagtca gctcaacaaa ccagcgcaat tcgtcaccag    4380
atgcagagca gccaccaccg acatagagaa tcgggcgccg tgactcgcca accagacgca    4440
agacctgctc aagcaattct gtcgcgggtg gcttgggcag gcgtgcgatg taccctggta    4500
gattcatcga ggtgtcccag accggcacgg ccatctgctg ctggatgtcc ttggggatgt    4560
cgaccagcac cgggccagga cggcccgagg acgcgaggaa gaaggcttcc tgtatgacgc    4620
gggggatgtc ctccacatca aggacaaggt aattgtgctt ggtgatggag cgggtgacct    4680
cgactatggg cgtctcctgg aaggcgtcgg tgccgatcat gcggcggggg acctggcccg    4740
tgatggcgac catcgggacg gagtcgagca gcgcgtcggc gagcgcggac acgaggttgg    4800 ttgcccccggg gccggaggtg gcgacgcaga ccccgacgcg gccggacgcg cgcgcgtacc    4860
cggacgccgc gaacgcctcg ccctgctcgt ggcggaagag gtggttggtg atgaccgggg    4920
agcgcgtcag cgcctggtgg atctccatgg acgcgccgcc cgggtaggcg aacacgtcgc    4980
tgacgccgca ccgctccagc gcctccacga ggatgtccgc gcccttgcgg ggctcggccg    5040
gcccccacgg ccggagcggc gtggccggcg gcgccgggga cggcggggtg accggggaca    5100
ccgccgagca cctgaccgcc gccgccccca cccggcctcg agcgggaagg acgtggtgtc    5160
gctggtggtt cttacggccg gtcttggccg tcgcggcggc ggacagggcg gcggccgcgg    5220
ccgcggcggt cgtagccatg gtttatcgat agcttatcgt ctacctacaa aaaagctccg    5280
cacgaggctg catttgtcac aaatcatgaa aagaaaaact accgatgaac aatgctgagg    5340
gattcaaatt ctacccacaa aaagaagaaa gaaagatcta gcacatctaa gcctgacgaa    5400
gcagcagaaa tatataaaaa tataaaccat agtgcccttt tcccctcttc ctgatcttgt    5460
```

```
ttagcatggc ggaaatttta aaccccccat catctccccc aacaacggcg gatcgcagat   5520
ctacatccga gagccccatt ccccgcgaga tccgggccgg atccacgccg gcgagagccc   5580
cagccgcgag atcccgcccc tcccgcgcac cgatctgggc gcgcacgaag ccgcctctcg   5640
cccacccaaa ctaccaaggc caaagatcga gaccgagacg gaaaaaaaaa acggagaaag   5700
aaagaggaga ggggcggggt ggttaccggc gcggcggcgg cggaggggga gggggagga   5760 gctcgtcgtc cggcagcgag gggggaggag gtggaggtgg tggtggtggt ggtggtaggg   5820 ttgggggat gggaggagag gggggggtat gtatatagtg gcgatggggg gcgtttcttt   5880
ggaagcggag ggagggccgg cctcgtcgct ggctcgcgat cctcctcgcg tttccggccc   5940
ccacgacccg gacccacctg ctgttttttc ttttctttt tttctttct ttttttttt   6000 ttggctgcga gacgtgcggt gcgtgcgac aactcacggt gatagtgggg gggtgtggag   6060
actattgtcc agttggctgg actggggtgg gttgggttgg gttgggttgg gctgggcttg   6120
ctatggatcg tggatagcac tttgggcttt aggaacttta ggggttgttt ttgtaaatgt   6180
tttgagtcta agtttatctt ttattttac tagaaaaat acccatgcgc tgcaacgggg   6240
gaaagctatt ttaatcttat tattgttcat tgtgagaatt cgcctgaata tatattttc   6300 tcaaaaatta tgtcaaatta gcatatgggt tttttaaag atatttctta tacaaatccc   6360
tctgtattta caaagcaaa cgaacttaaa acccgactca aatacagata tgcatttcca   6420
aaagcgaata aacttaaaaa ccaattcata caaaaatgac gtatcaaagt accgacaaaa   6480
acatcctcaa tttttataat agtagaaaag agtaaatttc actttgggcc acctttatt   6540 accgatattt tactttatac cacctttaa ctgatgtttt cacttttgac caggtaatct   6600
tacctttgtt ttattttgga ctatcccgac tctcttctca agcatatgaa tgacctcgac   6660
cggcatgcag atctggcgcg ccatgcaggt cctgctgagc ctcgacatgt tgtcgcaaaa   6720
ttcgccctgg acccgcccaa cgatttgtcg tcactgtcaa ggtttgacct gcacttcatt   6780
tggcacatac accaaaaaaa tgctgcataa ttctcggggc agcaagtcgg ttacccggcc   6840
gccgtgctgg accgggttga atggtgcccg taactttcgg tagagcggac ggccaatact   6900
caacttcaag gaatctcacc catgcgcgcc ggcggggaac cggagttccc ttcagtgagc   6960
gttattagtt cgccgctcgg tgtgtcgtag atactagccc ctggggcact tttgaaattt   7020
gaataagatt tatgtaatca gtcttttagg tttgaccggt tctgccgctt tttttaaat   7080 tggatttgta ataataaaac gcaattgttt gttattgtgg cgctctatca tagatgtcgc   7140
tataaaccta ttcagcacaa tatattgttt tcattttaat attgtacata taagtagtag   7200
ggtacaatca gtaaattgaa cggagaatat tattcataaa aatacgatag taacgggtga   7260
tatattcatt agaatgaacc gaaaccggcg gtaaggatct gagctacaca tgctcaggtt   7320
ttttacaacg tgcacaacag aattgaaagc aaatatcatg cgatcatagg cgtctcgcat   7380
atctcattaa agcaggactc tagactgcag tcagagctgg agggaggagg attcgagctt   7440
gcgcgggagg gcgatgtgct ccttgaggga cagctcgtcg aggcgcttcc agccgtcgat   7500
ggtgaggaag cggtggttgg cggtggcctt gatggtcctg ccgaggcggg tcttgaggat   7560
atagacgagc ttcttgccgg tgcagaacac gcgggacacc ttgcggact ccagcttcat   7620 ggtctgctcg ttgatggccc aaatctcgaa gtccttctcg tcgaggaggt ccttgatgga   7680
cacgcgcttg ccggtggagg cgagggagat gagggagtcg ccggagatgc agccggactc   7740
cctccagccg agggcctggg cctcggactt ggtgatgtag ttgtccggga gcttgtggta   7800
ggtctggagg tagtcggcca cgccgtcgaa ggtgttaatc acttgggcca tatcgatgct   7860
```

```
taattagctt tggttaattg gagtgatggg agtgtgtgta gatgaggcta attgcttgtg    7920
tctatttata atggctgtga ttaggacttt tgctagctaa gagtgttcta agctgttgta    7980
gtgaagtttg agctggatca aacatgaaaa tggtgtgaat gatcagaaaa gtttgtaatt    8040
agcaatgctt aatttccact gttttttgtt tgctgttatg tcttcctgtt ttttttttct    8100
gtgcctgccc tgaccaaatt tattaagatt gagagaaggt aaaacatttt caacaaatat    8160
actccctccg tttctaaata tttgatacca ttgacttttt agcacatatt taaccgttcg    8220
tcatattcaa aaacttttgt gaaatatgta aaactatatg tatacatata agtatattta    8280
acaataaatc aaatgataga aaaataatta ataattactt aaattttttt aaataagatg    8340
aacattcaaa catatttaaa aaaaaatcaa tggcgtcaaa tatttagaaa ctgatggagt    8400
agttattaat attacatctc ttcctatgga taaacagcac tttacatcga acaaatggaa    8460
gcatacacgc cgggttggct gccggcattg caattaaagt tatttcttca gtttgagata    8520
tttgtaaatg ttaatttgca ggaactaatt aaataagttt gttggagctt ctagaatgta    8580
gattaattgt ggctatgtga tcgaaatatt ctctacgaaa tcgatctaaa atgtggtgca    8640
tgcattgtgc gtgtgtgctg atttaaggga ttgtatcgtg ggagcacaaa acaaatgccg    8700
ttcgttggtt tcgctacaac ccaacttaat ttgcatctat taagatagtg accaacctaa    8760
actgattaac tgccatcatt gttttatat gataccttta ttgtggattt ttttttttgc    8820
cgcgccggga caaagatgca agcggaattt tgtaaaaaga aatttgaact gaaccaaggc    8880
ggcacaacaa ttatagtgtt atcgaaagat gtatgttccc tccgttacaa aataagctaa    8940
tcttgtacag tgtaggtaac attgaagatg tattcacacc gtacgagttt ggtttatttt    9000
tggacaaaga gacgagtagg taacaacatt tcagaaattt tagtgactga cccgtagtgt    9060
cactcagtgt atttggagct catttgtgtg gcaaaaacat ttccgaatga ttcagggttt    9120
taacccttgt gaccactctt caatccaagt gcaaagacaa tagaaaggtg gctggtatgg    9180
gtgtacctat tcagtgatcg tctgtcacct ttatttctag tggacgaccc tttcattgga    9240
tgccatgtgt catggctaaa atattgaact gtcatttaaa ttattaagta ttaaacttct    9300
gttaattgga aatatactga ggccccgttt ggctaatggg aaaggaaaat catttcccac    9360
ccactaaaag acatctttaa atcttaacct tttattctcc ttcttccatt taatcctaac    9420
ccttcattta tttcccaatc ccaattccac cacatatttc ccattgtcca aatacaacct    9480
gagggtttta accaaaattc actttgaact gtgtaaaaaa aaggcgccga attccctacg    9540
cccccaactg agagaactca aaggttaccc cagttggggc acagatctgt cgagtagctt    9600
agatcagatt gtcgtttccc gccttcagtt taaactatca gtgtttgaca ggatatattg    9660
gcgggtaaac ctaagagaaa agagcgttta ttagaataat cggatattta aaagggcgtg    9720
aaaaggttta tccgttcgtc catttgtatg tgcatgccaa ccacagggtt ccccagatca    9780
ggcgctggct gctgaacccc cagccggaac tgacccccaca aggccctagc gtttgcaatg    9840
caccaggtca tcattgaccc aggcgtgttc caccaggccg ctgcctcgca actcttcgca    9900
ggcttcgccg acctgctcgc gccacttctt cacgcgggtg gaatccgatc cgcacatgag    9960
gcggaaggtt tccagcttga gcgggtacgg ctcccggtgc gagctgaaat agtcgaacat   10020
ccgtcgggcc gtcggcgaca gcttgcggta cttctcccat atgaatttcg tgtagtggtc   10080
gccagcaaac agcacgacga tttcctcgtc gatcaggacc tggcaacggg acgttttctt   10140
gccacggtcc aggacgcgga agcggtgcag cagcgacacc gattccaggt gcccaacgcg   10200
```

```
gtcggacgtg aagcccatcg ccgtcgcctg taggcgcgac aggcattcct cggccttcgt   10260
gtaataccgg ccattgatcg accagcccag gtcctggcaa agctcgtaga acgtgaaggt   10320
gatcggctcg ccgatagggg tgcgcttcgc gtactccaac acctgctgcc acaccagttc   10380
gtcatcgtcg gcccgcagct cgacgccggt gtaggtgatc ttcacgtcct tgttgacgtg   10440
gaaaatgacc ttgttttgca gcgcctcgcg cgggattttc ttgttgcgcg tggtgaacag   10500
ggcagagcgg gccgtgtcgt ttggcatcgc tcgcatcgtg tccggccacg cgcaatatc   10560 gaacaaggaa agctgcattt ccttgatctg ctgcttcgtg tgtttcagca acgcggcctg   10620
cttggcctcg ctgacctgtt ttgccaggtc ctcgccggcg ttttttcgct tcttggtcgt   10680
catagttcct cgcgtgtcga tggtcatcga cttcgccaaa cctgccgcct cctgttcgag   10740
acgacgcgaa cgctccacgg cggccgatgg cgcgggcagg gcaggggag ccagttgcac   10800 gctgtcgcgc tcgatcttgg ccgtagcttg ctggaccatc gagccgacgg actggaaggt   10860
ttcgcggggc gcacgcatga cggtgcggct tgcgatggtt tcggcatcct cggcggaaaa   10920
ccccgcgtcg atcagttctt gcctgtatgc cttccggtca acgtccgat tcattcaccc   10980 tccttgcggg attgccccga ctcacgccgg ggcaatgtgc ccttattcct gatttgaccc   11040
gcctggtgcc ttggtgtcca gataatccac cttatcggca atgaagtcgg tcccgtagac   11100
cgtctggccg tccttctcgt acttggtatt ccgaatcttg ccctgcacga ataccagcga   11160
cccccttgcc aaatacttgc cgtgggcctc ggcctgagag ccaaaacact tgatgcgaa   11220 gaagtcggtg cgctcctgct tgtcgccggc atcgttgcgc cacatctagg atctgccagg   11280
aaccgtaaaa aggccgcgtt gctggcgttt ttccataggc tccgccccc tgacgagcat   11340 cacaaaaatc gacgctcaag tcagaggtgg cgaaacccga caggactata aagataccag   11400
gcgtttcccc ctggaagctc cctcgtgcgc tctcctgttc cgaccctgcc gcttaccgga   11460
tacctgtccg cctttctccc ttcgggaagc gtggcgcttt ctcatagctc acgctgtagg   11520
tatctcagtt cggtgtaggt cgttcgctcc aagctgggct gtgtgcacga accccccgtt   11580
cagcccgacc gctgcgcctt atccggtaac tatcgtcttg agtccaaccc ggtaagacac   11640
gacttatcgc cactggcagc agccactggt aacaggatta gcagagcgag gtatgtaggc   11700
ggtgctacag agttcttgaa gtggtggcct aactacggct acactagaag gacagtattt   11760
ggtatctgcg ctctgctgaa gccagttacc ttcggaaaaa gagttggtag ctcttgatcc   11820
ggcaaacaaa ccaccgctgg tagcggtggt ttttttgttt gcaagcagca gattacgcgc   11880
agaaaaaaag gatctcaaga agatcctttg atcttttcta cggggtctga cgctcagtgg   11940
aacgaaaact cacgttaagg gattttggtc atgagattat caaaaggat cttcacctag   12000 atccttttaa attaaaaatg aagttttaaa tcaatctaaa gtatatatga gtaaacttgg   12060
tctgacagct aaaacaattc atccagtaaa atataatatt ttattttctc ccaatcaggc   12120
ttgatcccca gtaagtcaaa aaatagctcg acatactgtt cttccccgat atcctccctg   12180
atcgaccgga cgcagaaggc aatgtcatac cacttgtccg ccctgccgct tctcccaaga   12240
tcaataaagc cacttacttt gccatctttc acaaagatgt tgctgtctcc caggtcgccg   12300
tgggaaagda caagttcctc ttcgggcttt tccgtcttta aaaatcata cagctcgcgc   12360 ggatctttaa atggagtgtc ttcttcccag ttttcgcaat ccacatcggc cagatcgtta   12420
ttcagtaagt aatccaattc ggctaagcgg ctgtctaagc tattcgtata gggacaatcc   12480
gatatgtcga tggagtgaaa gagcctgatg cactccgcat acagtcgat aatcttttca   12540 gggctttgtt catcttcata ctcttccgag caaaggacgc catcggcctc actcatgagc   12600
```

```
agattgctcc agccatcatg ccgttcaaag tgcaggacct ttggaacagg cagcttttcct    12660 tccagccata gcatcatgtc cttttcccgt tccacatcat aggtggtccc tttataccgg    12720
ctgtccgtca tttttaaata taggttttca ttttctccca ccagcttata taccttagca    12780
ggagacattc cttccgtatc ttttacgcag cggtattttt cgatcagttt tttcaattcc    12840
ggtgatattc tcattttagc catactcttc ctttttcaat attattgaag catttatcag    12900
ggttattgtc tcatgagcgg atacatattt gaatgtattt agaaaaataa acaaataggg    12960
gttccgcgca cgaattggcc agcgctgcca ttttgggt gaggccgttc gcggccgagg    13020
ggcgcagccc ctgggggat gggaggcccg cgttagcggg ccgggagggt tcgagaaggg    13080
ggggcacccc ccttcggcgt gcgcggtcac gcgcacaggg cgcagccctg gttaaaaaca    13140
aggtttataa atattggttt aaaagcaggt taaaagacag gttagcggtg gccgaaaaac    13200
gggcggaaac ccttgcaaat gctggatttt ctgcctgtgg acagcccctc aaatgtcaat    13260
aggtgcgccc ctcatctgtc agcactctgc ccctcaagtg tcaaggatcg cgcccctcat    13320
ctgtcagtag tcgcgcccct caagtgtcaa taccgcaggg cacttatccc caggcttgtc    13380
cacatcatct gtgggaaact cgcgtaaaat caggcgtttt cgccgatttg cgaggctggc    13440
cagctccacg tcgccggccg aaatcgagcc tgccctcat ctgtcaacgc cgcgccgggt    13500
gagtcggccc ctcaagtgtc aacgtccgcc cctcatctgt cagtgagggc caagttttcc    13560
gcgaggtatc cacaacgccg gcggccgcgg tgtctcgcac acggcttcga cggcgtttct    13620
ggcgcgtttg cagggccata gacggccgcc agcccagcgg cgagggcaac cagcccggtg    13680
agcgtcgcaa aggagatcct gatctgactg atgggctgcc tgtatcgagt ggtgattttg    13740
tgccgagctg ccggtcgggg agctgttggc tggctggtgg caggatatat tgtggtgtaa    13800
acaaattgac gcttagacaa cttaataaca cattgcggac gtttttaatg tactggggtg    13860
gatgcactct agcgggcc                                                 13878
```

<210> SEQ ID NO 48
<211> LENGTH: 16277
<212> TYPE: DNA
<213> ORGANISM: Artificial
<220> FEATURE:
<221> NAME/KEY: misc_feature
<222> LOCATION: (1)..(16277)
<223> OTHER INFORMATION: complete sequence of vector pICH25881

<400> SEQUENCE: 48

```
ctgcaggtcc tgctgagcct cgacatgttg tcgcaaaatt cgccctggac ccgcccaacg     60
atttgtcgtc actgtcaagg tttgacctgc acttcatttg gcacatacac caaaaaaatg    120
ctgcataatt ctcggggcag caagtcggtt accggccgc cgtgctggac cgggttgaat    180
ggtgcccgta actttcggta gagcggacgg ccaatactca acttcaagga atctcaccca    240
tgcgcgccgg cggggaaccg gagttccctt cagtgagcgt tattagttcg ccgctcggtg    300
tgtcgtagat actagcccct ggggcacttt tgaaatttga ataagattta tgtaatcagt    360
cttttaggtt tgaccggttc tgccgctttt tttaaaattg gatttgtaat aataaaacgc    420
aattgtttgt tattgtggcg ctctatcata gatgtcgcta taaacctatt cagcacaata    480
tattgttttc attttaatat tgtacatata agtagtaggg tacaatcagt aaattgaacg    540
gagaatatta ttcataaaaa tacgatagta acgggtgata tattcattag aatgaaccga    600
aaccggcggt aaggatctga gctacacatg ctcaggtttt ttacaacgtg cacaacagaa    660
```

```
ttgaaagcaa atatcatgcg atcataggcg tctcgcatat ctcattaaag caggactcta    720
gaggatcctc agcggatctt ggtgaaggtc tggtagtggt cggtggtctt gtagatgagc    780
cagtcggagg agtagaggat gcggtcggag ttgcggaagc cggaggtgta gttgatgtcg    840
gcctccctcc aggtcctgcc cgacttgcct gggagcttgc cctcgcggtt tgagaagatg    900
tcgccgccga tggacttccc tggggccacg tcggcgaggt tgcccttgga ggccactgat    960
ccaccgcctc cacttcctcc gcctccgtcc tgctcgatgg agttgtgcac gatgatgtcg   1020
ttggccacga agttgtgcgg gcctggcacg gtgaggtcga cacctcctc cacgcccgtt    1080 tcggtgatgg acacgatgga gtcccagtag atgtcggact gggagagctt ctcgatctcc   1140
gggctcatga atcgatgctt aattagcttt ggttaattgg agtgatggca gtgtgtgtag   1200
atgaggctaa ttgcctgtgc catttataat gcctgtgatt aggacttttg ctagctaaga   1260
gtgtctaagc tgttgaagtg aagtttgagc gggatcaaac atgaaaatgg tgtgaatgat   1320
cagaaaagtt tgtaattagc aatgcttaat ttccactgtt tttgttttgc tgttatgcct   1380
tcctgttttt tttttccggt gcctgccctg accaaattta ttaagattga gagaaggtaa   1440
aacattttca acaaacatac tccctccgtt tctaaatatt tgataccatt gacttttag    1500 cacatgttta acctttcgtc atattcaaaa acttttgtga aatatgtaaa actatatgta   1560
tacatataag gtatatttaa ccaataaatc aaaatgatag aaaataatta ataattactt   1620
aaattttttt aaaataagac gaacattcaa acatatttaa acaaatagtc aatgacgtca   1680
aatatttaga aacggatgga gtagttatta atattcacc tcttcctatg gataaacagc    1740
accttttaca tccgaacaaa tggaagcata cacgccgggt tggctgccgg cattgcaatt   1800
aaagttattt cttcagtttg agatatttgt aaatgttaat ttgcaggaac taattaaata   1860
agtttgttgg agcttctaga atgtagatta attgtggcta tgtgatcgaa atattctcta   1920
cgaaatcgat ctaaatgtg gtgcatgcat tgtgcgtgtg tgctgattta agggattgta    1980
tcgtgggagc acaaaacaaa tgccgttcgt tggtttcgct acaacccaac ttaatttgca   2040
tctattaaga tagtgaccaa cctaaactga ttaactgcca tcattgtttt tatatgatac   2100
ctttattgtg gattttttt ttgccgcgcc gggacaaaga tgcaagcgga atttttgtaaa   2160 aagaaatttg aactgaacca aggcggcaca acaattatta atgctgggta tcggaaagat   2220
gtatgttccc tccgttacaa aataagctaa ccttgtacag tgtaggtaac attgaaggta   2280
tattcacacc gtacgggttt ggtttatttt tggacaaaga gacgggtagg taacaacatt   2340
tcagaaattt tagggactga cccgtagtgt cactcagtgt atttggaact catttgtgtg   2400
gcaaaaacat ttcccgaatg aatacagggt tttaaccct tggtgaccac cttttcaatc    2460
ccaagtgcaa agacaataga aaggtggctg tatgggtgt acctattcag tgaccgtctg    2520
tcacctttat ttctagtgga cgaccctttc attggatgcc atgtgtcatg gctaaaatat   2580
tgaactgtca tttaaattat taagtattaa acttctgtta attgaaaata tactgaggcc   2640
ccgtttggct aatgggaaag ggaaatcatt tcccacccac taaaagacat ctttaaattt   2700
taaccattta ttctccttct tccatttaat cctaaccctt cgttcatttc ccaatcccaa   2760
ttcccaccca cattattccc cattatccaa atacaacctg agggttttaa ccaaaattca   2820
ctttgaactg tgtaaaaaaa aggcgccgaa ttctcgagtg caggtcgatc tagtaacata   2880
gatgacaccg cgcgcgataa tttatcctag tttgcgcgct atattttgtt ttctatcgcg   2940
tattaaatgt ataattgcgg gactctaatc ataaaaccc atctcataaa taacgtcatg   3000
cattacatgt taattattac atgcttaacg taattcaaca gaaattatat gataatcatc   3060
```

```
gcaagaccgg caacaggatt caatcttaag aaactttatt gccaaatgtt tgaacgatct    3120
gcttgactct agagcttagc attagtacac agtcctgcca tcaccatcca ggatcatgtc    3180
cttgaatgcg cccccacttg ggatcatagg cagcacatgc tcctggtgcg ggacgatgat    3240
atccaacaag tatggccctg gagtctcgag catcttcttg atggcggcac ggacttcact    3300
cttctttgtt acacggactg caggaatatt gaaccccttg gcaatagtca caaaatctgg    3360
atatatctcg ctctcacatt ccgggttgcc caagtatgta tgcgccctat tcgccttgta    3420
aaacctatcc tcaagttgca ccaccatacc caaatgttgg ttgttcaaca ccatcacctt    3480
cacagggagg ttctcaatgc ggatcaatgc cagctcctga atgttcatga ggaagctacc    3540
atccccatca atatcaacaa ctgtgacacc tgggttagcc acagaagcac cagctgcagc    3600
aggcagccca aatcccattg cgcccagacc agccgaagac agccactgcc gtggccgctt    3660
gtaggtgtaa tattgtgccg cccacatctg gtgctgccca acaccagtag cgatgattgc    3720 ctcaccttc gtcagctcat ccagcacctg aatggcatat tgcggtggga tctcttcacc    3780
aaaagttttg taccccagag gaaactccct cttctgctgg tccaactcat tgtgccatgc    3840
actaaaatca gaacttgtct tgttgtcccc atggttaaaa caattggcgg cgatcgcccc    3900
attggctagc agaaaattat ggtcttgggg aagaccaata tcaaatattc tttgcactcc    3960
gagggaacga cgaccgataa ctttaaccat agcgcattga actcttcctc cgttactagc    4020
aatagaagta atatcaaggt tgttttgctt tctagtaaca ggaaaagaag cagcagactt    4080
aagtccagta aaaggagcaa ccatactagc ttgagcagca ctagcacgag tagcaacaac    4140
agcagcagaa gaaagcatag aagaagccat gttatcgata gcttatcgtc tacctacaaa    4200
aaagctccgc acgaggctgc atttgtcaca aatcatgaaa agaaaaacta ccgatgaaca    4260
atgctgaggg attcaaattc tacccacaaa aagaagaaag aaagatctag cacatctaag    4320
cctgacgaag cagcagaaat atataaaaat ataaaccata gtgccctttt ccctcttcc    4380 tgatcttgtt tagcatggcg gaaattttaa acccccatc atctcccca caacggcgg    4440 atcgcagatc tacatccgag agccccattc cccgcgagat ccgggccgga tccacgccgg    4500
cgagagcccc agccgcgaga tcccgcccct cccgcgcacc gatctgggcg cgcacgaagc    4560
cgcctctcgc ccacccaaac taccaaggcc aaagatcgag accgagacgg aaaaaaaaaa    4620
cggagaaaga aagaggagag gggcggggtg gttaccggcg cggcggcggc ggaggggag    4680 ggggaggag ctcgtcgtcc ggcagcgagg ggggaggagg tggaggtggt ggtggtggtg    4740
gtggtagggt tggggggatg ggaggagagg gggggtatg tatatagtgg cgatgggggg    4800
cgtttctttg gaagcggagg gagggccggc ctcgtcgctg gctcgcgatc ctcctcgcgt    4860
ttccggcccc cacgacccgg acccacctgc tgttttttct ttttctttt tttctttctt    4920 tttttttttt tggctgcgag acgtgcggtg cgtgcggaca actcacggtg atagtggggg    4980
ggtgtggaga ctattgtcca gttggctgga ctggggtggg ttgggttggg ttgggttggg    5040
ctgggcttgc tatggatcgt ggatagcact ttgggctttta ggaactttag gggttgtttt    5100
tgtaaatgtt ttgagtctaa gtttatcttt tattttttact agaaaaaata cccatgcgct    5160
gcaacggggg aaagctattt taatcttatt attgttcatt gtgagaattc gcctgaatat    5220
atatttttct caaaaattat gtcaaattag catatgggtt tttttaaaga tatttcttat    5280
acaaatccct ctgtatttac aaaagcaaac gaacttaaaa cccgactcaa atacagatat    5340
gcatttccaa aagcgaataa acttaaaaac caattcatac aaaaatgacg tatcaaagta    5400
```

```
ccgacaaaaa catcctcaat ttttataata gtagaaaaga gtaaatttca ctttgggcca      5460
ccttttatta ccgatatttt actttatacc accttttaac tgatgttttc acttttgacc      5520
aggtaatctt acctttgttt tattttggac tatcccgact ctcttctcaa gcatatgaat      5580
gacctcgacc ggcatgcaga tctggcgcgc cgtgccccaa ctggggtaac ctttgagttc      5640
tctcagttgg gggcgtaggg cccgctagag tgcatccacc ccagtacatt aaaaacgtcc      5700
gcaatgtgtt attaagttgt ctaagcgtca atttgtttac accacaatat atcctgccac      5760
cagccagcca acagctcccc gaccggcagc tcggcacaaa atcaccactc gatacaggca      5820
gcccatcagt cagatcagga tctcctttgc gacgctcacc gggctggttg ccctcgccgc      5880
tgggctggcg gccgtctatg gccctgcaaa cgcgccagaa acgccgtcga agccgtgtgc      5940
gagacaccgc ggccgccggc gttgtggata cctcgcggaa aacttggccc tcactgacag      6000
atgaggggcg gacgttgaca cttgaggggc cgactcaccc ggcgcggcgt tgacagatga      6060
ggggcaggct cgatttcggc cggcgacgtg gagctggcca gcctcgcaaa tcggcgaaaa      6120
cgcctgattt tacgcgagtt tcccacagat gatgtggaca agcctgggga taagtgccct      6180
gcggtattga cacttgaggg gcgcgactac tgacagatga ggggcgcgat ccttgacact      6240
tgaggggcag agtgctgaca gatgaggggc gcacctattg acatttgagg ggctgtccac      6300
aggcagaaaa tccagcattt gcaagggttt ccgcccgttt ttcggccacc gctaacctgt      6360
cttttaacct gcttttaaac caatatttat aaaccttgtt tttaaccagg gctgcgccct      6420
gtgcgcgtga ccgcgcacgc cgaaggggggg tgccccccct tctcgaaccc tcccggcccg      6480
ctaacgcggg cctcccatcc ccccagggggc tgcgcccctc ggccgcgaac ggcctcaccc      6540
caaaaatggc agcgctggcc aattcgtgcg cggaaccccct atttgtttat ttttctaaat      6600
acattcaaat atgtatccgc tcatgagaca ataaccctga taaatgcttc aataatattg      6660 aaaaggaag agtatggcta aaatgagaat atcaccggaa ttgaaaaaac tgatcgaaaa      6720
ataccgctgc gtaaaagata cggaaggaat gtctcctgct aaggtatata agctggtggg      6780
agaaaatgaa aacctatatt taaaaatgac ggacagccgg tataaaggga ccacctatga      6840
tgtggaacgg gaaaaggaca tgatgctatg gctggaagga agctgcctg ttccaaaggt       6900 cctgcacttt gaacggcatg atggctggag caatctgctc atgagtgagg ccgatggcgt      6960
cctttgctcg gaagagtatg aagatgaaca aagccctgaa aagattatcg agctgtatgc      7020
ggagtgcatc aggctctttc actccatcga catatcggat tgtccctata cgaatagctt      7080
agacagccgc ttagccgaat tggattactt actgaataac gatctggccg atgtggattg      7140
cgaaaactgg gaagaagaca ctccatttaa agatccgcgc gagctgtatg attttttaaa      7200
gacggaaaag cccgaagagg aacttgtctt ttcccacggc gacctgggag acagcaacat      7260
ctttgtgaaa gatggcaaag taagtggctt tattgatctt gggagaagcg gcagggcgga      7320
caagtggtat gacattgcct tctgcgtccg gtcgatcagg gaggatatcg gggaagaaca      7380
gtatgtcgag ctattttttg acttactggg gatcaagcct gattgggaga aaataaaata      7440
ttatatttta ctggatgaat tgttttagct gtcagaccaa gtttactcat atatacttta      7500
gattgattta aaacttcatt tttaatttaa aaggatctag gtgaagatcc ttttttgataa      7560 tctcatgacc aaaatccctt aacgtgagtt ttcgttccac tgagcgtcag accccgtaga      7620
aaagatcaaa ggatcttctt gagatccttt tttctgcgc gtaatctgct gcttgcaaac      7680
aaaaaaacca ccgctaccag cggtggtttg tttgccggat caagagctac caactctttt      7740
tccgaaggta actggcttca gcagagcgca gataccaaat actgtccttc tagtgtagcc      7800
```

-continued

```
gtagttaggc caccacttca agaactctgt agcaccgcct acatacctcg ctctgctaat   7860
cctgttacca gtggctgctg ccagtggcga taagtcgtgt cttaccgggt tggactcaag   7920
acgatagtta ccggataagg cgcagcggtc gggctgaacg gggggttcgt gcacacagcc   7980
cagcttggag cgaacgacct acaccgaact gagataccta cagcgtgagc tatgagaaag   8040
cgccacgctt cccgaaggga gaaaggcgga caggtatccg gtaagcggca gggtcggaac   8100
aggagagcgc acgagggagc ttccagggg aaacgcctgg tatctttata gtcctgtcgg   8160
gtttcgccac ctctgacttg agcgtcgatt tttgtgatgc tcgtcagggg gcggagcct   8220
atggaaaaac gccagcaacg cggccttttt acggttcctg gcagatccta gatgtggcgc   8280
aacgatgccg gcgacaagca ggagcgcacc gacttcttcc gcatcaagtg ttttggctct   8340
caggccgagg cccacggcaa gtatttgggc aaggggtcgc tggtattcgt gcagggcaag   8400
attcggaata ccaagtacga aaggacggc cagacggtct acgggaccga cttcattgcc   8460
gataaggtgg attatctgga caccaaggca ccaggcgggt caaatcagga ataagggcac   8520
attgccccgg cgtgagtcgg ggcaatcccg caaggagggt gaatgaatcg gacgtttgac   8580
cggaaggcat acaggcaaga actgatcgac gcggggtttt ccgccgagga tgccgaaacc   8640
atcgcaagcc gcaccgtcat gcgtgcgccc cgcgaaacct tccagtccgt cggctcgatg   8700
gtccagcaag ctacgccaa gatcgagcgc gacagcgtgc aactggctcc ccctgccctg   8760
cccgcgccat cggccgccgt ggagcgttcg cgtcgtctcg aacaggaggc ggcaggtttg   8820
gcgaagtcga tgaccatcga cacgcgagga actatgacga ccaagaagcg aaaaaccgcc   8880
ggcgaggacc tggcaaaaca ggtcagcgag gccaagcagg ccgcgttgct gaaacacacg   8940
aagcagcaga tcaaggaaat gcagcttttcc ttgttcgata ttgcgccgtg gccgacacg   9000
atgcgagcga tgccaaacga cacggcccgc tctgccctgt tcaccacgcg caacaagaaa   9060
atcccgcgcg aggcgctgca aaacaaggtc attttccacg tcaacaagga cgtgaagatc   9120
acctacaccg gcgtcgagct gcgggccgac gatgacgaac tggtgtggca gcaggtgttg   9180
gagtacgcga agcgcacccc tatcggcgag ccgatcacct tcacgttcta cgagcttgc   9240
caggacctgg gctggtcgat caatggccgg tattacacga aggccgagga atgcctgtcg   9300
cgcctacagg cgacggcgat gggcttcacg tccgaccgcg ttgggcacct ggaatcggtg   9360
tcgctgctgc accgcttccg cgtcctggac cgtggcaaga aaacgtcccg ttgccaggtc   9420
ctgatcgacg aggaaatcgt cgtgctgttt gctggcgacc actacacgaa attcatatgg   9480
gagaagtacc gcaagctgtc gccgacggcc cgacggatga tcgactattt cagctcgcac   9540
cgggagccgt acccgctcaa gctggaaacc ttccgcctca tgtgcggatc ggattccacc   9600
cgcgtgaaga agtggcgcga gcaggtcggc gaagcctgcg aagagttgcg aggcagcggc   9660
ctggtggaac acgcctgggt caatgatgac ctggtgcatt gcaaacgcta gggccttgtg   9720
gggtcagttc cggctggggg ttcagcagcc agcgcctgat ctgggaacc ctgtggttgg   9780
catgcacata caaatggacg aacggataaa ccttttcacg cccttttaaa tatccgatta   9840
ttctaataaa cgctctttc tcttaggttt acccgccaat atatcctgtc aaacactgat   9900
agtttaaact gaaggcggga aacgacaatc tgatctaagc tactcgacag atctgtgccc   9960
caactggggt aacctttgag ttctctcagt tgggggcgta gggaattcgg cgcctttttt  10020
ttacacagtt caaagtgaat tttggttaaa accctcaggt tgtatttgga caatgggaaa  10080
tatgtggtgg aattgggatt gggaaataaa tgaagggtta ggattaaatg gaagaaggag  10140
```

```
aataaaaggt taagatttaa agatgtctt tagtgggtgg gaaatgattt tccttccca    10200
ttagccaaac ggggcctcag tatattcca attaacagaa gtttaatact taataattta    10260
aatgacagtt caatatttta gccatgacac atggcatcca atgaaagggt cgtccactag   10320
aaataaaggt gacagacgat cactgaatag gtacacccat accagccacc tttctattgt    10380
ctttgcactt ggattgaaga gtggtcacaa gggttaaaac cctgaatcat tcggaaatgt    10440
ttttgccaca caaatgagct ccaaatacac tgagtgacac tacgggtcag tcactaaaat    10500
ttctgaaatg ttgttaccta ctcgtctctt tgtccaaaaa taaccaaac tcgtacggtg     10560
tgaatacatc ttcaatgtta cctacactgt acaagattag cttattttgt aacggaggga    10620
acatacatct ttcgataaca ctataattgt tgtgccgcct tggttcagtt caaatttctt    10680
tttacaaaat tccgcttgca tctttgtccc ggcgcggcaa aaaaaaaaat ccacaataaa    10740
ggtatcatat aaaaacaatg atggcagtta atcagtttag gttggtcact atcttaatag    10800
atgcaaatta agttgggttg tagcgaaacc aacgaacggc atttgtttg tgctcccacg     10860
atacaatccc ttaaatcagc acacgcac aatgcatgca ccacatttta gatcgatttc      10920
gtagagaata tttcgatcac atagccacaa ttaatctaca ttctagaagc tccaacaaac   10980
ttatttaatt agttcctgca aattaacatt tacaaatatc tcaaactgaa gaataacctt    11040
taattgcaat gccggcagcc aacccggcgt gtatgcttcc atttgttcga tgtaaagtgc   11100
tgtttatcca taggaagaga tgtaatatta ataactactc catcagtttc taaatatttg     11160
acgccattga tttttttta aatatgtttg aatgttcatc ttatttaaaa aaatttaagt      11220
aattattaat tattttccta tcattgatt tattgttaaa tatacttata tgtatacata      11280
tagttttaca tatttcacaa aagttttga atatgacgaa cggttaaata tgtgctaaaa     11340
agtcaatggt atcaaatatt tagaaacgga gggagtatat ttgttgaaaa tgttttacct    11400
tctctcaatc ttaataaatt tggtcagggc aggcacagaa aaaaaaaaca ggaagacata    11460
acagcaaaac aaaaacagtg gaaattaagc attgctaatt acaaactttt ctgatcattc    11520
acaccatttt catgtttgat ccagctcaaa cttcactaca acagcttaga acactcttag    11580
ctagcaaaag tcctaatcac agccattata aatagacaca agcaattagc ctcatctaca    11640
cacactccca tcactccaat taaccaaagc taattaagca tcgatatggc ccaagtgatt    11700
aacaccttcg acggcgtggc cgactacctc cagacctacc acaagctccc ggacaactac    11760
atcaccaagt ccgaggccca ggccctcggc tggagggagt ccggctgcat ctccggcgac    11820
tccctcatct ccctcgcctc caccggcaag gcgtgtcca tcaaggacct cctcgacgag    11880
aaggacttcg agatttgggc catcaacgag cagaccatga agctggagtc cgccaaggtg    11940
tcccgcgtgt tctgcaccgg caagaagctc gtctatatcc tcaagacccg cctcggcagg    12000
accatcaagg ccaccgccaa ccaccgcttc ctcaccatcg acggctggaa gcgcctcgac    12060
gagctgtccc tcaaggagca catcgccctc ccgcgcaagc tcgaatcctc ctccctccag    12120
ctctgactgc agtctagagt cctgctttaa tgagatatgc gagacgccta tgatcgcatg    12180
atatttgctt tcaattctgt tgtgcacgtt gtaaaaacc tgagcatgtg tagctcagat     12240
ccttaccgcc ggtttcggtt cattctaatg aatatatcac ccgttactat cgtatttta    12300
tgaataatat tctccgttca atttactgat tgtaccctac tacttatatg tacaatatta    12360
aaatgaaaac aatatattgt gctgaatagg tttatagcga catctatgat agagcgccac    12420
aataacaaac aattgcgttt tattattaca aatccaattt taaaaaaagc ggcagaaccg    12480
gtcaaaccta aaagactgat tacataaatc ttattcaaat ttcaaaagtg ccccaggggc    12540
```

```
tagtatctac gacacaccga gcggcgaact aataacgctc actgaaggga actccggttc   12600
cccgccggcg cgcatgggtg agattccttg aagttgagta ttggccgtcc gctctaccga   12660
aagttacggg caccattcaa cccggtccag cacggcggcc gggtaaccga cttgctgccc   12720
cgagaattat gcagcatttt tttggtgtat gtgccaaatg aagtgcaggt caaaccttga   12780
cagtgacgac aaatcgttgg gcgggtccag ggcgaatttt gcgacaacat gtcgaggctc   12840
agcaggacct gcatggcgcg ccagatctgc atgccggtcg aggtcattca tatgcttgag   12900
aagagagtcg ggatagtcca aaataaaaca aaggtaagat tacctggtca aaagtgaaaa   12960
catcagttaa aaggtggtat aaagtaaaat atcggtaata aaaggtggcc caaagtgaaa   13020
tttactcttt tctactatta taaaaattga ggatgttttt gtcggtactt tgatacgtca   13080
tttttgtatg aattggtttt taagtttatt cgcttttgga aatgcatatc tgtatttgag   13140
tcgggtttta agttcgtttg cttttgtaaa tacagaggga tttgtataag aaatatcttt   13200
aaaaaaaccc atatgctaat ttgacataat ttttgagaaa aatatatatt caggcgaatt   13260
ctcacaatga acaataataa gattaaaata gctttccccc gttgcagcgc atgggtattt   13320
tttctagtaa aaataaaaga taaacttaga ctcaaaacat ttacaaaaac aaccctaaa   13380 gttcctaaag cccaaagtgc tatccacgat ccatagcaag cccagcccaa cccaacccaa   13440
cccaacccac cccagtccag ccaactggac aatagtctcc acacccccc actatcaccg   13500 tgagttgtcc gcacgcaccg cacgtctcgc agccaaaaaa aaaaaagaa agaaaaaaaa   13560 gaaaaagaaa aaacagcagg tgggtccggg tcgtgggggc cggaaacgcg aggaggatcg   13620
cgagccagcg acgaggccgg ccctccctcc gcttccaaag aaacgccccc catcgccact   13680
atatacatac cccccctct cctcccatcc ccccaaccct accaccacca ccaccaccac   13740
ctccacctcc tccccctcg ctgccggacg acgagctcct cccccctccc cctccgccgc   13800
cgccgcgccg gtaaccaccc cgcccctctc ctctttcttt ctccgttttt tttttccgtc   13860
tcggtctcga tctttggcct tggtagttg ggtgggcgag aggcggcttc gtgcgcgccc   13920
agatcggtgc gcgggagggg cgggatcctcg cggctgggc tctcgccggc gtggatccgg   13980
cccggatctc gcgggaatg gggctctcgg atgtagatct gcgatccgcc gttgttgggg   14040
gagatgatgg ggggtttaaa atttccgcca tgctaaacaa gatcaggaag aggggaaaag   14100
ggcactatgg tttatatttt tatatatttc tgctgcttcg tcaggcttag atgtgctaga   14160
tctttctttc ttctttttgt gggtagaatt tgaatccctc agcattgttc atcggtagtt   14220
tttcttttca tgatttgtga caaatgcagc ctcgtgcgga gcttttttgt aggtagacga   14280
taagctatcg ataaacccat ggctacgacc gccgcggccg cggccgccgc cctgtccgcc   14340
gccgcgacgc ccaagaccgg ccgtaagaac caccagcgac accacgtcct tcccgctcga   14400
ggccgggtgg gggcggcggc ggtcaggtgc tcggcggtgt ccccggtcac cccgccgtcc   14460
ccggcgccgc cggccacgcc gctccggccg tggggggccgg ccgagcccg caagggcgcg   14520 gacatcctcg tggaggcgct ggagcggtgc ggcgtcagcg acgtgttcgc ctacccgggc   14580
ggcgcgtcca tggagatcca ccaggcgctg acgcgctccc cggtcatcac caaccacctc   14640
ttccgccacg agcagggcga ggcgttcgcg gcgtccgggt acgcgcgcgc gtccggccgc   14700 gtcgggtct gcgtcgccac ctccggcccc ggggcaacca acctcgtgtc cgcgctcgcc   14760
gacgcgctgc tcgactccgt cccgatggtc gccatcacgg gccaggtccc ccgccgcatg   14820
atcggcaccg acgccttcca ggagacgccc atagtcgagg tcacccgctc catcaccaag   14880
```

```
cacaattacc ttgtccttga tgtggaggac atccccgcg tcatacagga agccttcttc    14940
ctcgcgtcct cgggccgtcc tggcccggtg ctggtcgaca tccccaagga catccagcag   15000
cagatggccg tgccggtctg ggacacctcg atgaatctac agggtacat cgcacgcctg    15060 cccaagccac ccgcgacaga attgcttgag caggtcttgc gtctggttgg cgagtcacgg   15120
cgcccgattc tctatgtcgg tggtggctgc tctgcatctg gtgacgaatt gcgctggttt   15180
gttgagctga ctggtatccc agttacaacc actctgatgg gcctcggcaa tttcccagt    15240 gacgacccgt tgtccctgcg catgcttggg atgcatggca cggtgtacgc aaattatgcc   15300
gtggataagg ctgacctgtt gcttgcgttt ggtgtgcggt ttgatgatcg tgtgacaggg   15360
aaaattgagg cttttgcaag cagggccaag attgtgcaca ttgacattga tccagcagag   15420
attggaaaga caagcaacc acatgtgtca atttgcgcag atgttaagct tgctttacag    15480
ggcttgaatg ctctgctaca acagagcgac gtcaagtttg cggaatattg cctcagtttt   15540
ggcaccgaaa ttttaaccgt tgagtacggc ccattgccca ttggcaaaat tgtgagtgaa   15600
gaaattaatt gttctgtgta cagtgttgat ccagaaggga gagtttacac ccaggcgatc   15660
gcccaatggc atgaccgggg agagcaggaa gtattggaat atgaattgga agatggttca   15720
gtaatccgag ctacctctga ccaccgcttt ttaaccaccg attatcaact gttggcgatc   15780
gaagaaattt ttgctaggca actggacttg ttgactttag aaaatattaa gcaaactgaa   15840
gaagctcttg acaaccatcg tcttcccttt ccattacttg acgctgggac aattaaataa   15900
ctgcaggtcg actctagagt caagcagatc gttcaaacat ttggcaataa agtttcttaa   15960
gattgaatcc tgttgccggt cttgcgatga ttatcatata atttctgttg aattacgtta   16020
agcatgtaat aattaacatg taatgcatga cgttatttat gagatgggtt tttatgatta   16080
gagtcccgca attatacatt taatacgcga tagaaaacaa aatatagcgc gcaaactagg   16140
ataaattatc gcgcgcggtg tcatctatgt tactagatcg acctgcactc gagctcgaag   16200
ccgcggtgcg ggtgccaggg cgtgcccttg ggctccccgg gcgcgtactc cacctcaccc   16260
atcactagtt gtggtac                                                 16277
```

<210> SEQ ID NO 49
<211> LENGTH: 333
<212> TYPE: DNA
<213> ORGANISM: Artificial
<220> FEATURE:
<221> NAME/KEY: misc_feature
<222> LOCATION: (1)..(333)
<223> OTHER INFORMATION: codon-optimized barnase sequence from Bacillus amyloliquefaciens

<400> SEQUENCE: 49

```
atggcccaag tgattaacac cttcgacggc gtggccgact acctccagac ctaccacaag    60 ctccccggaca actacatcac caagtccgag gcccaggccc tcggctgggt ggcctccaag   120
ggcaacctcg ccgacgtggc cccagggaag tccatcggcg cgacatcctt ctccaaccgc   180
gagggcaagc tcccaggcaa gtcgggcagg acctggaggg aggccgacat caactacacc   240
tccggcttcc gcaactccga ccgcatcctc tactcctccg actggctcat ctacaagacc   300
accgaccact accagacctt caccaagatc cgc                                333
```

<210> SEQ ID NO 50
<211> LENGTH: 111
<212> TYPE: PRT
<213> ORGANISM: Artificial
<220> FEATURE:

<221> NAME/KEY: MISC_FEATURE
<222> LOCATION: (1)..(111)
<223> OTHER INFORMATION: codon-optimized amino acid sequence of the
      barnase enzyme from Bacillus amyloliquefaciens

<400> SEQUENCE: 50

Met Ala Gln Val Ile Asn Thr Phe Asp Gly Val Ala Asp Tyr Leu Gln
1               5                   10                  15

Thr Tyr His Lys Leu Pro Asp Asn Tyr Ile Thr Lys Ser Glu Ala Gln
            20                  25                  30

Ala Leu Gly Trp Val Ala Ser Lys Gly Asn Leu Ala Asp Val Ala Pro
        35                  40                  45

Gly Lys Ser Ile Gly Gly Asp Ile Phe Ser Asn Arg Glu Gly Lys Leu
    50                  55                  60

Pro Gly Lys Ser Gly Arg Thr Trp Arg Glu Ala Asp Ile Asn Tyr Thr
65                  70                  75                  80

Ser Gly Phe Arg Asn Ser Asp Arg Ile Leu Tyr Ser Ser Asp Trp Leu
                85                  90                  95

Ile Tyr Lys Thr Thr Asp His Tyr Gln Thr Phe Thr Lys Ile Arg
            100                 105                 110

<210> SEQ ID NO 51
<211> LENGTH: 1932
<212> TYPE: DNA
<213> ORGANISM: Artificial
<220> FEATURE:
<221> NAME/KEY: misc_feature
<222> LOCATION: (1)..(1932)
<223> OTHER INFORMATION: codon-optimized ALS (acetolactate synthase)
      sequence from Oryza sativa

<400> SEQUENCE: 51
atggctacga ccgccgcggc cgcggccgcc gccctgtccg ccgccgcgac ggccaagacc      60
ggccgtaaga accaccagcg acaccacgtc cttcccgctc gaggccgggt ggggcggcg     120 gcggtcaggt gctcggcggt gtcccggtc acccgccgt cccggcgcc gccggccacg      180 ccgctccggc cgtggggggcc ggccgagccc cgcaagggcg cggacatcct cgtggaggcg     240
ctggagcggt gcggcgtcag cgacgtgttc gcctacccgg gcggcgcgtc catggagatc     300
caccaggcgc tgacgcgctc cccggtcatc accaaccacc tcttccgcca cgagcagggc     360
gaggcgttcg cggcgtccgg gtacgcgcgc gtccggcc gtcggggt ctgcgtcgcc        420 acctccggcc ccgggcaac caacctcgtg tccgcgctcg ccgacgcgct gctcgactcc     480
gtcccgatgg tcgccatcac gggccaggtc cccgccgca tgatcggcac cgacgccttc     540
caggagacgc ccatagtcga ggtcacccgc tccatcacca agcacaatta ccttgtcctt     600
gatgtggagg acatccccg cgtcatacag gaagccttct tcctcgcgtc ctcgggccgt     660
cctggcccgg tgctggtcga catccccaag gacatccagc agcagatggc cgtgccggtc     720
tgggacacct cgatgaatct accagggtac atcgcacgcc tgcccaagcc acccgcgaca     780
gaattgcttg agcaggtctt cgtctggtt ggcgagtcac ggcgcccgat tctctatgtc     840
ggtggtggct gctctgcatc tggtgacgaa ttgcgctggt tgttgagct gactggtatc     900 ccagttacaa ccactctgat gggcctcggc aatttcccca gtgacgaccc gttgtccctg     960
cgcatgcttg ggatgcatgg cacggtgtac gcaaattatg ccgtggataa ggctgacctg    1020
ttgcttgcgt tggtgtgcg gtttgatgat cgtgtgacag ggaaaattga ggcttttgca    1080
agcagggcca agattgtgca cattgacatt gatccagcag agattggaaa gaacaagcaa    1140

```
ccacatgtgt caatttgcgc agatgttaag cttgctttac agggcttgaa tgctctgcta    1200
caacagagca caacaaagac aagttctgat tttagtgcat ggcacaatga gttggaccag    1260
cagaagaggg agtttcctct ggggtacaaa acttttggtg aagagatccc accgcaatat    1320
gccattcagg tgctggatga gctgacgaaa ggtgaggcaa tcatcgctac tggtgttggg    1380
cagcaccaga tgtgggcggc acaatattac acctacaagc ggccacggca gtggctgtct    1440
tcggctggtc tgggcgcaat gggatttggg ctgcctgctg cagctggtgc ttctgtggct    1500
aacccaggtg tcacagttgt tgatattgat ggggatggta gcttcctcat gaacattcag    1560
gagctggcat tgatccgcat tgagaacctc cctgtgaagg tgatggtgtt gaacaaccaa    1620
catttgggta tggtggtgca acttgaggat aggttttaca aggcgaatag ggcgcataca    1680
tacttgggca acccggaatg tgagagcgag atatatccag attttgtgac tattgctaag    1740
gggttcaata ttcctgcagt ccgtgtaaca aagaagagtg aagtccgtgc cgccatcaag    1800
aagatgctcg agactccagg gccatacttg ttggatatca tcgtcccgca ccaggagcat    1860
gtgctgccta tgatcccaag tgggggcgca ttcaaggaca tgatcctgga tggtgatggc    1920
aggactgtgt ac                                                        1932
```

<210> SEQ ID NO 52
<211> LENGTH: 644
<212> TYPE: PRT
<213> ORGANISM: Artificial
<220> FEATURE:
<221> NAME/KEY: MISC_FEATURE
<222> LOCATION: (1)..(644)
<223> OTHER INFORMATION: codon-optimized amino acid sequence of the ALS
      (acetolactate synthase) sequence from Oryza sativa

<400> SEQUENCE: 52

```
Met Ala Thr Thr Ala Ala Ala Ala Ala Ala Leu Ser Ala Ala Ala
1               5                   10                  15

Thr Ala Lys Thr Gly Arg Lys Asn His Gln Arg His His Val Leu Pro
                20                  25                  30

Ala Arg Gly Arg Val Gly Ala Ala Val Arg Cys Ser Ala Val Ser
        35                  40                  45

Pro Val Thr Pro Pro Ser Pro Ala Pro Pro Ala Thr Pro Leu Arg Pro
    50                  55                  60

Trp Gly Pro Ala Glu Pro Arg Lys Gly Ala Asp Ile Leu Val Glu Ala
65                  70                  75                  80

Leu Glu Arg Cys Gly Val Ser Asp Val Phe Ala Tyr Pro Gly Gly Ala
                85                  90                  95

Ser Met Glu Ile His Gln Ala Leu Thr Arg Ser Pro Val Ile Thr Asn
            100                 105                 110

His Leu Phe Arg His Glu Gln Gly Glu Ala Phe Ala Ala Ser Gly Tyr
        115                 120                 125

Ala Arg Ala Ser Gly Arg Val Gly Val Cys Val Ala Thr Ser Gly Pro
    130                 135                 140

Gly Ala Thr Asn Leu Val Ser Ala Leu Ala Asp Ala Leu Leu Asp Ser
145                 150                 155                 160

Val Pro Met Val Ala Ile Thr Gly Gln Val Pro Arg Arg Met Ile Gly
                165                 170                 175

Thr Asp Ala Phe Gln Glu Thr Pro Ile Val Glu Val Thr Arg Ser Ile
            180                 185                 190

Thr Lys His Asn Tyr Leu Val Leu Asp Val Glu Asp Ile Pro Arg Val
        195                 200                 205
```

-continued

```
Ile Gln Glu Ala Phe Phe Leu Ala Ser Ser Gly Arg Pro Gly Pro Val
    210                 215                 220

Leu Val Asp Ile Pro Lys Asp Ile Gln Gln Met Ala Val Pro Val
225                 230                 235                 240

Trp Asp Thr Ser Met Asn Leu Pro Gly Tyr Ile Ala Arg Leu Pro Lys
                245                 250                 255

Pro Pro Ala Thr Glu Leu Leu Glu Gln Val Leu Arg Leu Val Gly Glu
                260                 265                 270

Ser Arg Arg Pro Ile Leu Tyr Val Gly Gly Cys Ser Ala Ser Gly
            275                 280                 285

Asp Glu Leu Arg Trp Phe Val Glu Leu Thr Gly Ile Pro Val Thr Thr
290                 295                 300

Thr Leu Met Gly Leu Gly Asn Phe Pro Ser Asp Asp Pro Leu Ser Leu
305                 310                 315                 320

Arg Met Leu Gly Met His Gly Thr Val Tyr Ala Asn Tyr Ala Val Asp
                325                 330                 335

Lys Ala Asp Leu Leu Leu Ala Phe Gly Val Arg Phe Asp Asp Arg Val
            340                 345                 350

Thr Gly Lys Ile Glu Ala Phe Ala Ser Arg Ala Lys Ile Val His Ile
            355                 360                 365

Asp Ile Asp Pro Ala Glu Ile Gly Lys Asn Lys Gln Pro His Val Ser
370                 375                 380

Ile Cys Ala Asp Val Lys Leu Ala Leu Gln Gly Leu Asn Ala Leu Leu
385                 390                 395                 400

Gln Gln Ser Thr Thr Lys Thr Ser Ser Asp Phe Ser Ala Trp His Asn
                405                 410                 415

Glu Leu Asp Gln Gln Lys Arg Glu Phe Pro Leu Gly Tyr Lys Thr Phe
            420                 425                 430

Gly Glu Glu Ile Pro Pro Gln Tyr Ala Ile Gln Val Leu Asp Glu Leu
            435                 440                 445

Thr Lys Gly Glu Ala Ile Ile Ala Thr Gly Val Gly Gln His Gln Met
450                 455                 460

Trp Ala Ala Gln Tyr Tyr Thr Tyr Lys Arg Pro Arg Gln Trp Leu Ser
465                 470                 475                 480

Ser Ala Gly Leu Gly Ala Met Gly Phe Gly Leu Pro Ala Ala Ala Gly
                485                 490                 495

Ala Ser Val Ala Asn Pro Gly Val Thr Val Val Asp Ile Asp Gly Asp
            500                 505                 510

Gly Ser Phe Leu Met Asn Ile Gln Glu Leu Ala Leu Ile Arg Ile Glu
            515                 520                 525

Asn Leu Pro Val Lys Val Met Val Leu Asn Asn Gln His Leu Gly Met
530                 535                 540

Val Val Gln Leu Glu Asp Arg Phe Tyr Lys Ala Asn Arg Ala His Thr
545                 550                 555                 560

Tyr Leu Gly Asn Pro Glu Cys Glu Ser Glu Ile Tyr Pro Asp Phe Val
                565                 570                 575

Thr Ile Ala Lys Gly Phe Asn Ile Pro Ala Val Arg Val Thr Lys Lys
            580                 585                 590

Ser Glu Val Arg Ala Ala Ile Lys Lys Met Leu Glu Thr Pro Gly Pro
            595                 600                 605

Tyr Leu Leu Asp Ile Ile Val Pro His Gln Glu His Val Leu Pro Met
610                 615                 620
```

Ile Pro Ser Gly Gly Ala Phe Lys Asp Met Ile Leu Asp Gly Asp Gly
625                 630                 635                 640

Arg Thr Val Tyr

<210> SEQ ID NO 53
<211> LENGTH: 1209
<212> TYPE: DNA
<213> ORGANISM: Artificial
<220> FEATURE:
<221> NAME/KEY: misc_feature
<222> LOCATION: (1)..(1209)
<223> OTHER INFORMATION: not codon-optimized N-terminus of the ALS
      (acetolactate synthase) sequence from Oryza sativa

<400> SEQUENCE: 53

| | | | | |
|---|---|---|---|---|
| atggctacga | ccgccgcggc | cgcggccgcc | gccctgtccg | ccgccgcgac ggccaagacc | 60 |
| ggccgtaaga | accaccagcg | acaccacgtc | cttcccgctc | gaggccgggt ggggcggcg | 120 |
| gcggtcaggt | gctcggcggt | gtccccggtc | acccgccgt | ccccggcgcc gccggccacg | 180 |
| ccgctccggc | cgtgggggcc | ggccgagccc | cgcaaggggcg | cggacatcct cgtggaggcg | 240 |
| ctggagcggt | gcggcgtcag | cgacgtgttc | gcctacccgg | cggcgcgtc catggagatc | 300 |
| caccaggcgc | tgacgcgctc | cccggtcatc | accaaccacc | tcttccgcca cgagcagggc | 360 |
| gaggcgttcg | cggcgtccgg | gtacgcgcgc | gcgtccggcc | gcgtcgggt ctgcgtcgcc | 420 |
| acctccggcc | ccggggcaac | caacctcgtg | tccgcgctcg | ccgacgcgct gctcgactcc | 480 |
| gtcccgatgg | tcgccatcac | gggccaggtc | ccccgccgca | tgatcggcac cgacgccttc | 540 |
| caggagacgc | ccatagtcga | ggtcacccgc | tccatcacca | agcacaatta ccttgtcctt | 600 |
| gatgtggagg | acatccccg | cgtcatacag | gaagccttct | tcctcgcgtc ctcgggccgt | 660 |
| cctggcccgg | tgctggtcga | catccccaag | gacatccagc | agcagatggc cgtgccggtc | 720 |
| tgggacacct | cgatgaatct | accagggtac | atcgcacgcc | tgcccaagcc acccgcgaca | 780 |
| gaattgcttg | agcaggtctt | gcgtctggtt | ggcgagtcac | ggcgcccgat tctctatgtc | 840 |
| ggtggtggct | gctctgcatc | tggtgacgaa | ttgcgctggt | ttgttgagct gactggtatc | 900 |
| ccagttacaa | ccactctgat | gggcctcggc | aatttcccca | gtgacgaccc gttgtccctg | 960 |
| cgcatgcttg | ggatgcatgg | cacggtgtac | gcaaattatg | ccgtggataa ggctgacctg | 1020 |
| ttgcttgcgt | ttggtgtgcg | gtttgatgat | cgtgtgacag | ggaaaattga ggcttttgca | 1080 |
| agcagggcca | agattgtgca | cattgacatt | gatccagcag | agattggaaa gaacaagcaa | 1140 |
| ccacatgtgt | caatttgcgc | agatgttaag | cttgctttac | agggcttgaa tgctctgcta | 1200 |
| caacagagc | | | | | 1209 |

<210> SEQ ID NO 54
<211> LENGTH: 403
<212> TYPE: PRT
<213> ORGANISM: Artificial
<220> FEATURE:
<221> NAME/KEY: MISC_FEATURE
<222> LOCATION: (1)..(403)
<223> OTHER INFORMATION: not codon-optimized N-terminus of the ALS
      (acetolactate synthase) sequence from Oryza sativa

<400> SEQUENCE: 54

Met Ala Thr Thr Ala Ala Ala Ala Ala Ala Leu Ser Ala Ala
1               5                   10              15

Thr Ala Lys Thr Gly Arg Lys Asn His Gln Arg His His Val Leu Pro
                20                  25                  30

| | | | | | | | | | | | |
|---|---|---|---|---|---|---|---|---|---|---|---|
|Ala|Arg|Gly|Arg|Val|Gly|Ala|Ala|Val|Arg|Cys|Ser|Ala|Val|Ser|

Ala Arg Gly Arg Val Gly Ala Ala Val Arg Cys Ser Ala Val Ser
            35                  40                  45

Pro Val Thr Pro Pro Ser Pro Ala Pro Pro Ala Thr Pro Leu Arg Pro
 50                  55                  60

Trp Gly Pro Ala Glu Pro Arg Lys Gly Ala Asp Ile Leu Val Glu Ala
 65                  70                  75                  80

Leu Glu Arg Cys Gly Val Ser Asp Val Phe Ala Tyr Pro Gly Gly Ala
                85                  90                  95

Ser Met Glu Ile His Gln Ala Leu Thr Arg Ser Pro Val Ile Thr Asn
            100                 105                 110

His Leu Phe Arg His Glu Gln Gly Glu Ala Phe Ala Ala Ser Gly Tyr
        115                 120                 125

Ala Arg Ala Ser Gly Arg Val Gly Val Cys Val Ala Thr Ser Gly Pro
130                 135                 140

Gly Ala Thr Asn Leu Val Ser Ala Leu Ala Asp Ala Leu Leu Asp Ser
145                 150                 155                 160

Val Pro Met Val Ala Ile Thr Gly Gln Val Pro Arg Arg Met Ile Gly
                165                 170                 175

Thr Asp Ala Phe Gln Glu Thr Pro Ile Val Glu Val Thr Arg Ser Ile
            180                 185                 190

Thr Lys His Asn Tyr Leu Val Leu Asp Val Glu Asp Ile Pro Arg Val
        195                 200                 205

Ile Gln Glu Ala Phe Phe Leu Ala Ser Ser Gly Arg Pro Gly Pro Val
    210                 215                 220

Leu Val Asp Ile Pro Lys Asp Ile Gln Gln Gln Met Ala Val Pro Val
225                 230                 235                 240

Trp Asp Thr Ser Met Asn Leu Pro Gly Tyr Ile Ala Arg Leu Pro Lys
                245                 250                 255

Pro Pro Ala Thr Glu Leu Leu Glu Gln Val Leu Arg Leu Val Gly Glu
            260                 265                 270

Ser Arg Arg Pro Ile Leu Tyr Val Gly Gly Gly Cys Ser Ala Ser Gly
        275                 280                 285

Asp Glu Leu Arg Trp Phe Val Glu Leu Thr Gly Ile Pro Val Thr Thr
290                 295                 300

Thr Leu Met Gly Leu Gly Asn Phe Pro Ser Asp Asp Pro Leu Ser Leu
305                 310                 315                 320

Arg Met Leu Gly Met His Gly Thr Val Tyr Ala Asn Tyr Ala Val Asp
                325                 330                 335

Lys Ala Asp Leu Leu Leu Ala Phe Gly Val Arg Phe Asp Asp Arg Val
            340                 345                 350

Thr Gly Lys Ile Glu Ala Phe Ala Ser Arg Ala Lys Ile Val His Ile
        355                 360                 365

Asp Ile Asp Pro Ala Glu Ile Gly Lys Asn Lys Gln Pro His Val Ser
370                 375                 380

Ile Cys Ala Asp Val Lys Leu Ala Leu Gln Gly Leu Asn Ala Leu Leu
385                 390                 395                 400

Gln Gln Ser

<210> SEQ ID NO 55
<211> LENGTH: 723
<212> TYPE: DNA
<213> ORGANISM: Artificial
<220> FEATURE:
<221> NAME/KEY: misc_feature
<222> LOCATION: (1)..(723)

<223> OTHER INFORMATION: not codon-optimized C-terminus of the ALS
(acetolactate synthase) sequence from Oryza sativa

<400> SEQUENCE: 55

```
acaacaaaga caagttctga ttttagtgca tggcacaatg agttggacca gcagaagagg      60
gagtttcctc tggggtacaa aacttttggt gaagagatcc caccgcaata tgccattcag     120
gtgctggatg agctgacgaa aggtgaggca atcatcgcta ctggtgttgg cagcaccag      180
atgtgggcgg cacaatatta cacctacaag cggccacggc agtggctgtc ttcggctggt     240
ctgggcgcaa tgggatttgg gctgcctgct gcagctggtg cttctgtggc taacccaggt     300
gtcacagttg ttgatattga tggggatggt agcttcctca tgaacattca ggagctggca     360
ttgatccgca ttgagaacct ccctgtgaag gtgatggtgt tgaacaacca acatttgggt     420
atggtggtgc aacttgagga taggttttac aaggcgaata gggcgcatac atacttgggc     480
aacccggaat gtgagagcga gatatatcca gattttgtga ctattgctaa ggggttcaat     540
attcctgcag tccgtgtaac aaagaagagt gaagtccgtg ccgccatcaa gaagatgctc     600
gagactccag ggccatactt gttggatatc atcgtcccgc accaggagca tgtgctgcct     660
atgatcccaa gtggggcgc attcaaggac atgatcctgg atggtgatgg caggactgtg     720
tac                                                                   723
```

<210> SEQ ID NO 56
<211> LENGTH: 241
<212> TYPE: PRT
<213> ORGANISM: Artificial
<220> FEATURE:
<221> NAME/KEY: MISC_FEATURE
<222> LOCATION: (1)..(241)
<223> OTHER INFORMATION: not codon-optimized C-terminus of the ALS
(acetolactate synthase) sequence from Oryza sativa

<400> SEQUENCE: 56

```
Thr Thr Lys Thr Ser Ser Asp Phe Ser Ala Trp His Asn Glu Leu Asp
1               5                   10                  15

Gln Gln Lys Arg Glu Phe Pro Leu Gly Tyr Lys Thr Phe Gly Glu Glu
            20                  25                  30

Ile Pro Pro Gln Tyr Ala Ile Gln Val Leu Asp Glu Leu Thr Lys Gly
        35                  40                  45

Glu Ala Ile Ile Ala Thr Gly Val Gly Gln His Gln Met Trp Ala Ala
    50                  55                  60

Gln Tyr Tyr Thr Tyr Lys Arg Pro Arg Gln Trp Leu Ser Ser Ala Gly
65                  70                  75                  80

Leu Gly Ala Met Gly Phe Gly Leu Pro Ala Ala Gly Ala Ser Val
                85                  90                  95

Ala Asn Pro Gly Val Thr Val Val Asp Ile Asp Gly Asp Gly Ser Phe
            100                 105                 110

Leu Met Asn Ile Gln Glu Leu Ala Leu Ile Arg Ile Glu Asn Leu Pro
        115                 120                 125

Val Lys Val Met Val Leu Asn Asn Gln His Leu Gly Met Val Val Gln
    130                 135                 140

Leu Glu Asp Arg Phe Tyr Lys Ala Asn Arg Ala His Thr Tyr Leu Gly
145                 150                 155                 160

Asn Pro Glu Cys Glu Ser Glu Ile Tyr Pro Asp Phe Val Thr Ile Ala
                165                 170                 175

Lys Gly Phe Asn Ile Pro Ala Val Arg Val Thr Lys Lys Ser Glu Val
            180                 185                 190
```

```
Arg Ala Ala Ile Lys Lys Met Leu Glu Thr Pro Gly Pro Tyr Leu Leu
        195                 200                 205

Asp Ile Ile Val Pro His Gln Glu His Val Leu Pro Met Ile Pro Ser
    210                 215                 220

Gly Gly Ala Phe Lys Asp Met Ile Leu Asp Gly Asp Gly Arg Thr Val
225                 230                 235                 240

Tyr

<210> SEQ ID NO 57
<211> LENGTH: 60
<212> TYPE: PRT
<213> ORGANISM: Artificial
<220> FEATURE:
<221> NAME/KEY: SIGNAL
<222> LOCATION: (1)..(60)
<223> OTHER INFORMATION: artificial chloroplast targeting sequence used
      as an N-terminal signal sequence

<400> SEQUENCE: 57

Met Ala Ser Ser Met Leu Ser Ser Ala Ala Val Val Ala Thr Arg Ala
1               5                   10                  15

Ser Ala Ala Gln Ala Ser Met Val Ala Pro Phe Thr Gly Leu Lys Ser
            20                  25                  30

Ala Ala Ser Phe Pro Val Thr Arg Lys Gln Asn Asn Leu Asp Ile Thr
        35                  40                  45

Ser Ile Ala Ser Asn Gly Gly Arg Val Gln Cys Ala
    50                  55                  60

<210> SEQ ID NO 58
<211> LENGTH: 20
<212> TYPE: DNA
<213> ORGANISM: Artificial
<220> FEATURE:
<223> OTHER INFORMATION: DNA primer

<400> SEQUENCE: 58
gcatcgatat ggcccaagtg                                                 20

<210> SEQ ID NO 59
<211> LENGTH: 22
<212> TYPE: DNA
<213> ORGANISM: Artificial
<220> FEATURE:
<223> OTHER INFORMATION: DNA primer

<400> SEQUENCE: 59
gagctggagg gaggaggatt cg                                              22

<210> SEQ ID NO 60
<211> LENGTH: 20
<212> TYPE: DNA
<213> ORGANISM: Artificial
<220> FEATURE:
<223> OTHER INFORMATION: DNA primer

<400> SEQUENCE: 60
gatcttggtg aagtctgtag                                                 20

<210> SEQ ID NO 61
<211> LENGTH: 21
<212> TYPE: DNA
<213> ORGANISM: Artificial
<220> FEATURE:
```

<223> OTHER INFORMATION: DNA primer

<400> SEQUENCE: 61
gggactccat cgtgtccatc c                                              21

<210> SEQ ID NO 62
<211> LENGTH: 21
<212> TYPE: DNA
<213> ORGANISM: Artificial
<220> FEATURE:
<223> OTHER INFORMATION: DNA primer

<400> SEQUENCE: 62
gtcagcgacg tgttcgccta c                                              21

<210> SEQ ID NO 63
<211> LENGTH: 20
<212> TYPE: DNA
<213> ORGANISM: Artificial
<220> FEATURE:
<223> OTHER INFORMATION: DNA primer

<400> SEQUENCE: 63
gtcctccaat caaggacaag                                                20

<210> SEQ ID NO 64
<211> LENGTH: 20
<212> TYPE: DNA
<213> ORGANISM: Artificial
<220> FEATURE:
<223> OTHER INFORMATION: DNA primer

<400> SEQUENCE: 64
gcaatatgcc attcaggtgc                                                20

<210> SEQ ID NO 65
<211> LENGTH: 20
<212> TYPE: DNA
<213> ORGANISM: Artificial
<220> FEATURE:
<223> OTHER INFORMATION: DNA primer

<400> SEQUENCE: 65
cacggactgc aggaatattg                                                20

<210> SEQ ID NO 66
<211> LENGTH: 20
<212> TYPE: DNA
<213> ORGANISM: Artificial
<220> FEATURE:
<223> OTHER INFORMATION: DNA primer

<400> SEQUENCE: 66
gattctctat gtcggtggtg                                                20

<210> SEQ ID NO 67
<211> LENGTH: 21
<212> TYPE: DNA
<213> ORGANISM: Artificial
<220> FEATURE:
<223> OTHER INFORMATION: DNA primer

<400> SEQUENCE: 67
gcgacagaat tgcttgagca g                                              21

```
<210> SEQ ID NO 68
<211> LENGTH: 20
<212> TYPE: DNA
<213> ORGANISM: Artificial
<220> FEATURE:
<223> OTHER INFORMATION: DNA primer

<400> SEQUENCE: 68
ctggggtgga tgcactctag                                                 20

<210> SEQ ID NO 69
<211> LENGTH: 19
<212> TYPE: DNA
<213> ORGANISM: Artificial
<220> FEATURE:
<223> OTHER INFORMATION: DNA primer

<400> SEQUENCE: 69
ggtgcaactt gaggatagg                                                  19

<210> SEQ ID NO 70
<211> LENGTH: 22
<212> TYPE: DNA
<213> ORGANISM: Artificial
<220> FEATURE:
<223> OTHER INFORMATION: DNA primer

<400> SEQUENCE: 70
ctaccagacc ttcaccaaga tc                                              22

<210> SEQ ID NO 71
<211> LENGTH: 22
<212> TYPE: DNA
<213> ORGANISM: Artificial
<220> FEATURE:
<223> OTHER INFORMATION: DNA primer

<400> SEQUENCE: 71
gatctaagct actcgacaga tc                                              22
```

PROCESS OF PRODUCING MALE STERILE MONOCOTYLEDONOUS PLANTS

CROSS-REFERENCE TO RELATED APPLICATIONS

The present application is a U.S. National Stage entry under 35 U.S.C. §371 of International Application No. PCT/EP2009/056825, filed Jun. 3, 2009, designating the United States of America and published in English on Dec. 10, 2009, which in turn claims priority to European Patent Application No. EP 08157508.6 filed Jun. 3, 2008, each of which is incorporated herein by reference in its entirety.

The present invention relates to a process of producing male sterile monocotyledonous plants by introducing into said plants fragments of a nucleotide sequence coding for a protein which provides for male sterility and reconstituting the complete protein which provides for male sterility by intein-mediated trans-splicing.

In agriculture, the demand for male sterile plants is increasing for several reasons. First, the use of male sterile plants leads to an enhanced safety of transgenic plants, as these male sterile plants allow to control transgene flow and avoid the undesired and random transfer of foreign genes to related plant species through pollen.

Second, it allows the production of hybrid seeds which are produced by cross-pollination of genetically different parental lines. The hybrid progeny shows the so-called "heterosis effect" which means that they display superior plant growth, seed yield and a pronounced stress tolerance in comparison to both parental lines.

For naturally self-pollinating plants, the plant must be male sterilized during the crossing process in order to avoid self-fertilization. In corn, castration of the female crossing partner is easily achieved by mechanical detasselling (removal of anthers), and is followed by pollination with pollen from another line. However, this technique is not commercially feasible in the case of crops with small flowers, i.e. all economically important crops other than maize.

To induce male sterility on a cellular basis, both cytoplasmic male sterility (CMS) and nuclear male sterility (NMS) systems have been developed. However, CMS-based hybridization technology is a multi-component genetic system that is difficult to discover, introgress and maintain. First, a genetic source of male sterility must be identified. Second, for the propagation of male sterile phenotypes, so-called "maintainer lines" are needed. Third, in crops in which the seed or fruit is the harvested product, fertility in the hybrid must be restored, thus fertility restorer lines are required. Historically, these genetic components have had to be discovered and brought together for each crop species separately. As a result, the existing hybridization systems introduced by classical breeding methods are difficult to develop, complex to maintain, often marginally reliable and species-specific.

Hence, nowadays it is an object to develop nuclear male sterility systems which are characterized by mutations in the genome of the plant. One transgenic system which was first developed in rapeseed and which is used commercially for hybrid production is based on male sterility conferred by the tapetum-specific expression of the toxic enzyme barnase which is a ribonuclease from *Bacillus amyloliquefaciens* (Mariani et al. (1990) Nature 347: 737-741; Mariani et al. (1992) Nature 357: 384-387). This barnase system for inducing male sterility has also been successfully used in monocotyledonous plants (De Block et al. (1997) Theor. Appl. Genet. 95: 125-131).

However, such a one-component system using continuous coding sequences for the genes of interest could suffer from a lack of specificity and therefore secondary, undesirable effects are possible if, for example, gene flow transfers the functional transcriptional unit to a recipient. Furthermore, it cannot be guaranteed that the male fertility is completely restored.

Hence, in a first approach the barnase enzyme was split into two inactive peptides wherein each partial peptide fragment carries at least one active site residue, so that neither peptide has enzyme activity (Burgess et al. (2002) The Plant Journal 31(1): 113-125). The ribonuclease activity is then reconstituted by crossing parents wherein one parent has the first fragment of the barnase enzyme and the other parent has the second fragment of the barnase enzyme. However, the two fragments present in the progeny of these crosses are not linked by peptide bonds. Hence, the barnase activity is not stable at high temperatures and the progeny plants are not suitable for growing in the field.

Further approaches used intein-mediated trans-splicing of proteins to assemble the two fragments of a protein which confers male sterility into one complete polypeptide, wherein both fragments are linked by peptide bonds.

WO 03/102197 A1 describes a process for producing a transgenic multi-cellular plant expressing a trait of interest, e.g. male sterility, with said trait having a controlled distribution of said trait to progeny, wherein a first fragment of a nucleotide sequence encoding said trait is located on a first locus of a nuclear chromosome and a second fragment of a nucleotide sequence encoding said trait is located on a second locus of a nuclear chromosome. Upon crossing the first and the second plant, progeny is created which has the functional trait of interest due to the binding between the protein encoded by said first heterologous nucleotide sequence and the protein encoded by said second heterologous nucleotide sequence. The polypeptides are assembled to a functional protein by intein-mediated trans-splicing of the peptides.

A similar system was also utilized by Gils et al. (2008) Plant Biotechnol. J. 6(3): 226-235 which describe a two-component hybrid system for producing male sterile plants, in which system the coding information for both male sterility and herbicide resistance is divided at two separate loci. Hence, only progeny which inherit both loci will show male sterility and herbicide resistance. However, the operability of this system was only shown in dicotyledonous plants.

Therefore, there is still a need to develop a functional trans-splicing system which works for monocotyledonous plants.

Thus, it is an object of the present invention to provide a method for producing male sterile monocotyledonous plants which remain male sterile at higher temperatures and minimize the risk of transgene escape by strictly controlling the distribution of the transgene to the progeny. This enables the production of a biologically safe transgenic plant which minimizes the undesired transmission of the transgenic trait to other crops. Furthermore, these male sterile monocotyledonous plants may be used in crosses with male fertile plants to produce hybrid plants with superior characteristics.

Another object of the present invention is to provide a process of producing a male sterile transgenic plant, whereby distribution of the male sterility phenotype to the progeny is strictly controlled and occurs with low probability.

These and other objects of the invention are attained by the subject-matter of the independent claims. Advantages and embodiments are defined in the dependent claims.

Hence, the present invention provides a method of producing male sterile monocotyledonous plants, comprising the steps of:

a) introducing into a monocotyledonous plant or plant cell a first expression cassette comprising the following elements in 5' to 3' orientation:
- a tapetum-specific promoter functional in cells of a monocotyledonous plant;
- operatively linked thereto a nucleic acid sequence coding for an N-terminal part of a protein which provides for male sterility;
- a nucleic acid sequence coding for the N-terminal part of a first intein; and
- operatively linked thereto a terminator sequence functional in plant cells;

and b) introducing into said plant or plant cell a second expression cassette comprising the following elements in 5' to 3' orientation:
- a tapetum-specific promoter functional in cells of a monocotyledonous plant;
- operatively linked thereto a nucleic acid sequence coding for a C-terminal part of said first intein
- a nucleic acid sequence coding for at least one copy of a flexible linker sequence;
- a nucleic acid sequence coding for a C-terminal part of said protein which provides for male sterility; and
- operatively linked thereto a terminator sequence functional in plant cells.

A further aspect of the present invention provides a method of producing monocotyledonous hybrid plants, comprising the steps of:
a) producing a male sterile monocotyledonous plant by a method of the present invention and
b) crossing the male sterile monocotyledonous plant of step a) with a male fertile monocotyledonous plant.

In a further aspect, the present invention relates to a transgenic monocotyledonous plant produced by a method of the present invention.

Further, the present invention relates to a transgenic monocotyledonous plant comprising a nucleic acid sequence coding for an N-terminal part of barnase.

In a further aspect, the invention provides a transgenic monocotyledonous plant comprising a nucleic acid sequence coding for a C-terminal part of barnase.

Further, the present invention relates to a transgenic monocotyledonous plant comprising a nucleic acid sequence coding for an N-terminal part of acetolactate synthase.

In a further aspect, the invention provides a transgenic monocotyledonous plant comprising a nucleic acid sequence coding for a C-terminal part of acetolactate synthase.

Further, the present invention relates to a recombinant nucleic acid molecule comprising the following elements:
a) a first expression cassette comprising the following elements in 5' to 3' orientation:
- a tapetum-specific promoter functional in cells of a monocotyledonous plant;
- operatively linked thereto a nucleic acid sequence coding for an N-terminal part of a protein which provides for male sterility;
- a nucleic acid sequence coding for the N-terminal part of a first intein; and
- operatively linked thereto a terminator sequence functional in said plant cells;

and b) a second expression cassette comprising the following elements in 5' to 3' orientation:
- a tapetum-specific promoter functional in cells of a monocotyledonous plant;
- operatively linked thereto a nucleic acid sequence coding for a C-terminal part of said first intein
- a nucleic acid sequence coding for at least one copy of a flexible linker sequence;
- a nucleic acid sequence coding for a C-terminal part of said protein which provides for male sterility; and
- operatively linked thereto a terminator sequence functional in said plant cells.

In still a further aspect, the present invention provides an isolated nucleic acid molecule comprising a nucleic acid sequence according to SEQ ID No. 51 or a fragment of said nucleic acid sequence coding for a functional acetolactate synthase fragment.

Further, the present invention provides an isolated nucleic acid molecule coding for the N-terminal part of an acetolactate synthase, selected from the group consisting of:
a) a nucleic acid sequence according to SEQ ID No. 33 or 53;
b) nucleic acid sequences coding for a protein according to SEQ ID No. 34 or 54 or a functional fragment thereof;
c) nucleic acid sequences hybridising to a complementary strand of the nucleic acid sequence according to SEQ ID No. 33 or 53 under stringent conditions; and
d) nucleic acid sequences which are at least 50% homologous to the nucleic acid sequence shown in SEQ ID No. 33 or 53.

Further, the present invention provides an isolated nucleic acid molecule coding for the C-terminal part of an acetolactate synthase, selected from the group consisting of:
a) a nucleic acid sequence according to SEQ ID No. 43 or 55;
b) nucleic acid sequences coding for a protein according to SEQ ID No. 44 or 56 or a functional fragment thereof;
c) nucleic acid sequences hybridising to a complementary strand of the nucleic acid sequence according to SEQ ID No. 43 or 55 under stringent conditions; and
d) nucleic acid sequences which are at least 50% homologous to the nucleic acid sequence shown in SEQ ID No. 43 or 55.

Finally, the present invention relates to an isolated nucleic acid molecule comprising a nucleic acid sequence according to SEQ ID No. 49 or a fragment of said nucleic acid sequence coding for a functional barnase fragment.

The inventors of the present invention have surprisingly found that a vector which led to a high frequency of male sterile dicotyledonous plants among primary transformants did not produce male sterile plants when introduced into monocotyledonous plants.

Hence, specific adaptations were necessary to use the intein-mediated trans-splicing system in a monocotyledonous plant to induce male sterility. These adaptations mainly involve the use of flexible linker sequences. In preferred embodiments, additionally the nucleic acid sequence coding for the protein which provides for male sterility was adapted to the codon usage of monocotyledonous plants. These specific adaptations led to a high frequency of monocotyledonous plants displaying complete or partial male sterility. The male sterile phenotype was stably inherited and displayed a pronounced robustness against extreme temperature. In general, the vegetative phenotype of the sterile progeny was, under greenhouse conditions, indistinguishable from that of the fertile control plants.

In the process of the invention, the nucleotide sequence encoding a protein which provides for male sterility is split into two fragments, thus obtaining a 5' and a 3' part of the nucleotide sequence. Said 5' part encodes the N-terminal part of the protein which provides for male sterility and said 3' part encodes the C-terminal part of the protein which provides for male sterility.

Said nucleotide sequence is typically a coding sequence (or an open reading frame) of a protein providing male sterility. However, said nucleotide sequence may also contain one or more introns.

To obtain said 5' and 3' part of the nucleotide sequence, said nucleotide sequence is preferably split such that each obtained fragment, upon expression, is incapable of generating a protein which provides for male sterility in the absence of the other fragment. Each fragment contains a sequence portion necessary for the function of the protein providing for male sterility. For example, if said protein is an enzyme, each fragment preferably contains amino acids necessary for catalysis or substrate binding of the enzyme. The protein providing for male sterility may be split into said fragments in many different ways provided that expression of the male sterility requires all said fragments and binding thereof to each other. Structural and functional information known about the protein providing for male sterility may be helpful for finding a suitable splitting site of said nucleotide sequence. In any case, one can easily test experimentally whether a fragment generated by splitting a nucleotide sequence at a randomly chosen site is capable of providing male sterility by expressing the fragment in the tapetum of plants and investigating if these plants are able to develop viable pollen. A further assay for testing the functionality of the fragments is described in example 6, i.e. syringe infiltration of *Nicotiana benthamiana* leaves using *Agrobacterium* containing either an N-terminal part or a C-terminal fragment of the protein and detection of lesions in the leaves. If lesions occur upon infiltration only with the N-terminal or the C-terminal fragment, these fragments are not suitable for use in the method of the present invention.

Expression of male sterility requires the presence of both fragments in the same plant, preferably in the same cells thereof. Expression of male sterility further requires transcription and translation of said first and said second fragment and binding of the translation products of said fragments with peptide bond formation to restore a functional protein.

This peptide bond formation is accomplished by intein-mediated trans-splicing. For this purpose, said first and said second expression cassette further code for inteins capable of mediating protein trans-splicing. By said trans-splicing, the proteins and polypeptides encoded by said first and said second fragments may be linked by peptide bond formation. Trans-splicing inteins may be selected from the nucleolar and organellar genomes of different organisms including eukaryotes, archaebacteria and eubacteria. Inteins that may be used for performing this invention are listed at http://www.neb.com/neb/inteins.html. The nucleotide sequence coding for an intein may be split into a 5' and a 3' part that code for the 5' and the 3' part of the intein, respectively. Sequence portions not necessary for intein splicing (e.g. homing endonuclease domain) may be deleted. The intein coding sequence is split such that the 5' and the 3' parts are capable of trans-splicing. For selecting a suitable splitting site of the intein coding sequence, the considerations published by Southworth et al. (1998) EMBO J. 17: 918-926 may be followed. In constructing the first and the second expression cassette, the 5' intein coding sequence is linked to the 3' end of the first fragment coding for the N-terminal part of the protein which provides for male sterility and the 3' intein coding sequence is linked to the 5' end of the second fragment coding for the C-terminal part of a protein which provides for male sterility.

Herein, peptide bond means the amide linkage between the carboxyl group of one polypeptide and the amino group of another polypeptide.

Within the scope of the present invention, the term "male sterile plants" is intended to mean plants which are unable to produce functional pollen and therefore are unable to self-pollinate. The male sterility enables the controlled breeding to obtain hybrid plants showing the heterosis effect. One can distinguish between nuclear male sterility which is due to a mutation in the nuclear genome and cytoplasmic male sterility which is due to a mutation in the mitochondrial genome.

The term "monocotyledonous plant" is intended to comprise any monocotyledonous plant, preferably agricultural, food or feed plants. More preferably, the monocotyledonous plant is selected from the group consisting of *Hordeum* (barley), *Avena* (oat), *Triticum* (wheat), *Secale* (rye), *Oryza* (rice), *Sorghum* (millet), *Zea* (corn), *Panicum, Pennisetum, Setaria* and others. Other preferred monocotyledonous plants are plants of the genus *Lolium* such as *Lolium multiflorum, Lolium perenne* and *Lolium hybridum*. Most preferably, the monocotyledonous plant is a *Triticum aestivum* plant.

The first and the second expression cassette can be introduced into a monocotyledonous plant or plant cell by various means, e.g. by transformation of a plant or plant cell with two expression vectors, one of which carrying the first expression cassette and the other one carrying the second expression cassette. Alternatively, one expression vector carrying both the first and second expression cassette may be transformed. Further, a plant carrying the first expression cassette may be crossed with a monocotyledonous plant carrying the second expression cassette and the progeny of this cross which contains both the first and the second expression cassette will then be male sterile. The plants carrying the first or the second expression cassette, respectively, have been produced by transformation with the appropriate expression vectors or are progeny of plants produced by such transformation.

Furthermore, the first and the second expression cassette could also be introduced into a plant cell by cell fusion which may be the fusion of germ cells or of somatic cells, wherein one cell carries the first expression cassette and another cell carries the second expression cassette.

For the introduction of DNA into a plant host cell there are a number of well-known techniques available and the person skilled in the art can determine the appropriate method in each case without any problem. These techniques include the transformation of plant cells with T-DNA by using *Agrobacterium tumefaciens* or *Agrobacterium rhizogenes* as a transformation agent, the fusion of protoplasts, the direct gene transfer of isolated DNA into protoplasts, the electroporation of DNA, the introduction of DNA by means of the biolistic method, as well as other possibilities. Thereby, both stable and transient transformants can be generated.

For the injection and electroporation of DNA into plant cells there are no special requirements per se for the plasmids used. The same applies for direct gene transfer. Simple plasmids, such as pUC derivates may be used. If, however, whole plants are to be regenerated from such transformed cells, the presence of a selectable marker gene is necessary. The person skilled in the art is acquainted with the current selection markers, and will have no problem in selecting an appropriate marker. Standard selection markers are those which mediate resistance to a biocide or an antibiotic such as kanamycin, G418, bleomycin, hygromycin, methotrexate, glyphosate, streptomycin, sulfonyl urea, gentamycin or phosphinotricin and suchlike, to the transformed plant cell.

Dependent upon the method of introduction of the desired gene into the plant cell, other DNA sequences may be required. For example, if the Ti or Ri plasmid is used for the transformation of the plant cell, at least the right flanking region, often however the right and the left flanking region of the T-DNA contained in the Ti or Ri plasmid must be linked as a flanking region with the gene to be introduced.

If agrobacteria are used for the transformations, the DNA to be introduced must be cloned in special plasmids, either in an intermediary or in a binary vector. Based on sequences which are homologous to sequences in the T-DNA, the intermediary vectors can be integrated into the Ti or Ri plasmid of the agrobacteria by homologous recombination. This plasmid also contains the vir region necessary for the transfer of the T-DNA. Intermediary vectors cannot replicate in agrobacteria. By means of a helper plasmid, the intermediary vector can be transferred to *Agrobacterium tumefaciens* (conjugation). Binary vectors can replicate in *E. coli* as well as in agrobacteria. They contain a selection marker gene and a linker or polylinker which are framed by the right and left T-DNA border regions. They can be transformed directly into the agrobacteria (Holsters et al. (1978) Molecular and General Genetics 163: 181-187). The *agrobacterium* serving as a host cell should contain a plasmid which carries a vir region. The vir region is necessary for the transfer of the T-DNA into the plant cell. T-DNA can also be present. This type of transformed *agrobacterium* is used for the transformation of plant cells. The use of T-DNA for the transformation of plant cells has been intensively investigated and is described sufficiently in EP 120 515. Both monocotyledonous and dicotyledonous plants or their cells are very accessible to transformation by means of vectors based on agrobacteria (Chan et al. (1993) Plant Mol. Biol. 22: 491-506).

For the transfer of DNA into the plant cell, plant explants can be cultivated specifically for this purpose with *Agrobacterium tumefaciens* or *Agrobacterium rhizogenes*. From the infected plant material (for example, pieces of leaf, stem segments, roots, but also protoplasts or suspension-cultivated plant cells) whole plants can be regenerated in an appropriate medium which can contain antibiotics or biocides for the selection of transformed cells. The regeneration of the plants takes place according to standard regeneration methods and using the common nutrient solutions. The plants and plant cells obtained in this way can be examined for the presence of the DNA introduced.

The person skilled in the art is acquainted with other possibilities for the introduction of foreign DNA using the biolistic method or by protoplast transformation (see L. Willmitzer (1993) Transgenic Plants in: Biotechnology, A Multi-Volume Comprehensive Treatise (publisher: H. J. Rehm et al.), volume 2, 627-659, VCH Weinheim, Germany).

Alternative systems for the transformation of monocotyledonous plants or their cells are transformation by means of the biolistic approach (Wan and Lemaux (1994) Plant Physiol. 104: 37-48; Vasil et al. (1993) Bio/Technology 11: 1553-1558; Ritala et al. (1994) Plant Mol. Bio. 24: 317-325; Spencer et al. (1990) Theor. Appl. Genet. 79: 625-631), protoplast transformation, electroporation of partially permeabilised cells as well as the introduction of DNA by means of glass tissues.

The transformed cells grow within the plant in the normal way (see also McCormick et al. (1986) Plant Cell Reports 5: 81-84). The resulting plants can be raised in the normal way and be crossed with plants which have the same transformed genetic disposition or other genetic dispositions. The resulting hybrid individuals have the respective phenotypical properties.

Two or more generations should be raised in order to ensure that the phenotypical feature remains stable and is inherited. Seeds should be harvested as well so as to ensure that the respective phenotype or other characteristics are maintained.

Similarly, by using the standard methods, transgenic lines can be determined which are homozygous for the expression cassettes of the present invention and their phenotypical characteristics with regard to male sterility is investigated and compared with that from hemizygous lines.

Within the scope of the present invention, the term "expression cassette" means a nucleic acid molecule which contains all elements which are necessary for the expression of a gene, i.e. the gene to be expressed under the control of a suitable promoter and optionally further regulatory sequences such as termination sequences. An expression cassette of the present invention may be part of an expression vector which is transferred into a plant cell or may be integrated into the chromosome of a transgenic plant after transformation. The terms "first expression cassette", "second expression cassette", "third expression cassette" and "fourth expression cassette" are only used to distinguish the different expression cassettes comprising different elements, but are not intended to indicate any spatial relationship or order between the expression cassettes, i.e. the second expression cassette may be located 5' of the first expression cassette within an expression vector or a chromosome.

Preferably, the expression vector is selected from the group consisting of plasmids, cosmids, (recombinant) viruses and other vectors known in the field of gene technology, with which nucleic acid molecules can be transferred to plants or plant cells. The term "vector" also comprises so-called minochromosomes which are linear or circular DNA fragments which contain centromer sequences of the respective plant in addition to the transgene. Minichromosomes are stable in the nucleus and are passed on to the daughter cells during cell division. They are transferred by standard methods of transformation. Most preferably, the vector is selected from the group consisting of pBR322, pUC vectors, M13mp vectors or vectors being derived from the Ti plasmid or the Ri plasmid of agrobacteria.

In order to prepare the introduction of foreign genes into higher plants or the cells of the same, a large number of cloning vectors are available which contain a replication signal for *E. coli* and a marker gene for the selection of transformed bacterial cells. Examples of such vectors are pBR322, pUC series, M13mp series, pACYC184, etc. The required sequence can be introduced into the vector at an appropriate restriction site. The plasmid obtained is used for the transformation of *E. coli* cells. Transformed *E. coli* cells are cultivated in an appropriate medium, and finally harvested and lysed. The plasmid is recovered. As an analysis method for characterizing the plasmid DNA obtained, methods such as restriction analyses, gel electrophoreses and other biochemical/molecular biological methods are generally used. Following each manipulation the plasmid DNA can be cleaved and the DNA fragments obtained can be combined with other DNA sequences. Each plasmid DNA sequence can be cloned into the same or other plasmids. Standard cloning methods can be taken from Sambrook et al., 2001 (Molecular cloning: A laboratory manual, $3^{rd}$ edition, Cold Spring Harbor Laboratory Press).

The term "tapetum-specific promoter" within the meaning of the present invention is understood to mean that a nucleic acid sequence under the control of a tapetum-specific promoter region is expressed in the tapetum of plants. Particularly, a promoter is also tapetum-specific within the meaning of the present invention if the promoter region preferentially leads to the expression of the nucleic acid sequence in the tapetum in comparison to other cell types and leads to a significantly increased expression such as at least two-fold, preferably at least five-fold and particularly preferably at least ten-fold and most preferably at least fifty-fold increased expression in tapetum in comparison to other cell types. The expression of a nucleic acid sequence in different tissues and organs can be determined with in situ detection techniques known to the person skilled in the art. For example, a reporter gene such as β-glucuronidase may be expressed under the control of the promoter to be investigated and the activity of the reporter gene in different organs may be determined.

The term "tapetum" is known to the expert and is intended to mean the highly specialized, transient tissue surrounding the (micro-)spores and/or pollen grains during their development. Supplementary information can be derived from any plant anatomy or plant physiology book such as Strassburger, Lehrbuch der Botanik, 35. Auflage 2002, Spektrum Akademischer Verlag.

Suitable tapetum-specific promoters are known to the person skilled in the art and include the promoter of the rice osg6b gene (Tsuchiya et al. (1995) Plant Cell Physiol. 36: 487-494), the pca55 promoter from corn (WO 92/13956) and the pE1 and pT72 promoters from rice (WO 92/13957). Preferably, the tapetum-specific promoter is the promoter from the rice osg6B gene. However, the tapetum-specific promoter of the present invention does not have to be derived from a monocotyledonous plant, but can also be isolated from a dicotyledonous plant, as long as the promoter is functional in cells of a monocotyledonous plant, i.e. as long as it is capable of directing tapetum-specific expression of nucleic acid sequences operatively linked thereto in monocotyledonous plants.

The "protein which provides for male sterility" may be any protein the expression of which in the tapetum leads to male sterile plants by interfering with the function and development of pollen. Examples of such genes include RNases, ribosomal inhibitor proteins (Cho et al. (2001) Mol. Cells. 11: 326-333), sucrose isomerase (WO 01/59135), protease and glucanase (Tsuchiya et al. (1995) Plant Cell Physiol. 36: 487-494). Preferably, the protein which provides for male sterility is an RNase. Examples for RNases are barnase (Mariani et al. (1990) Nature 347: 737-741; Mariani et al. (1992) Nature 357: 384-387), RNase T1 from *Aspergillus oryzae* (Denis et al. (1993) Plant Physiol. 101: 1295-1304) and rat pancreatic ribonuclease (Bernd-Souza et al. (2000) Genet. Mol. Biol. 23(2) 435-443).

Even more preferably, the protein which provides for male sterility is barnase, i.e. ribonuclease from *Bacillus amyloliquefaciens*. The amino acid sequence of barnase from *Bacillus amyloliquefaciens* is shown in SEQ ID No. 2 and the native nucleic acid sequence coding for barnase is depicted in SEQ ID No. 1.

Preferably, the nucleic acid sequences coding for the N- and the C-terminal part of barnase are adapted to the codon usage of monocotyledonous plants, more preferably to the codon usage of *Triticum aestivum*. The nucleic acid sequence coding for the barnase which is adapted to the codon usage of *Triticum aestivum* is shown in SEQ ID No. 49.

To obtain said 5' and 3' part of the nucleotide sequence coding for barnase, said nucleotide sequence is preferably split such that each obtained fragment, upon expression, is incapable of generating a functional barnase protein in the absence of the other fragment. Each barnase fragment contains a sequence portion necessary for the barnase function. The barnase may be split into said fragments in many different ways provided that expression of the male sterility requires all said fragments and binding thereof to each other. One can easily test experimentally whether a fragment generated by splitting the barnase nucleotide sequence at a randomly chosen site is capable of providing male sterility by expressing the fragment in the tapetum of plants and investigating if these plants are able to develop viable pollen. A further assay for testing the functionality of the fragments is described in example 6 of this application. Preferably, the barnase is split into said fragments in the amino acid region between amino acid residues 30 and 40 of the mature protein, i.e. between amino acids 30 and 31, 31 and 32, 32 and 33, 33 and 34, 34 and 35, 35 and 36, 36 and 37, 37 and 38, 38 and 39 or 39 and 40 of the amino acid sequence according to SEQ ID No. 50.

More preferably, the N-terminal part of the barnase comprises 36 amino acids, and the C-terminal part of the barnase comprises 75 amino acids. Alternatively, the N-terminal part of barnase may comprise 35 amino acids if no methionine is added to the N-terminus.

Most preferably, the N-terminal part of the barnase is encoded by a nucleic acid sequence according to SEQ ID No. 3 or 13 and the C-terminal part of the barnase is encoded by a nucleic acid sequence according to SEQ ID No. 5 or 27. The N-terminal part of the barnase preferably has the amino acid sequence according to SEQ ID No. 4 or 14 and the C-terminal part of the barnase preferably has the amino acid sequence according to SEQ ID No. 6 or 28.

However, the invention is also intended to comprise smaller fragments of the barnase protein or "functional barnase fragments", as long as the N- and the C-terminal parts of such fragment restore a functional, enzymatically active protein upon intein-mediated trans-splicing which protein leads to male sterility when expressed in the tapetum of plants. For example, the C-terminal part may lack one or more amino acid residues at its C-terminus and/or the N-terminal part may lack one or more amino acid residues at its N-terminus. Upon intein-mediated trans-splicing a protein smaller than the wild-type protein is formed from the two fragments which protein is functional and enzymatically active. However, also deletions within the N- and/or the C-terminal part of barnase are conceivable as long as they do not affect the ability of the N- and the C-terminal part to restore a functional protein.

The term "operatively linked" is understood to denote that the sequences linking the different nucleic acids used are selected in such a way that the function of the respectively linked nucleic acid segment is maintained. In case, for example, the nucleotide sequence coding for the N- or C-terminal part of the protein which provides for male sterility is to be expressed in a cell, it has to be observed that no sequences which would lead to a termination of the transcription are located between the promoter sequence and the nucleotide sequence coding for the N- or C-terminal part of the protein which provides for male sterility.

The "termination sequences" are sequences which ensure that the transcription or the translation is properly terminated. If the transferred nucleic acids are to be translated, the termination sequences are typically stop codons and corresponding regulatory sequences; if the transferred nucleic acids are only to be transcribed, they are generally poly-A sequences. Preferably, the termination sequence is selected from the octopine synthase terminator and the nopaline synthase terminator (Jones et al. (1992) Transgenic Res. 1: 285-297).

The "flexible linker sequence" within the scope of the present invention is a short flexible peptide which is used to bridge the N- and the C-terminal part of the protein which provides for male sterility without serious steric interference. The flexible linker sequence brings the two splice junctions in close proximity and helps to precisely align all reacting groups. Hence, efficient splicing is supported (Chong and Xu (1997) J. Biol. Chem. 272: 15587-15590). The most widely used linker designs have sequences consisting essentially of stretches of glycine (G) and serine (S) residues, because hydrophilic amino acids allow hydrogen bonding to the solvent and glycines provide the necessary flexibility. These properties prevent the penetration of the linker peptide into the hydrophobic interface formed in the association of the domains. Furthermore, the linkers are not able to form an ordered secondary structure. The term "essentially consist of glycine and serine residues" is intended to mean that at least 60% or 65%, preferably 70% or 75%, more preferably 80%, 82%, 84%, 86% or 88%, even more preferably 90%, 92%, 93%, 94%, 95%, 96%, 97%, 98% or 99% of the amino acid residues within the flexible linker sequence are glycine and/or serine residues. Most preferably, all amino acid residues within the flexible linker sequence are glycine and/or serine residues.

The length of the linker sequences should be selected such that the linker peptides are too short to allow pairing of the domains of the same amino acid chain, but favour pairing between domains in two adjacent chains. Thus, the length of the linker sequence may be 1 to 20 amino acids, preferably 2 to 15 amino acids, more preferably 3 to 10 amino acids, even more preferably 4 to 8 amino acids and most preferably 5 amino acids.

Most preferably, the flexible linker sequence has the amino acid sequence GGGGS.

The flexible linker sequence is present in at least one copy, preferably 1 to 5 copies, more preferably 2 to 4 copies and most preferably three copies. If multiple copies of the flexible linker sequence are used every copy is preferably encoded by different codons to avoid interference.

The tapetum-specific promoter used in the second expression cassette may be the same as the one used in the first expression cassette or it may be different from the promoter used in the first expression cassette, preferably the same tapetum-specific promoter is used in the first and the second expression cassette to achieve equimolar expression of the N- and the C-terminal fragments.

"Inteins" are proteins that are able to catalyze trans-splicing events between separate protein fragments as they are able to excise themselves from precursor molecules and ligate the flanking protein sequences in a process termed protein-splicing (Southworth et al. (1998) EMBO J. 17: 918-926; Wu et al. (1998) Proc. Natl. Acad. Sci. USA 95: 9226-9231; Saleh and Perler (2006) Chem. Rec. 6: 183-193; Perler (1998) Cell 92: 1-4). At present, more than 400 inteins are known. They are distributed among the genomes of different organisms including eukaryotes, archaebacteria and eubacteria. An overview of the currently available inteins is given by the homepage http://tools.neb.com/inbase/index.php (inbase, the intein database (Perler (2002) Nucleic Acids Res. 30: 383-384)).

Preferably, the first intein is selected from the group consisting of DnaB and DnaE, both from the green-blue algae of *Synechocystis* spec. More preferably, the first intein is DnaB and most preferably, the first intein is encoded by a nucleic acid sequence according to SEQ ID No. 7 or has the amino acid sequence according to SEQ ID No. 8. The nucleic acid sequence coding for the N-terminal part of DnaB is depicted in SEQ ID No. 9 and the nucleic acid sequence coding for the C-terminal part of DnaB is shown in SEQ ID No. 11.

In a preferred embodiment of the present invention, the nucleic acid sequences coding for the N- and the C-terminal part of the protein which provides for male sterility and the nucleic acid sequences coding for the N- and the C-terminal part of the first intein are adapted to the codon usage of monocotyledonous plants.

If, for example, the nucleic acid or the first and the second expression cassette are to be introduced into a wheat plant, the codon usage is adapted to the codon usage of the wheat plant, if the first and the second expression cassette are introduced into a rye plant, the nucleic acid sequences are adapted to the codon usage of the rye plant.

However, the use of a nucleic acid sequence the codon usage of which has been adapted to the codon usage in wheat may also have advantages in monocotyledonous plant species closely related to wheat, such as rye or barley.

Preferably, the nucleic acid sequences coding for the N- and the C-terminal part of the protein which provides for male sterility and the nucleic acid sequences coding for the N- and the C-terminal part of the first intein are adapted to the codon usage of Triticeae, more preferably they are adapted to the codon usage of plants of the genus *Triticum* and most preferably they are adapted to the codon usage in *Triticum aestivum*.

The genetic code is redundant, as 20 amino acids are specified by 61 triplet codons. Thus, most of the 20 proteinogenic amino acids are coded by several base triplets (codons). However, the synonymous codons which specify an individual amino acid are not used with the same frequency in a specific organism, but there are preferred codons, which are used frequently, and codons which are used less frequently. Said differences in codon usage may be due to selective evolutionary pressures, and, in particular, to the efficiency of translation. One reason for the lower translation efficiency of rarely occurring codons could be that the corresponding aminoacyl-tRNA pools are depleted and are therefore no longer available for protein synthesis.

Furthermore, different organisms prefer different codons. Thus, for example, the expression of a recombinant DNA originating from a mammalian cell often proceeds only suboptimally in *E. coli* cells. Therefore, the replacement of infrequently used codons by frequently used codons can enhance expression in some cases.

The DNA sequence of a larger number of genes of many organisms is known and there are tables, from which the frequency of the usage of specific codons in the respective organism can be taken. With the aid of said tables, protein sequences can be relatively exactly back-translated to form a DNA sequence, which contains the codons preferred in the respective organism for the different amino acids of the protein. Tables for codon usage can, inter alia, be found at the following internet address: http://www.kazusa.or.jp/codon/index.html. There are programs available also for reverse translation of a protein sequence, for example the amino acid sequence of barnase, to form a degenerate DNA sequence, like for instance at http://www.entelechon.com/bioinformatics/backtranslation.php; or http://www.hgmp.mrc.ac.uk/Software.EMBOSS/Apps/backtranseq.html.

The optimized nucleic acid sequence coding for the N-terminal part of the barnase is shown in SEQ ID No. 13 and the nucleic acid sequence coding for the C-terminal part of the barnase is shown in SEQ ID No. 27. Further, the optimized nucleic acid sequence coding for the N-terminal part of the DnaB intein is shown in SEQ ID No. 17 and the optimized nucleic acid sequence coding for the C-terminal part of the DnaB intein is shown in SEQ ID No. 19.

Preferably, stretches containing exon sequences are inserted between the nucleic acid sequences coding for the C-terminal part of the intein and the C-terminal part of the protein which provides for male sterility and between the N-terminal part of the protein which provides for male sterility and the N-terminal part of the intein. As protein-splicing is dependent on the chemical nature of the splice-site junction amino acids, the insertion of stretches containing exon sequences is supposed to increase the efficiency of protein trans-splicing (Sun et al. (2001) Appl. Environ. Microbiol. 67: 1025-1029). Thus, the inserted exon sequences provide the parts of the exteins which are advantageous for the function of the corresponding intein.

Hence, preferably the first expression cassette comprises a nucleic acid sequence coding for an amino acid sequence comprising the amino acid sequence RESG or fragments of said sequence from the DnaB extein and the second expression cassette comprises a nucleic acid sequence coding for an amino acid sequence comprising an amino acid sequence selected from the group consisting of SEEQDHG and SIEQD or fragments of said sequences. Preferably, the second expression cassette comprises a nucleic acid sequence coding for an amino acid sequence comprising the amino acid sequence SIEQD or fragments of said sequence. "Fragments of the RESG extein sequence" may be for example ESG or SG. "Fragments of the SIEQD extein sequence" may be for example IEQD, EQD or QD. "An amino acid sequence comprising the amino acid sequence RESG" or "an amino acid sequence comprising an amino acid sequence selected from the group consisting of SEEQDHG and SIEQD" may be an amino acid sequence with one or more amino acid residues in addition to the RESG, SEEQDHG and SIEQD sequence, respectively. Preferably, the one or more additional amino acid residues are located in the N-terminus of the RESG, SEEQDHG and SIEQD sequence, respectively.

In a further preferred embodiment, the first and the second expression cassette do not comprise any nucleic acid sequences coding for amino acids other than the above mentioned, i.e. the N- and the C-terminal part of the protein which provides for male sterility, the N- and the C-terminal part of the first intein and the nucleic acid sequence coding for at least one copy of the flexible linker sequence as well as optionally sequences from the extein sequence as described above. Particularly, any amino acids that have been inserted into the original vector as a result of the cloning strategies and that are not present in the native amino acid sequence of the protein which provides for male sterility are removed. These are the amino acid residues D and V between the N-terminal part of the protein which provides for male sterility and the N-terminal part of the first intein.

In one embodiment of the present invention, a nucleic acid sequence coding for a protein which is a phenotypical marker is introduced into said plants together with the first and the second expression cassette. "A protein which is a phenotypical marker" is intended to mean a protein the expression of which leads to a property of the plant which allows the identification of plants that have been transformed with the nucleic acid sequence coding for the phenotypical marker. Suitable phenotypical markers are for example proteins conferring herbicide resistance, proteins involved in anthocyanin synthesis or reporter proteins such as glucuronidase, luciferase and green fluorescent protein. Preferably, the phenotypical marker is a protein which confers herbicide resistance.

The protein which confers herbicide resistance can be used for the selection of plants which contain both the N- and the C-terminal part of the protein which provides for male sterility. The protein which confers herbicide resistance may be selected from the group consisting of acetolactate synthase, 5-enolpyruvylshikimate-3-phosphate synthase, phosphinotricin acetyl transferase (BAR), betainaldehyde dehydrogenase (BADH), dihydrofolate reductase (DFR1) and glyphosate oxidoreductase.

Preferably, the protein which confers herbicide resistance is acetolactate synthase which is the first enzyme in the synthesis of branched chain amino acids. This protein can be engineered to confer resistance to sulphonylureas and imidazolinones (Tan et al. (2005) Pest Manag Sci. 61: 246-257). Preferably, the acetolactate synthase gene is derived from rice (GeneBank Accession No. AP008208, Oryza sativa; japonica cultivar group; genomic DNA, chromosome 2, position 18335903-18337834) and has been engineered according to the teachings in Tan et al. (2005) Pest Manag Sci. 61: 246-257 to confer resistance to sulphonylureas and imidazolinones. Most preferably, a mutation of tryptophane to leucin was introduced on position 548 so that the protein is able to confer herbicide resistance. However, also other mutations on other positions are conceivable, for example a tryptophane to serine mutation on position 548.

Preferably, the nucleic acid sequence coding for the acetolactate synthase is selected from the group consisting of:
a) a nucleic acid sequence according to SEQ ID No. 31 or 51;
b) nucleic acid sequences coding for a protein according to SEQ ID No. 32 or 52 or a functional fragment thereof;
c) nucleic acid sequences hybridizing to a complementary strand of the nucleic acid sequence according to SEQ ID No. 31 or 51 under stringent conditions; and
d) nucleic acid sequences which are at least 50% homologous to the nucleic acid sequence shown in SEQ ID No. 31 or 51.

More preferably, the protein encoded by the nucleic acid sequence comprises a mutation that confers herbicide resistance. Most preferably, the mutation is a tryptophan to leucine mutation on position 548 of the amino acid sequence according to SEQ ID NO. 32 or 52 or a tryptophan to serine mutation on position 548 of the amino acid sequence according to SEQ ID NO. 32 or 52.

According to the present invention, the term "homologous" is generally understood to denote that the nucleic acid or amino acid sequence of a DNA molecule or of a protein is identical to the nucleic acid or amino acid sequences of acetolactate synthase or functionally equivalent parts thereof by at least 50%, preferably by at least 55%, further preferably by at least 60%, also preferably by at least 70%, 80% or 85%, especially preferably by at least 90%, 91%, 92% or 93%, particularly preferably by at least 94%, 95%, 96% or 97% and most preferably by at least 98% or 99%. Preferably, homology is determined over the entire sequence length of acetolactate synthase.

"Identity of two proteins" is understood to denote the identity of the amino acids over a particular protein region, preferably over the entire protein length, in particular the identity calculated by comparison with the aid of the Lasergene software by DNA Star Inc., Madison, Wis. (USA) using the CLUSTAL method (Higgins et al. (1989) Comput. Appl. Biosci. 5 (2): 151).

Nucleic acid molecules are identical if they have identical nucleotides in the same 5' to 3' order.

Thus, homology is preferably calculated over the entire amino acid or nucleic acid sequence region. Besides the programs mentioned above, the person skilled in the art knows further programs based on different algorithms for comparing different sequences. Herein, the algorithms by Needleman and Wunsch, or Smith and Waterman yield particularly reliable results. For said sequence comparisons, for example, the program PileUp (Feng and Doolittle, J. Mol. Evolution. (1987) 25: 351-360; Higgins et al. (1989) CABIOS 5: 151-153) or the programs Gap and Best Fit (Needleman and Wunsch (1970) J. Mol. Biol. 48: 443-453 and Smith and Waterman (1981) Adv. Appl. Math. 2: 482-489), which are contained in the GCG Software Package by the Genetics Computer Group (575 Science Drive, Madison, Wis., USA 53711), can also be used.

The Clustal W program, as can be called up at http://www.ebi.ac.uk/clustalw, was used for the sequence alignments conducted within the scope of the present invention. The parameters of said default homepage remained unaltered for the alignments.

A further object of the present invention are nucleic acid molecules, which hybridize under stringent conditions with, or are substantially complementary to, those nucleic acid molecules coding for acetolactate synthase or functionally equivalent parts thereof. The term "complementarity" describes the capability of a nucleic acid molecule of hybridizing with another nucleic acid molecule due to hydrogen bonds formed between complementary bases. The person skilled in the art is aware of the fact that two nucleic acid molecules do not have to have a 100% complementarity in order to be able to hybridize with each other. Preferably, a nucleic acid sequence, which is supposed to hybridize with another nucleic acid sequence, is complementary to the latter by at least 40%, by at least 50%, by at least 60%, preferably by at least 70%, especially preferably by at least 80%, also especially preferably by at least 90%, particularly preferably by at least 95%, and most preferably by at least 98% or 100%.

Stringent in vitro hybridization conditions are known to the person skilled in the art and can be taken from the literature (see, for example, Sambrook et al., vide supra). The term "specific hybridization" relates to the fact that a molecule preferably binds to a specific nucleic acid sequence under stringent conditions, provided that said nucleic acid sequence is part of a complex mixture of, for example, DNA or RNA molecules.

Thus, the term "stringent conditions" relates to conditions, under which a nucleic acid sequence preferably binds to a target sequence, but not, or at least in a significantly reduced manner, to other sequences.

Stringent conditions are dependent on the circumstances. Longer sequences hybridize specifically at higher temperatures. In general, stringent conditions are selected in such a way that the hybridization temperature is about 5° C. below the melting point ($T_m$) for the specific sequence at a defined ionic strength and a defined pH value. $T_m$ is the temperature (at a defined pH value, a defined ionic strength, and a defined nucleic acid concentration), at which 50% of the molecules, which are complementary to a target sequence, hybridize with said target sequence. Typically, stringent conditions comprise salt concentrations between 0.01 and 1.0 M sodium ions (or ions of another salt) and a pH value between 7.0 and 8.3. The temperature is at least 30° C. for short molecules (for example, for those comprising between 10 and 50 nucleotides). In addition, stringent conditions may comprise the addition of destabilizing agents, like for example formamide. Typical hybridization and washing buffers are of the following composition.

| | |
|---|---|
| Pre-hybridization solution: | 0.5% SDS |
| | 5 x SSC |
| | 50 mM NaPO$_4$, pH 6.8 |
| | 0.1% Na pyrophosphate |
| | 5 x Denhardt's Reagent |
| | 100 µg/ml salmon sperm |
| Hybridization solution: | Pre-hybridization solution |
| | 1 x 10$^6$ cpm/ml probe (5-10 min, 95° C.) |
| 20 x SSC: | 3M NaCl |
| | 0.3M sodium citrate |
| | ad pH 7 with HCl |

-continued

| | |
|---|---|
| 50 x Denhardt's Reagent: | 5 g Ficoll |
| | 5 g polyvinyl pyrrolidone |
| | 5 g Bovine Serum Albumin |
| | ad 500 ml A. dest. |

A typical hybridization procedure is conducted as follows:

| | | |
|---|---|---|
| Optional: | washing the blot 30 min in 1 x SSC/0.1% SDS at 65° C. | |
| Pre-hybridization: | at least 2 h at 50-55° C. | |
| Hybridization: | overnight at 55-60° C. | |
| Washing: | 5 min 2 x SSC/0.1% SDS | Hybridization temp. |
| | 30 min 2 x SSC/0.1% SDS | Hybridization temp. |
| | 30 min 1 x SSC/0.1% SDS | Hybridization temp. |
| | 45 min 0.2 x SSC/0.1% SDS | 65° C. |
| | 5 min 0.1 x SSC | Room temp. |

The term "functional fragment of a protein which confers herbicide resistance" or "functionally equivalent parts of a protein which confers herbicide resistance" is intended to mean that the fragment of the protein is still able to confer herbicide resistance when expressed in plants.

The protein which confers herbicide resistance is expressed under the control of a promoter which is functional in cells of a monocotyledonous plant. As described above with respect to the tapetum-specific promoter, this promoter does not have to be derived from a monocotyledonous plant as long it can govern the expression of a nucleic acid sequence operatively linked thereto in cells of a monocotyledonous plant. Preferably, constitutive promoters such as the 35S promoter, the actin promoter or the ubiquitin promoter are used, however, other promoters can of course be used which are obtainable from different sources such as plants or plant viruses or fungi and which are suitable for the expression of genes in monocotyledonous plants. The choice of promoter and other regulatory sequences determines the local and temporal expression pattern of the gene of the protein which confers a herbicide resistance. Besides constitutive promoters, also tissue-specific promoters such as the phosphoenolpyruvate promoter or the fructose-1,6-bisphosphatase promoter or inducible promoters are conceivable. Preferably, the protein conferring herbicide resistance is expressed under the control of a rice actin1 promoter (McElroy et al. (1990) Plant Cell 2: 163-171).

In a preferred embodiment of the present invention, the nucleic acid sequence coding for the protein which is a phenotypical marker is also adapted to the codon usage of monocotyledonous plants. More preferably, the codon usage is adapted to the codon usage of the plant into which the first and the second expression cassette are introduced, preferably to the codon usage of Triticeae, even more preferably to the codon usage of the genus *Triticum* and most preferably to the codon usage of *Triticum aestivum*.

In one embodiment of the present invention the protein which confers herbicide resistance is also split into two fragments which are assembled to a functional protein by intein-mediated trans-splicing.

It has already been shown that functional acetolactate synthase and functional 5-enolpyruvylshikimate-3-phosphate synthase (EPSPS) can be reconstituted from two separate fragments using the DnaE intein from *Synechocystis* spec. (Sun et al. (2001) Appl. Environ. Microbiol. 67: 1025-1029; Chen et al. (2001) Gene 263: 39-48; Chin et al. (2003) Proc. Natl. Acad. Sci. USA 100: 4510-4515).

Hence, a third and a fourth expression cassette are introduced into a monocotyledonous plant in addition to the first and the second expression cassette. The third expression cassette comprises the following elements in 5' to 3' orientation:

- a promoter functional in cells of a monocotyledonous plant;
- operatively linked thereto a nucleic acid sequence coding for an N-terminal part of a protein which confers herbicide resistance;
- a nucleic acid sequence coding for the N-terminal part of the second intein; and
- optionally, operatively linked thereto a terminator sequence functional in said plant cells.

The fourth expression cassette comprises the following elements in 5' to 3' orientation:

- a promoter functional in cells of a monocotyledonous plant;
- operatively linked thereto a nucleic acid sequence coding for the C-terminal part of said second intein;
- a nucleic acid sequence coding for a C-terminal part of said protein which confers herbicide resistance; and
- optionally, operatively linked thereto a terminator sequence functional in said plant cells.

Thus, the expression from the third and the fourth expression cassette will restore a herbicide resistance gene upon trans-splicing catalysed by the second intein.

Preferably, the protein which confers herbicide resistance is acetolactate synthase (ALS). More preferably, the acetolactate synthase is split into said fragments in the amino acid region between amino acid residues 400 and 410 of the mature protein according to SEQ ID NO. 32 or 52, i.e. between amino acids 400 and 401, 401 and 402, 402 and 403, 403 and 404, 404 and 405, 405 and 406, 406 and 407, 407 and 408, 408 and 409 or 409 and 410 of the amino acid sequence according to SEQ ID No. 52 or 52. Most preferably, the N-terminal part of the acetolactate synthase has 403 amino acids and the C-terminal part of the acetolactate synthase has 421 amino acids.

Preferably, stretches containing exon sequences are inserted between the nucleic acid sequences coding for the C-terminal part of the second intein and the C-terminal part of the protein which is a phenotypical marker and between the N-terminal part of the protein which is a phenotypical marker and the N-terminal part of the second intein. These exon sequences provide the parts of the extein which are advantageous for the function of the intein. Hence, preferably the third expression cassette comprises a nucleic acid sequence coding for an amino acid sequence comprising the amino acid sequence DVKFAEY or fragments of said sequence from the DnaE extein and the second expression cassette comprises a nucleic acid sequence coding for an amino acid sequence comprising the amino acid sequence CFNHG or fragments of said sequence. "Fragments of the DVKFAEY extein sequences" may be for example VKFAEY, KFAEY, FAEY, AEY or EY. "Fragments of the CFNHG extein sequences" may be for example FNHG, NHG and HG. "An amino acid sequence comprising the amino acid sequence DVKFAEY" or "an amino acid sequence comprising the amino acid sequence CFNHG" may be an amino acid with one or more amino acid residues in addition to the DVKFAEY or CFNHG sequence, respectively. Preferably, the one or more amino acid residues in addition are located on the N-terminus of the DVKFAEY or CFNHG sequence, respectively.

Preferably, the fourth expression cassette further comprises a nucleic acid sequence coding for at least one copy of a flexible linker sequence which nucleic acid sequence is located between the nucleic acid sequence coding for the C-terminal part of said second intein and the nucleic acid sequence coding for a C-terminal part of said protein which is a phenotypical marker. The flexible linker is defined as above with respect to the second expression cassette.

Some proteins which are phenotypical markers, such as acetolactate synthase, are expressed in the cytosol and transported to the chloroplast via an N-terminal signal sequence. Hence, for targeting the C-terminal part of said proteins fused to the C-terminal part of the second intein to the chloroplast, an artificial chloroplast targeting sequence has to be fused to this fusion protein. Preferably, the artificial chloroplast targeting sequence has the amino acid sequence MASSMLSSAAVVATRASAAQASMVAPFT-GLKSAASFPVTRKQNNLDITSIAS NGGRVQCA or is a functional fragment thereof which is still capable of directing the transport of proteins to the chloroplast.

The second intein the N- and the C-terminal part of which are present in the third and the fourth expression cassette, respectively, is other than the first intein the N- and the C-terminal part of which is present in the first and second expression cassette so that the first and the second intein do not cross-react with each other and do not lead to mis-spliced products due to the universal nature of interaction between the intein parts. This means that for example if a DnaB is used as the first intein, DnaE is used as the second intein and vice versa.

In one embodiment of the present invention the first, the second, the third and the fourth expression cassette are all located on the same expression vector. Preferably, the expression vector comprises a first part comprising the first expression cassette and the third or fourth expression cassette, and a second part comprising the second expression cassette and the third (if the first part comprises the fourth expression cassette) or fourth expression cassette (if the first part comprises the third expression cassette). More preferably, both the first part and the second part are flanked by recombinase recognition sites.

A "recombinase" is an enzyme which catalyzes a recombination process. In particular, the recombinase recognizes certain nucleic acid sequences, the so called "recombinase recognition sites", and leads to a recombination of these sites. One recombinase which could be used for catalyzing a recombination is the *Streptomyces* phage PhiC31 integrase which catalyzes the irreversible recombination between attB and attP recognition sites. The site-specific recombination between these sites leads to the deletion of sequences located between the participating recombinase recognition sites.

In an embodiment of the present invention, an expression vector comprising a first part comprising the first expression cassette and the third or fourth expression cassette, and a second part comprising the second expression cassette and the third (if the first part comprises the fourth expression cassette) or fourth expression cassette (if the first part comprises the third expression cassette), wherein both the first part and the second part are flanked by recombinase recognition sites is first introduced into a plant to form a pro-locus. Upon crossing said plants carrying the pro-locus with a plant expressing a site-specific recombinase such as *Streptomyces* phage PhiC31, the recombinase will catalyze the irreversible site-specific recombination between the recombinase recognition sites and derivative loci will be obtained which contain either the first or the second part. For example, a first derivative locus contains a nucleic acid sequence coding for the N-terminal part of the protein which provides for male sterility and a nucleic acid sequence coding for the N-terminal part of a protein which confers herbicide resistance and a second derivative locus contains a nucleic acid sequence coding for the C-terminal part of the protein which provides for male sterility and the C-terminal part of the protein which confers herbicide resistance. Furthermore, the first and the second derivative locus are located on identical loci on homologous chromosomes, i.e. they are "linked in repulsion". For example in diploid plants, this means that one derivative locus is located on locus X on chromosome Y and the other derivative locus is located on locus X' on the other chromosome Y'. However, the processes of the present invention may not only be applied to diploid plants, but also to polyploid plants. "Identical loci" are loci between which no recombination is possible. A scheme for the production of the pro-locus and the derivative loci is shown in FIG. 8.

In another embodiment of the present invention, the protein which confers herbicide resistance is not split. The first part of the expression vector then comprises either the nucleic acid sequence coding for the N-terminal part of the protein which provides for male sterility alone or together with the nucleic acid sequence coding for the full-length protein which confers herbicide resistance. The second part of the expression vector comprises either the nucleic acid sequence coding for the C-terminal part of the protein which provides for male sterility alone or together with the nucleic acid sequence coding for the full-length protein which confers herbicide resistance (if the latter nucleic acid sequence is not present in the first part). Upon recombination, two derivative loci will be formed. One of these derivative loci will then contain the nucleic acid sequence coding for the full-length protein which confers herbicide resistance together with either the nucleic acid sequence coding for the N-terminal part of the protein which provides for male sterility or the nucleic acid sequence coding for the C-terminal part of the protein which provides for male sterility, while the other derivative locus only contains either the nucleic acid sequence coding for the N-terminal part of the protein which provides for male sterility or the nucleic acid sequence coding for the C-terminal part of the protein which provides for male sterility.

In one embodiment of the present invention the male sterile plants are selected by applying a suitable herbicide, i.e. a herbicide against which the plants may be resistant by expression of the protein which confers herbicide resistance, to said plants. Only the plants which contain a functional protein which confers herbicide resistance to said plants will survive the selection. If the protein which confers herbicide resistance is acetolactate synthase, the herbicide used for selection of the plants may be selected from the groups of sulphonylureas and imidazolinones, such as primisulphuronmethyl or imazethapyr.

The present invention further relates to a method of producing monocotyledonous hybrid plants, comprising the steps of:
a) producing a male sterile monocotyledonous plant by a method described above; and
b) crossing the male sterile monocotyledonous plant of step a) with a male fertile monocotyledonous plant.

"Hybrid plants" are plants which are the progeny of two genetically unidentical parents. Hybrid plants are produced by cross-pollination of genetically different parental lines. As the plants of the present invention are male sterile, the self-pollination of these plants is avoided and it is possible to perform directed crosses with a selected male fertile parent. The term "male fertile parent" means that this parent is able to produce functional pollen which can be used to pollinate the female sexual organs of the male sterile plant.

In the process of the present invention, the hybrid seeds produced may be 100% fertile, as either only the N-terminal fragment or only the C-terminal fragment of the protein which provides for male sterility is expressed in the progeny. The male fertile plant used for producing the hybrid plants should not contain a fragment of a nucleotide sequence encoding the protein which provides for male sterility and, optionally, not contain a fragment of a nucleotide sequence encoding the protein which confers herbicide resistance.

The hybrid seed growing on the hybrid plants may then be harvested.

"Transgenic plants" and "transgenic plant cells" can be any monocotyledonous plant or plant cell, preferably agricultural plants or cells from agricultural plants, into which a nucleic acid molecule or at least one expression cassette has been introduced. These plants can be produced by any of the methods which have been described herein. The invention is further directed to transgenic parts of this plant such as leaves and blossoms, transgenic propagation material such as protoplasts, calli, fruit, seeds, tubers, root stocks, germs, pollen, cuttings and transgenic progeny of the plant.

The plant cells according to the invention include differentiated and undifferentiated plant cells including protoplasts which were produced by the method according to the invention and which have integrated the expression cassettes of the present invention into the plant genome, or have received these as autonomously replicating molecules.

Of course, plant cells which contain the nucleic acid molecules according to the invention and plant cells (including protoplasts, calli, suspension cultures and suchlike) can further be cultivated.

All vectors were cloned into pBIN19-based binary vectors between the T-DNA left and right borders (LB and RB).

Bar-N, Bar-C, gene fragments from the *Bacillus amyloliquifaciens* barnase gene coding for the N- and C-terminal fragment of barnase, respectively (synthetic sequence with codon usage adapted for wheat; except in case of pICH13688 that carries a native sequence from *Bacillus amyloliquifaciens*); ALS-N, ALS-C, gene fragments coding for the N- and C-terminal fragment of a mutated version of *Oryza sativa* ALS or of *Arabidopsis thaliana* ALS (in case of pICH13688 only); IntN, IntC, gene fragments from the from the DnaE and DnaB genes of *Synechocystis* sp. coding for N- and C-terminal intein sequences (DnaB sequences fused to barnase are synthetic with codon usage adapted for wheat except in case of pICH13688); Pact, rice actin 1 promoter; Ptap, tapetum-specific promoter osg6B from rice; Tnos, nopaline synthase terminator; Tocs, octopine synthase terminator; CT, artificial chloroplast-targeting signal; Pubi, maize ubiquitin promoter, HptII, hygromycin phosphotransferase gene; Pspm, maize spm promoter; linker, nucleic acid sequence coding for a flexible $(GGGGS)_n$ linker cloned in frame to the barnase C-fragment.

Figure 2:
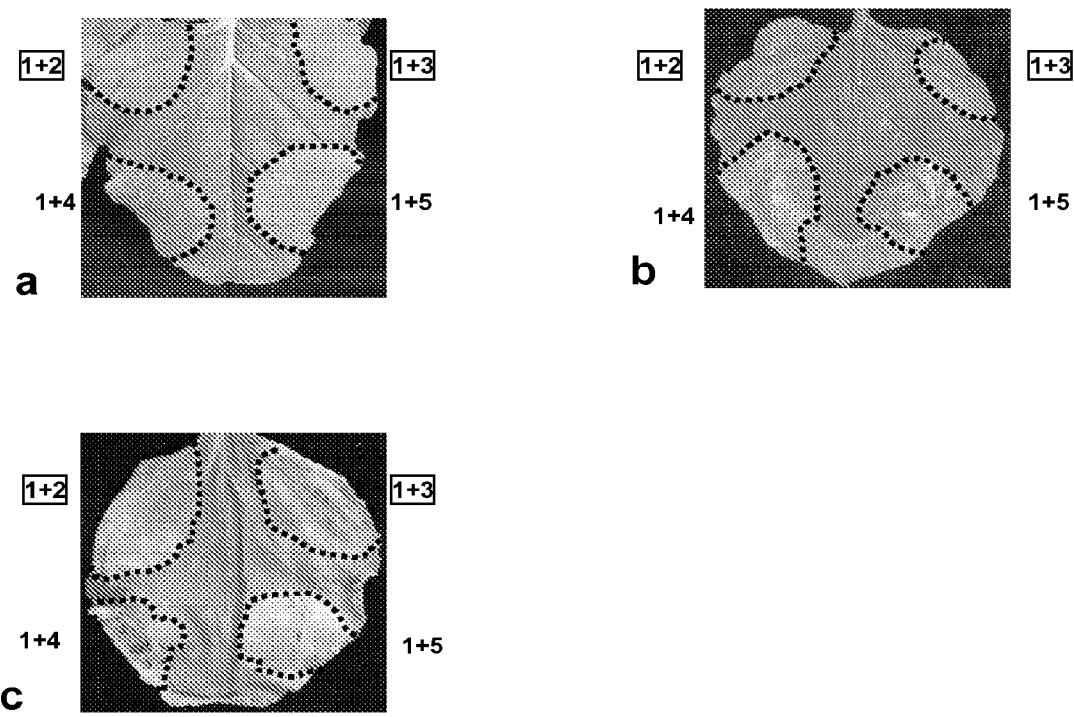
Figure 2:
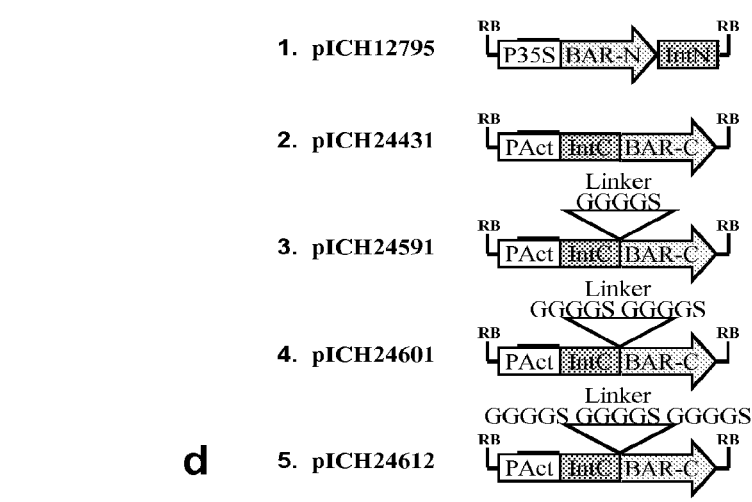

FIG. 2: Analysis of the Trans-Splicing Reaction Efficiency Using a Transient Assay in *Nicotiana benthamiana*

Two complementary barnase constructs (N- and C-terminal barnase fragments fused to the N- and C-terminal fragments of the DnaB intein, respectively) were infiltrated into leafs of *N. benthamiana*. The N-terminal gene fragments are expressed from a 35S promoter (pICH12795) whereas the C-terminal gene fragments are expressed from the weaker *Arabidopsis thaliana* Act2 promoter. The cytotoxicity increases with the size of the flexible GGGGS linkers introduced between the nucleic acid sequences coding for the C-terminal fragment of the DnaB intein and the C-terminal fragment of barnase (a-c). The structure of the infiltrated constructs is depicted in d. Construct pICH12795 was supplied by Icon Genetics.

Figure 3:
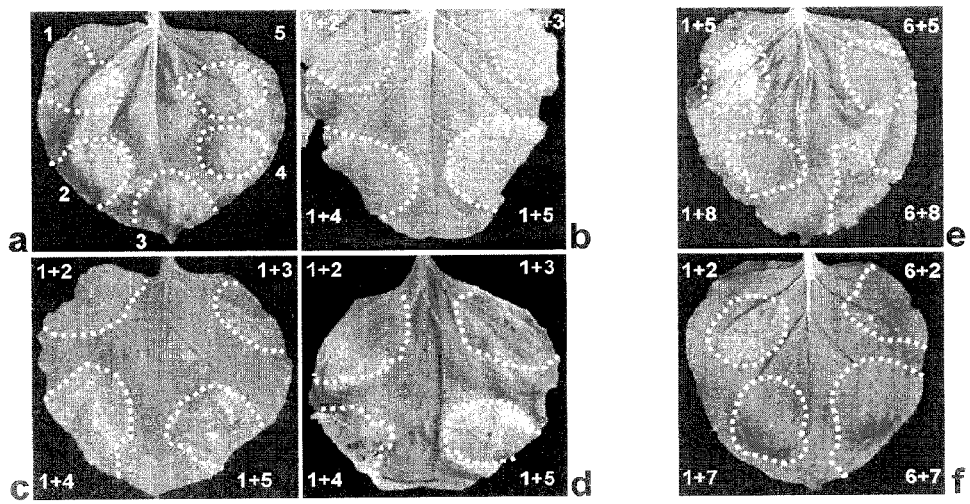
Figure 3:
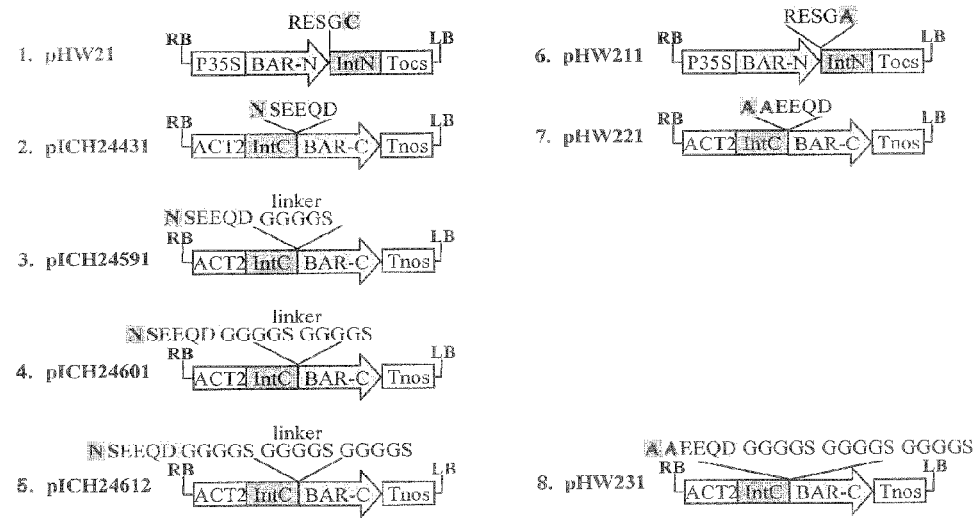

FIG. 3: Analysis of the Trans-Splicing Reaction Efficiency Using a Transient Assay in *Nicotiana benthamiana*

Mixtures of agrobacteria carrying different plasmids were infiltrated into leaves of 7-8 weeks old *N. benthamiana* plants. At the infiltration point, the epidermis was carefully scratched in order to facilitate efficient delivery of the *agrobacterium* solution into the plant tissue. After infiltration, the plants were grown under greenhouse conditions.

a-d, effects of linker-insertions between the domains of the mature protein. e, f, effects of mutating key trans-splicing residues. The leaf morphology is depicted 4 (b), 10 (c) or 12 (a, d, e, f) days after infiltration. g, The structure of the infiltrated constructs is shown in g. ACT2, *Arabidopsis* actin 2 promoter; 35S, Cauliflower Mosaik Virus 35S promoter.

Figure 4:
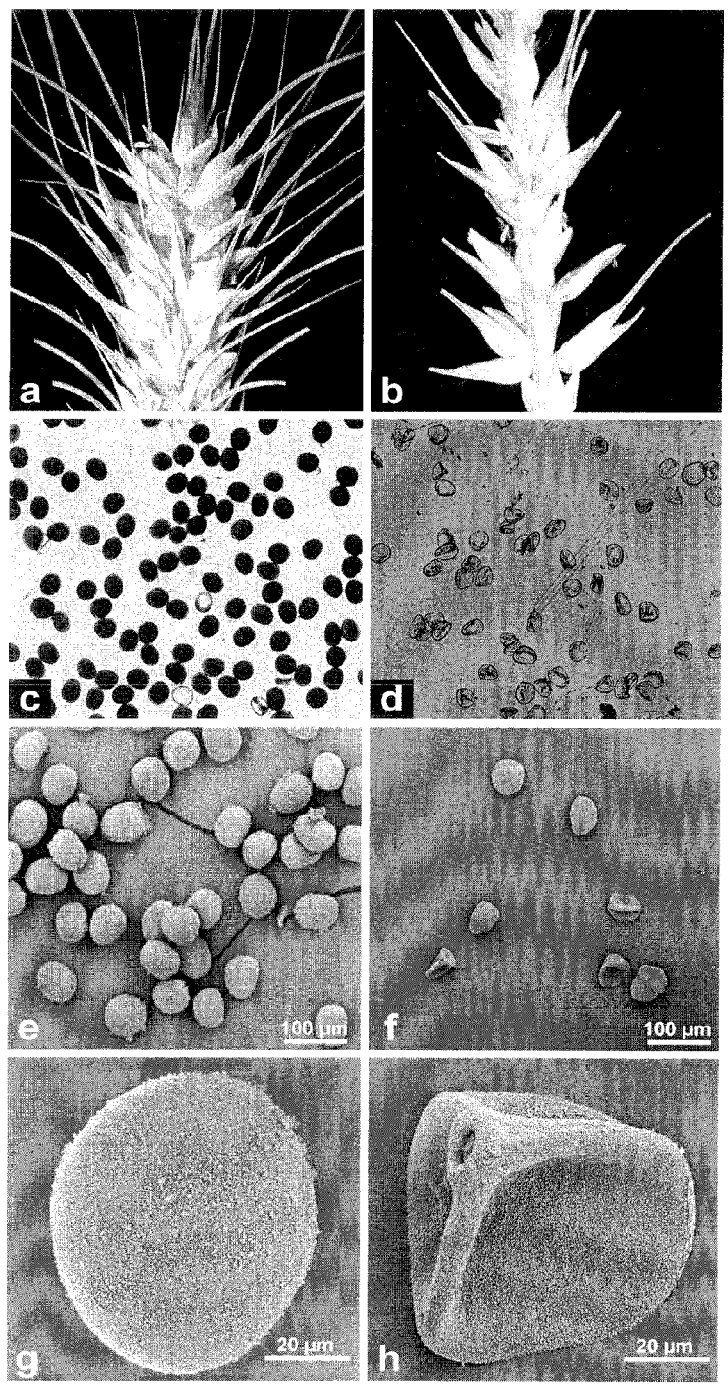

FIG. 4: Phenotype of Male-Sterile Wheat Plants

Morphology of wheat spikes from a male fertile control plant (that was generated by in vitro culture methods, e.g. that grew up under identical conditions like transgenic plants) and a transgenic male sterile plant containing T-DNA pICH27371 are shown in a and b, respectively. The spike of the transgenic plant displays the typical "open floret" phenotype and contains no seed. The deformed pollen produced by plants carrying a functional barnase protein can be clearly distinguished from the pollen of wildtype plants in the Alexander's vitality tests (c, d) and in SEM analysis (e-h). The left-hand column shows the phenotype of the control plant and the right-hand column shows the phenotype of the male sterile plants.

Figure 5:
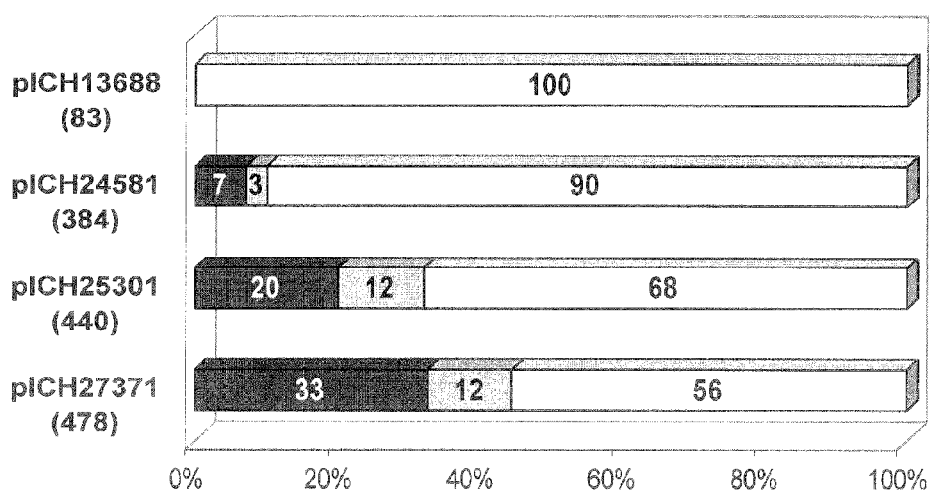

FIG. 5: Efficiency of Differently Modified Split-Barnase-Systems in Primary Transformants ($T_0$)

The proportion of $T_0$ plants displaying complete sterility (black sections of the bars) is compared to the proportion of plants carrying both sterile and fertile flowers (gray) and such plants that are completely fertile (white) for all plasmids investigated. Total number of $T_0$ individuals investigated is given in parentheses.

Figure 6:
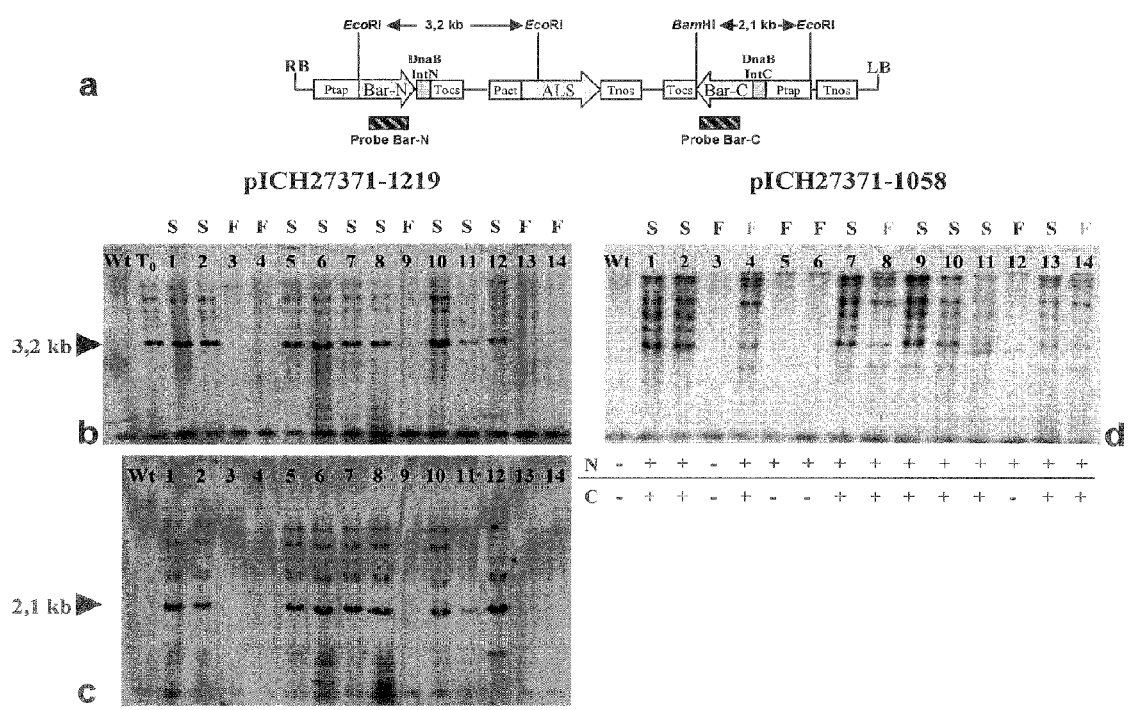

FIG. 6: Molecular Characterization of Wheat Lines Transgenic for pICH27371

Progeny from $T_0$ plants pICH27371-1219 (b, c) and pICH27371-1058 (d) segregates into male-sterile (S) and fertile (F) individuals. Total DNA from plants pICH27371-1219 and pICH27371-1058 was digested with EcoRI and BamHI, respectively, and a Southern Blot analysis was performed. The EcoRI digested DNA was hybridized with a probe homologous to the barnase-N (b, d) and the BamHI digested DNA was habridized with the barnase-C sequence (c), respectively. Regions of homology are shown by rectangles in the schematic illustration (a). For pICH27371-1058, the presence of the N- or C-terminal barnase gene fragment as proven by PCR is indicated. Wt, wildtype control plant; $T_0$, primary transformed plant.

Figure 7:
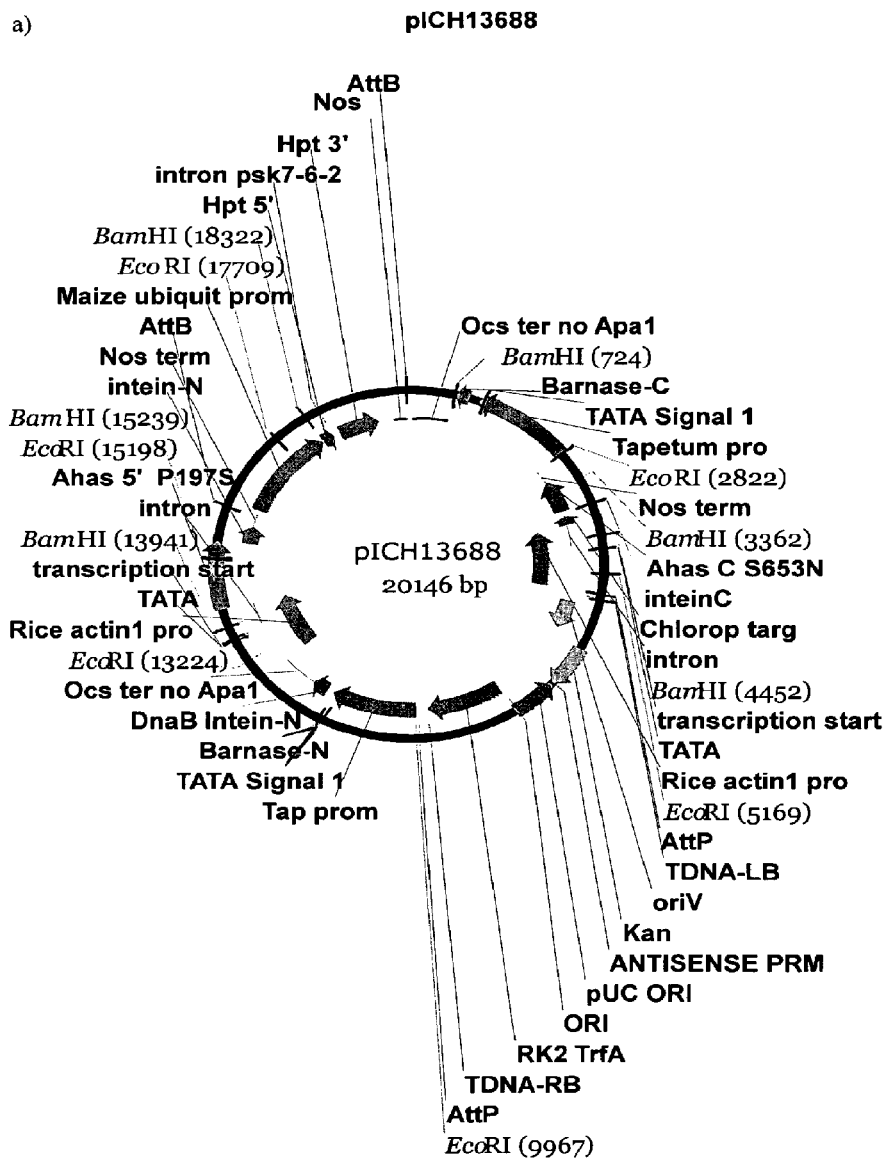
Figure 7:
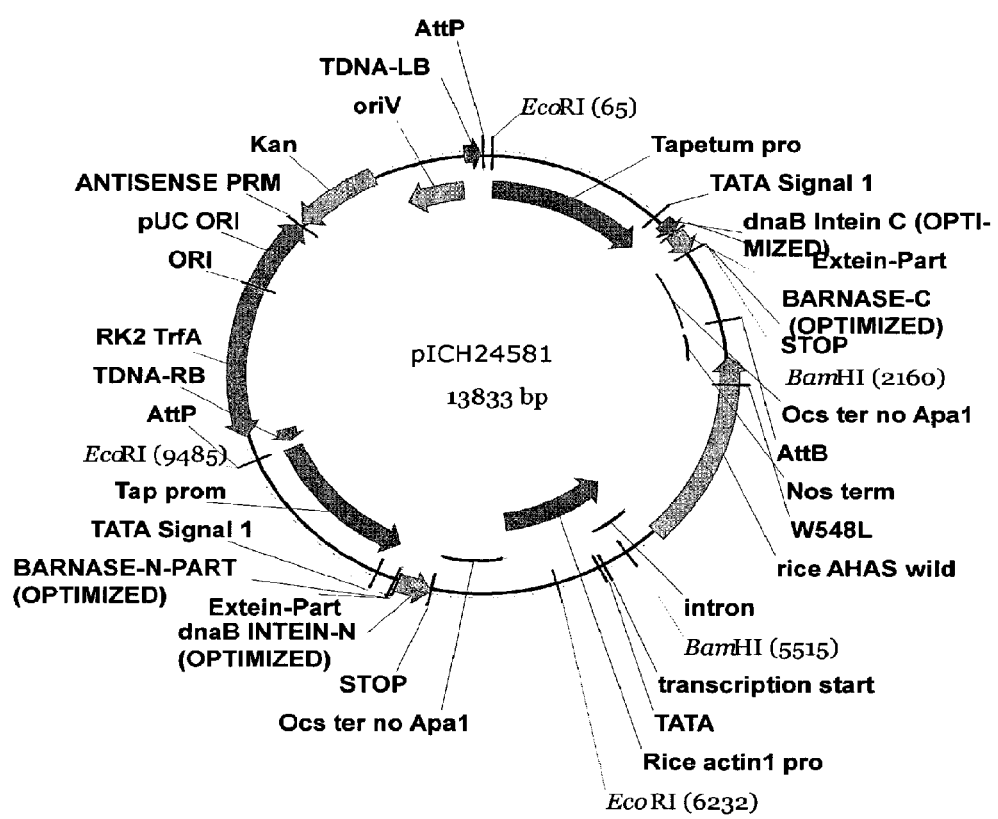
Figure 7:
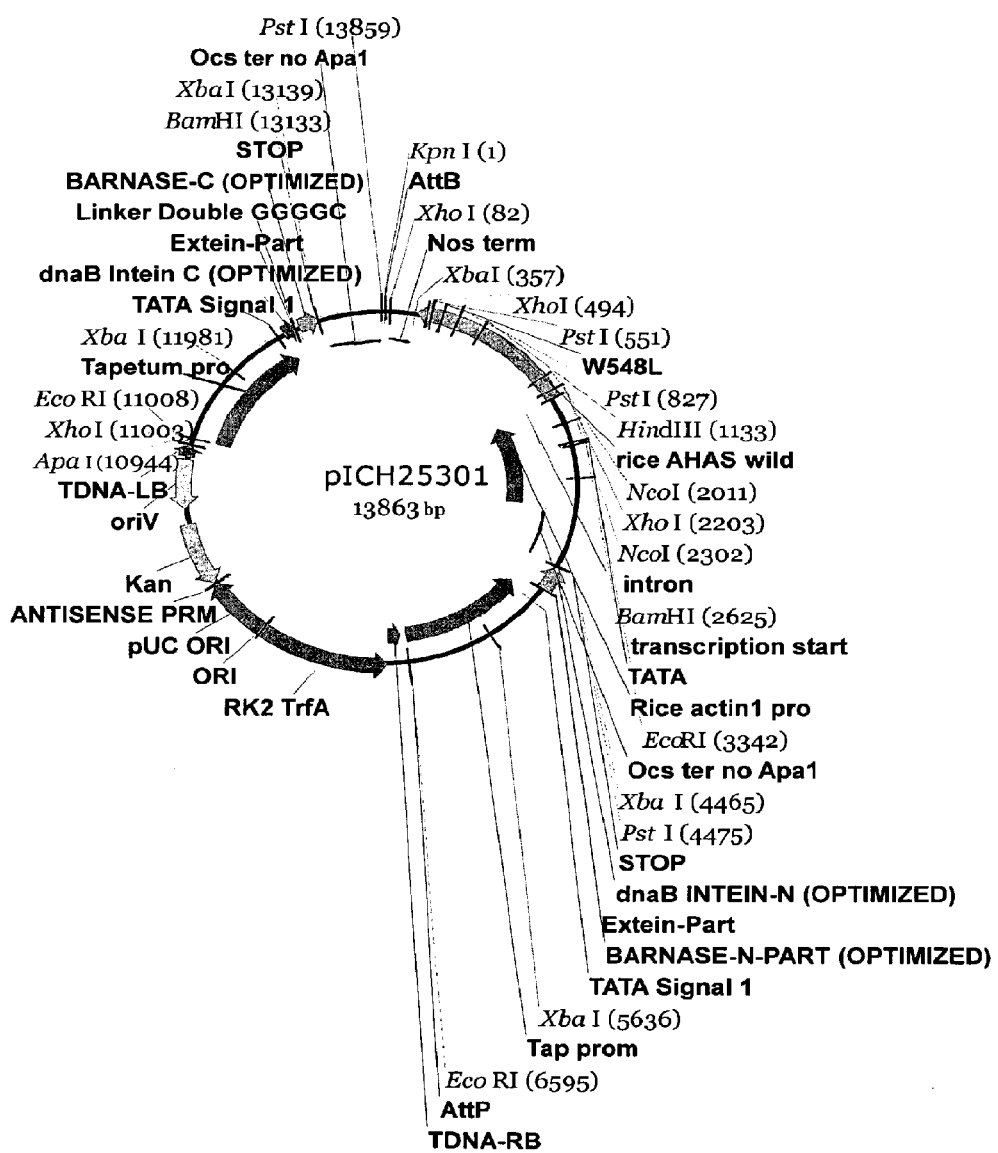
Figure 7:
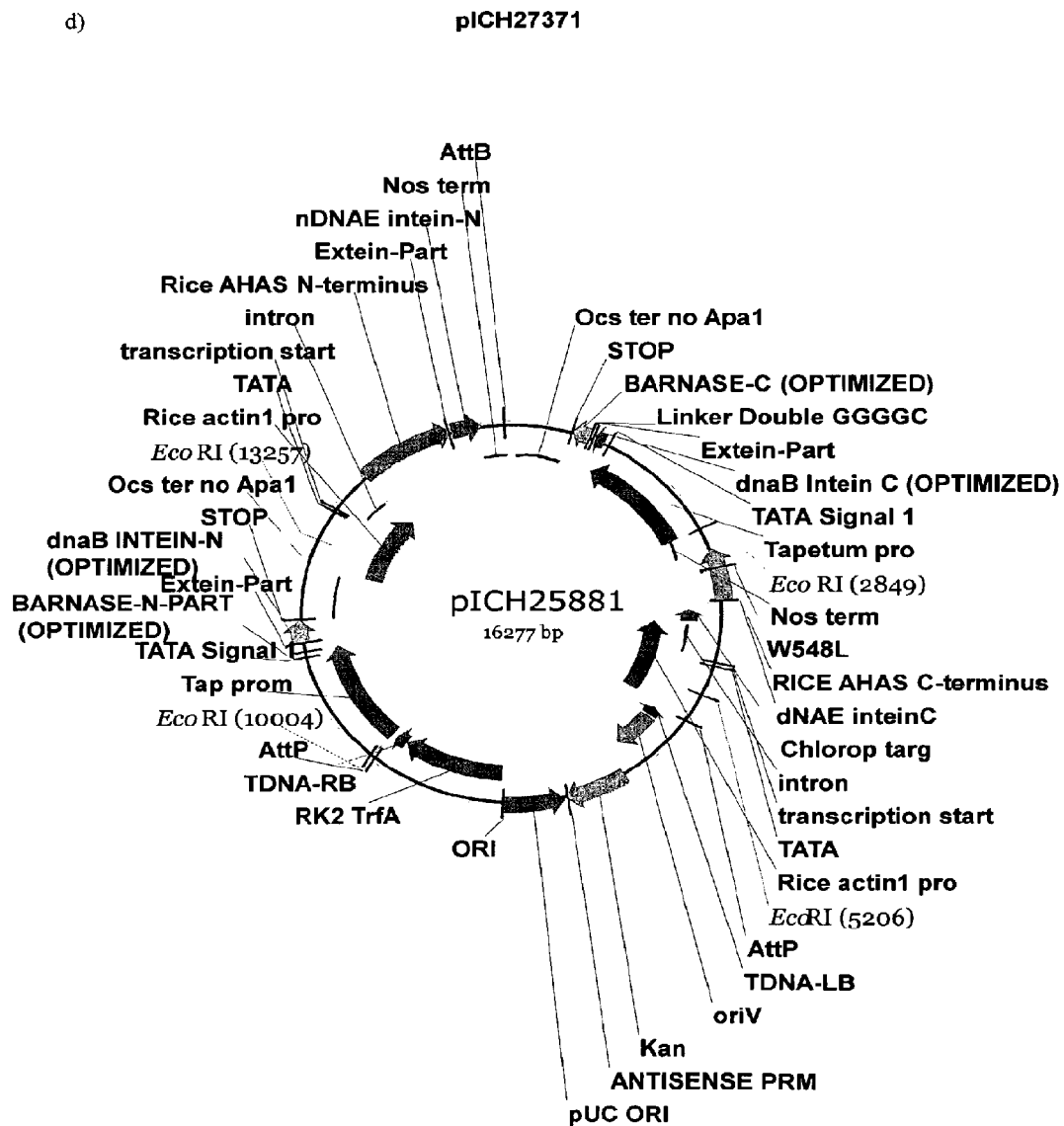
Figure 7:
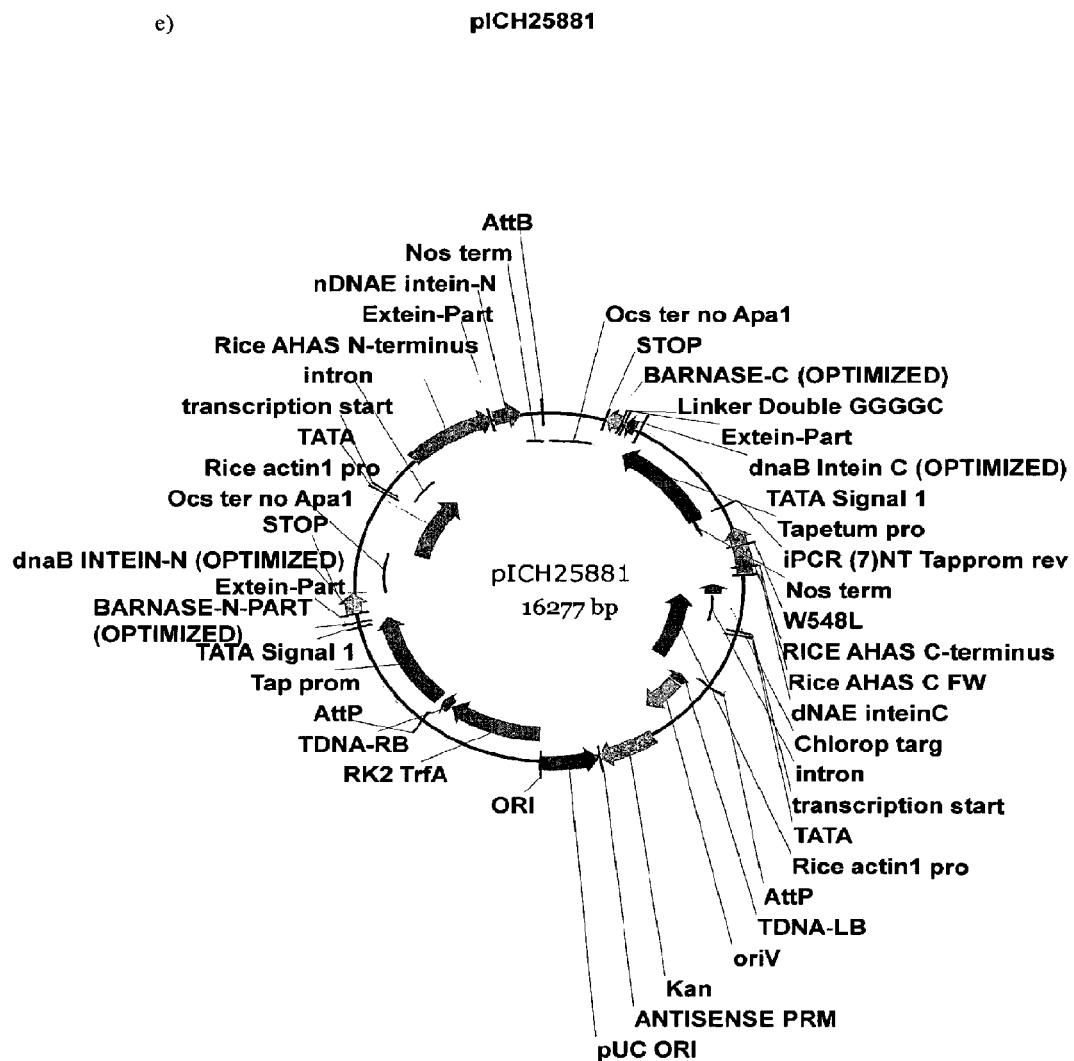

FIG. 7: Maps of the Plasmids Used for Transformation
a) pICH13688
b) pICH24581
c) pICH25301
d) pICH27371
e) pICH25881

Figure 8:
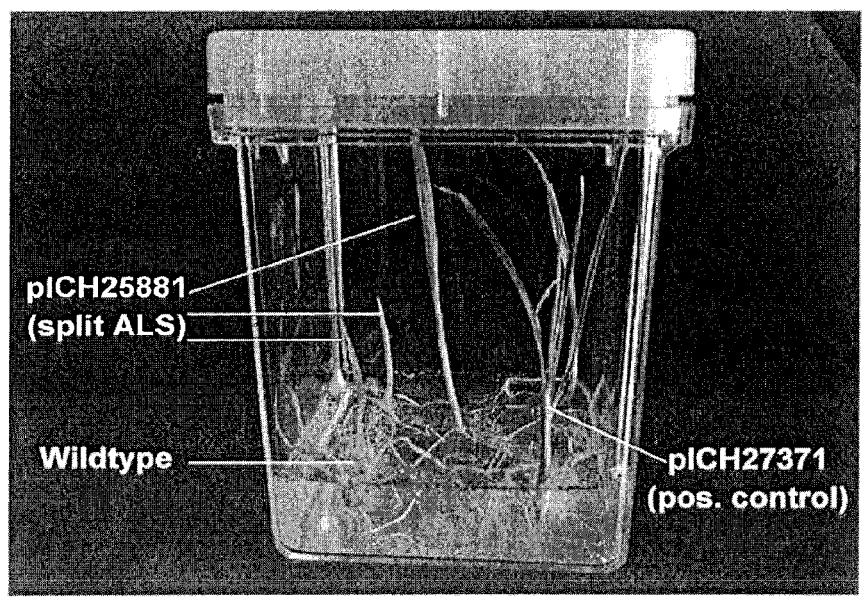

FIG. 8: Selection of Plants Carrying pICH25881 (Split ALS).

The picture depicts a $T_2$ plant that is selected after two preceding selections of the $T_1$ and the $T_0$ ancestors (proving that the phenotype is stably inherited over three generations). Plants carrying the plasmid pICH27371 with the non-split ALS gene were used as a positive control for the selection. Selection conditions are described in the examples.

Figure 9:
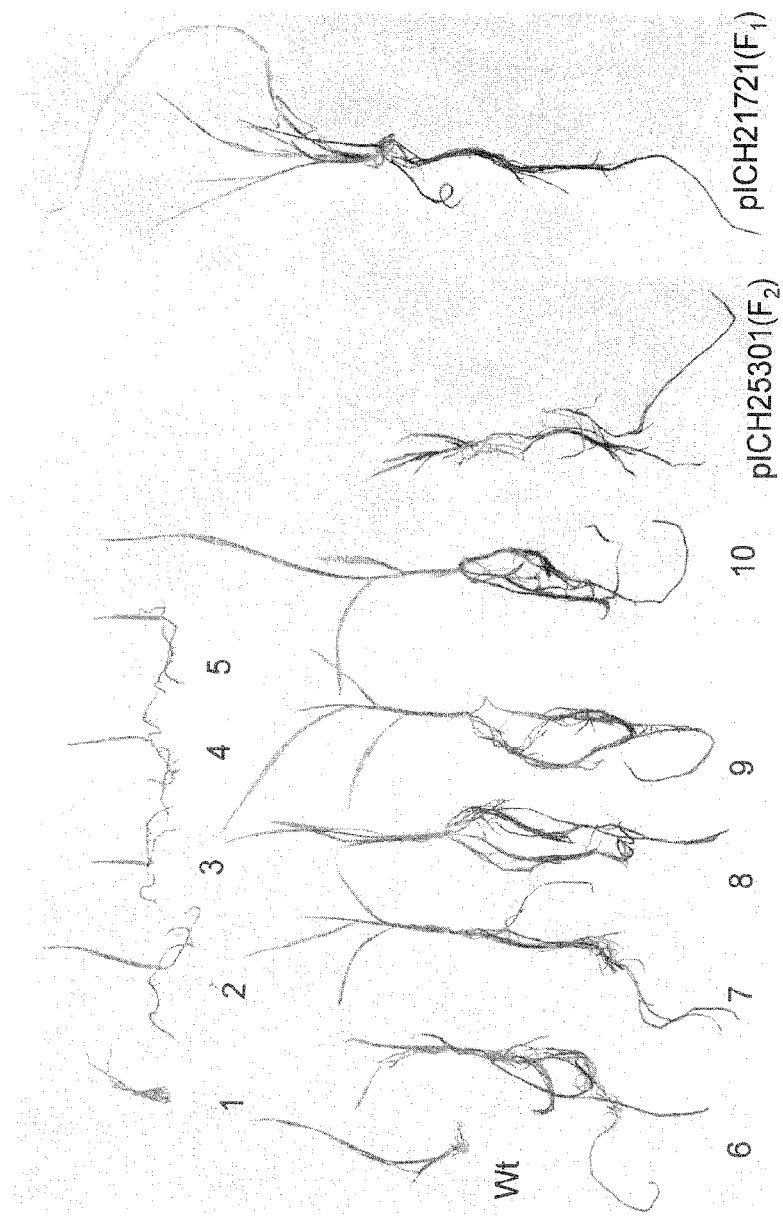

FIG. 9: Split ALS from Rice Confers Herbicide Resistance in Wheat $F_2$ plants of a line carrying pICH25881 (split ALS) derived from selection on medium containing 0.5 μM PSM. Plants were grown in phytochambers under a regime of 16 h light, 24° C. and 8 h dark, 16° C. Herbicide resistant plants displayed normal root development (6-10). $F_2$ plants that lost the T-DNA due to segregation have stunted roots and did not survive on herbicide containing medium (1-5). pICH25301 ($F_2$), pICH21721 ($F_1$), control plants carrying a continuous ALS transgene. Plants are shown 21 days after transferring plantlets on the selective medium. Wt, wildtype control plant.

Figure 10:
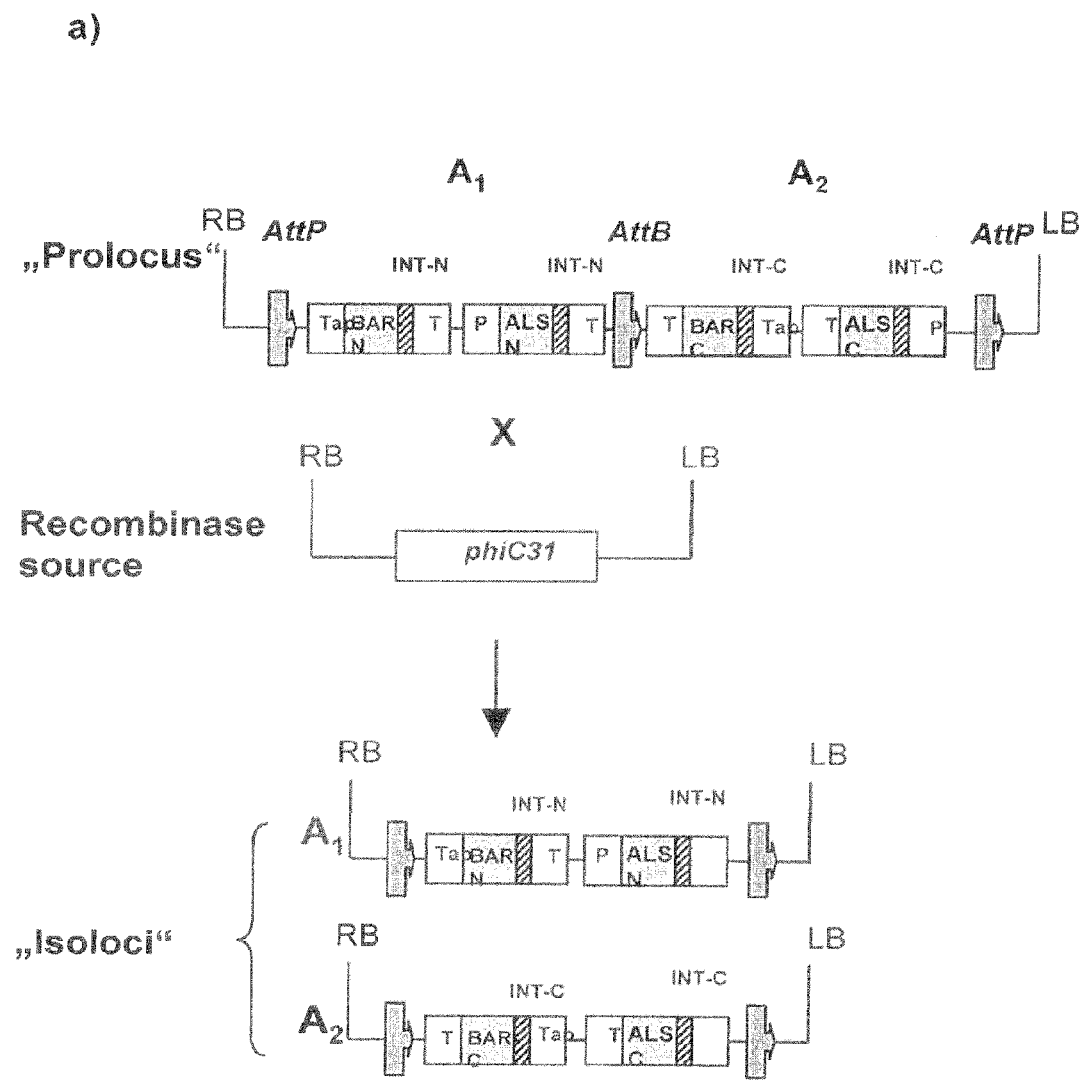
Figure 10:
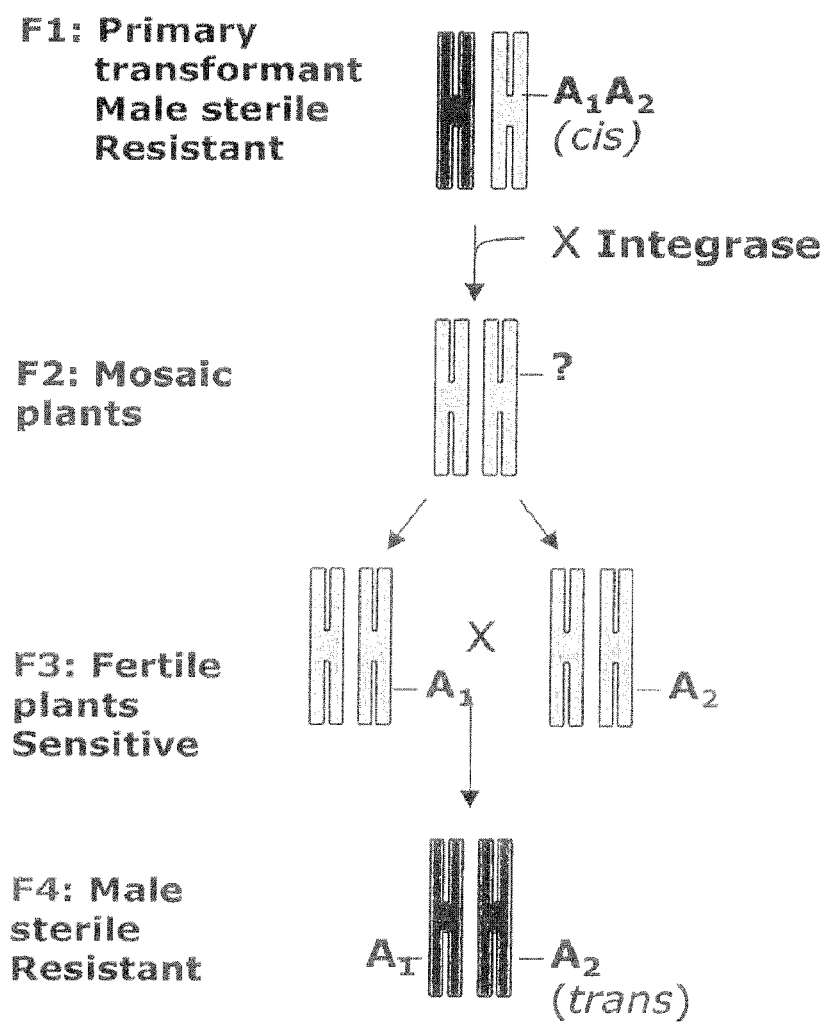
Figure 10:
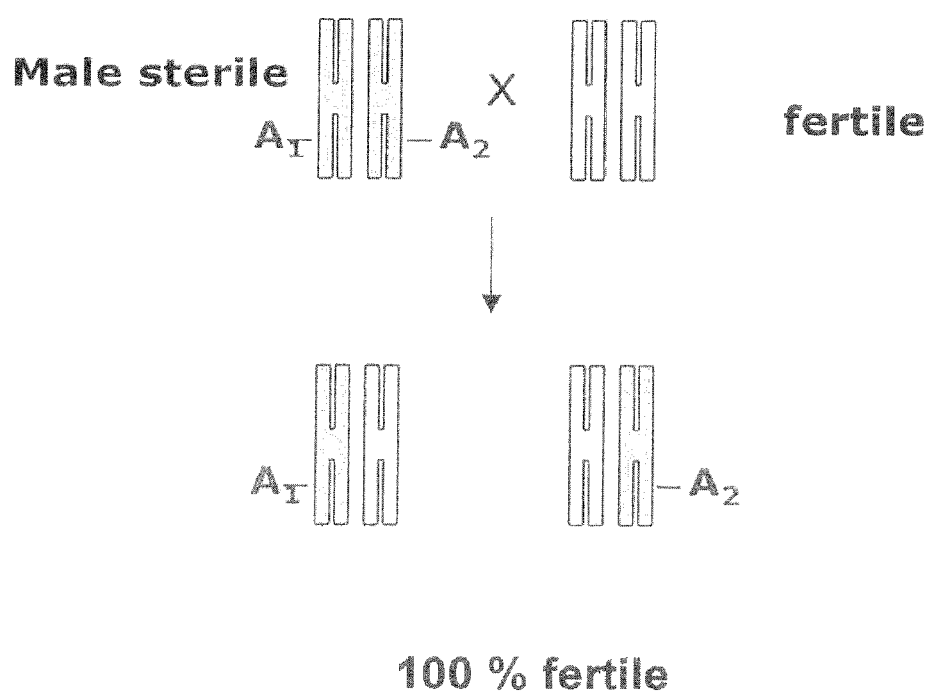
Figure 10:
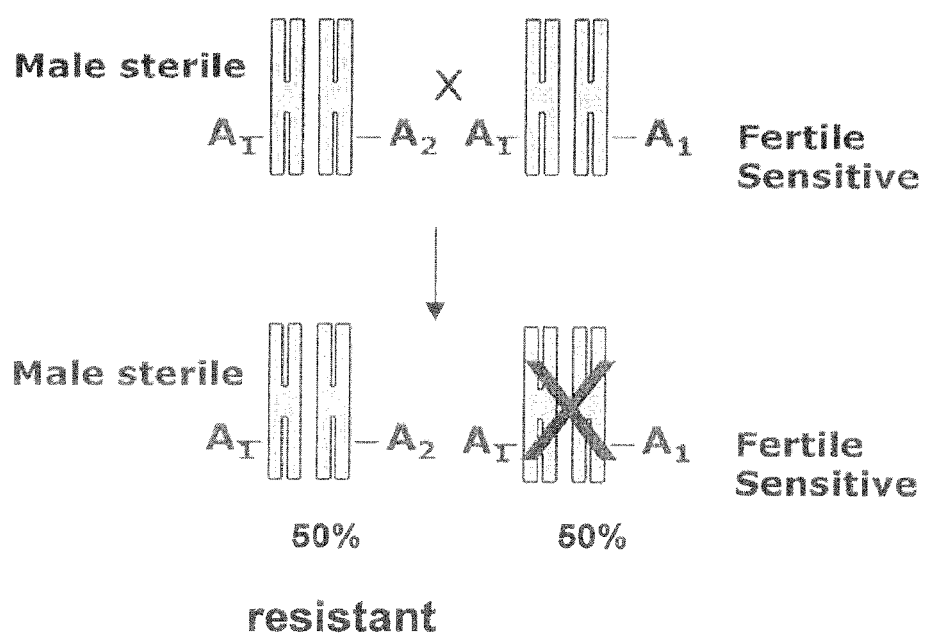

FIG. 10: Strategy for the Maintenance of the Male Sterility and for the Production of Hybrid Seed a) An expression construct containing the first, second, third and fourth expression cassettes of the present invention (corresponding to plasmid pICH25881) is transformed into plant cells to form a prolocus. Upon crossing with a plant expressing recombinase, a derivatization of the prolocus can occur in the progeny plant, thus forming two isoloci (A1, A2) on identical loci on homologous chromosomes in different progeny plants.

b) Production of F3 plants containing either the N-terminal part (A1) or the C-terminal part (A2) of barnase using a site-specific recombinase (integrase) and producing male sterile F4 plants using the F3 plants c) Use of the male sterile plants to produce fertile hybrid seed by crossing with a male fertile parent d) Maintenance of the male sterile line by crossing it with a fertile plant containing only the N-terminal part of barnase (A1)

Figure 11:
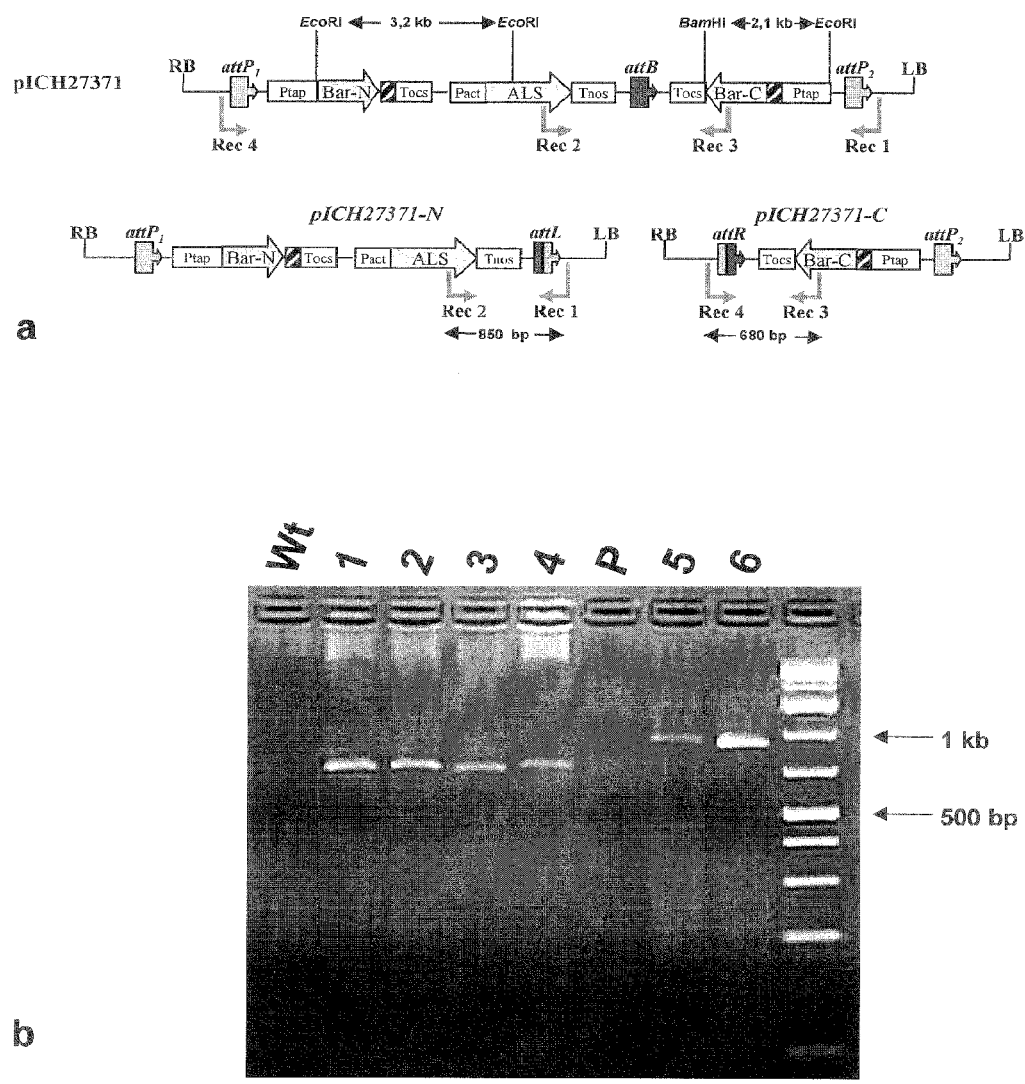

FIG. 11: Molecular Proof of the PhiC31-Induced Recombination Process a) Schematic illustration of the positions of primer binding sites (symbolized by arrows) before (pICH27371) and after recombination (pICH-27371-N, pICH27371-C).

b) PCRs were carried out on pICH27371 plasmid-DNA (P) and on total DNA from plants carrying pICH27371 that have been crossed with pICH13130. Recombination of the N-terminus (i.e. between $attP_1$ and attB) was detected with Primer Rec 1, Rec 2 in plants 5 and 6; recombination of the C-terminus (i.e. between $attP_2$ and attB) was detected with Primer Rec 3, Rec 4 in plants 1-4.

Figure 12:
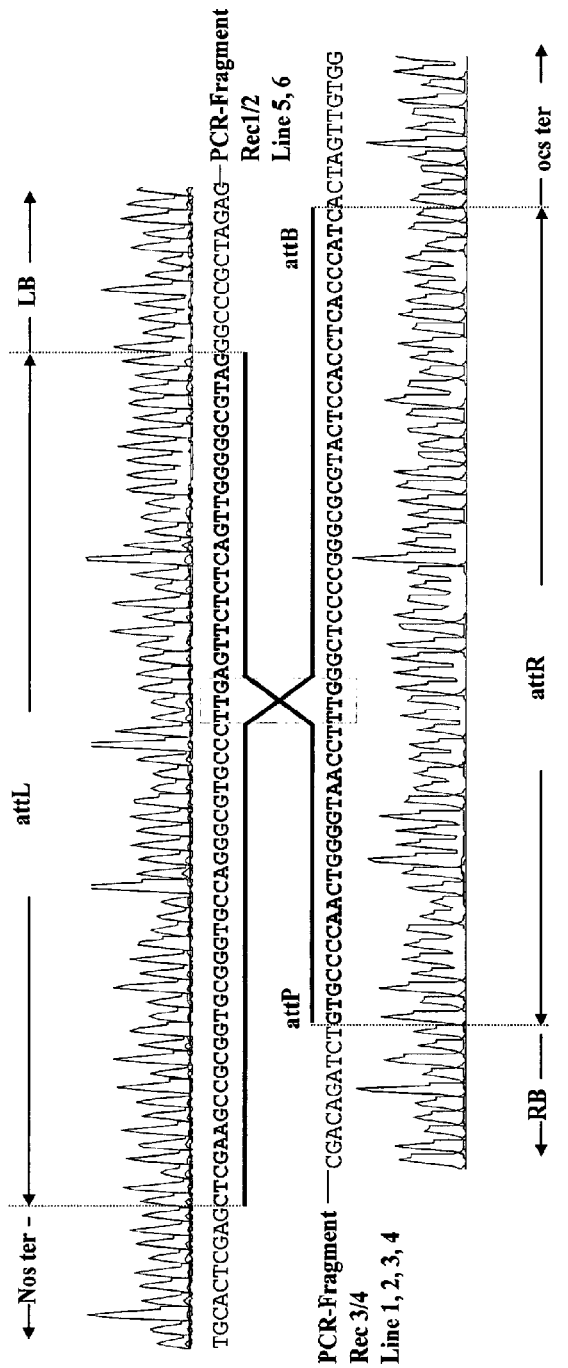

FIG. 12: Sequence Analysis of PCR Products

In total, 25 PCR-Products resulting from the PCR Rec 1-Rec 2 and 25 PCR products resulting from the PCR Rec 3-Rec 4 were analyzed. Without exception, all sequences represented the expected recombination product containing the sequences attL or attR, respectively. The diagram includes two original abi sequencing files (sequencing reaction performed by the IPK-Gatersleben PGRC Sequencing Service).

EXAMPLES

1) Plant Material and Growth Conditions

Spring wheat (*Triticum aestivum* L., cultivar "Bobwhite") was used throughout this study. For standard breeding, plants were grown under greenhouse conditions with 16 h of light at 20° C. and 8 h of darkness at 16° C. For assaying the temperature sensitivity of male-sterile phenotypes, plants were grown in phytochambers at 35° C. for 16 h in light and at 20°

C. for 8 h in the dark. For DNA isolation, plant tissues were harvested, frozen in liquid nitrogen, and stored at −80° C.

2) Standard Molecular Biology Techniques

Standard molecular biology procedures were performed as described in Sambrook et al., 2001 (Molecular cloning: A laboratory manual, 3$^{rd}$ edition, Cold Spring Harbor Laboratory Press).

3) Construction of the Vector Plasmids

Figure 1:
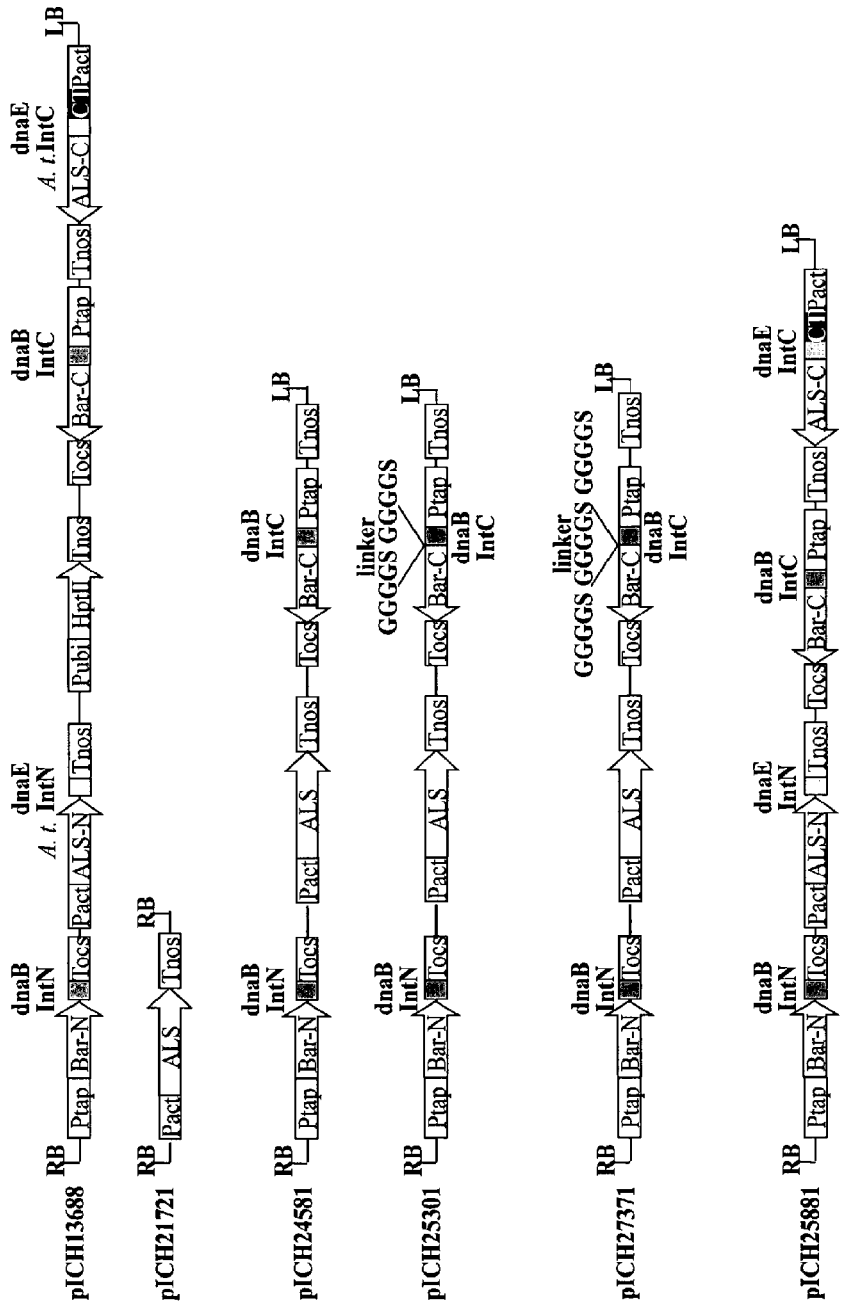
FIG. 1: Structure of the T-DNA Constructs

All vectors used in this study (FIG. 1) are pBIN19-based binary vectors and were constructed using standard recombinant DNA methods. The vectors are derivatives of plasmid pICH13688 (FIG. 1). The structure and construction of pICH13688 is described in Gils et al. (2008) Plant Biotechnol J. 6(3): 226-35. The T-DNA sequence of pICH13688 is deposited in the EMBL/GENBANK database under the accession number AM888351.

Barnase System

For inducing male sterility, the vectors contain split barnase genes which are fused to N- and C-terminal fragments of the Ssp DnaB intein. Protein splicing is depending on the chemical nature of the splice site junction amino acids. Hence, the insertion of stretches containing exon sequences is supposed to increase the efficiency of protein trans-splicing (Sun et al. (2001) Appl. Environ. Microbiol. 67: 1025-1029). The amino acid sequence SIEQD was inserted between DnaB IntC and Bar-C. Six of the seven amino acids belong to the adjacent extein sequence of the DnaB gene. Similar, the amino acid sequence RESG from the DnaB extein was introduced between DnaB IntN and Bar-N. Additionally, a methionine starting codon was added at the 5' terminus of the DnaB IntC sequence.

Both barnase-intein fusions were transcribed from a tapetum-specific rice promoter (Tsuchiya et al. (1995) Plant Cell Physiol. 36: 487-494).

ALS-System Plasmid pICH21721 contains a rice ALS gene (Gene Bank accession number AP008208, *Oryza sativa*; japonica cultivar-group; genomic DNA, chromosome 2, position 18335903-18337834). At position 548, the mutation Trp>Leu was introduced according to Tan et al. (2005) Pest Manage. Sci. 61: 246-257. The ALS gene is expressed under control of the constitutive rice Actin 1 promoter (McElroy et al. (1990) Plant Cell 2: 163-171) and the nopaline synthase (nos) terminator (Jones et al. (1992) Transgenic Res. 1: 285-297). pICH21721 serves as a control vector for transformation.

Vector pICH25881 contains two fragments of the rice ALS gene that are expressed individually from a rice actin promoter. ALS-N (see FIG. 1) contains 403 amino acids of the N-terminal end of the mature ALS protein (GenBank accession no AP008208, position 18335903-18337111) whereas ALS-C contains the residues 404-644 (GenBank accession no AP008208, position 18337112-18337834). For linking both parts of the ALS by trans-splicing, Ssp DnaE intein fragments were cloned in frame to the ALS segments, including extein sequence stretches, as described in (Gils et al. (2008) Plant Biotechnol J. 6(3):226-35). For targeting the C-terminal ALS-intein fusion protein to the chloroplast, an artificial chloroplast targeting sequence (MASSMLSSAAV-VATRASAAQASMVAPFTGLKSAASF-PVTRKQNNLDITSIA SNGGRVQCA) was fused to the segment. Like the complete ALS gene in pICH27371, the expression of both ALS protein segments are controlled by a rice Actin 1 promoter and terminated by nos terminators.

In case of vectors pICH24581, pICH25301 and pICH27371, the barnase-intein fusions are encoded by synthetic sequences in which the codon usage was adapted to the codon bias of *Triticum aestivum* genes (chemically synthesized by GENART, Regensburg, Germany). Additionally, amino acids that have been inserted into the original vector as a result of cloning strategies and are not present in the native barnase sequence (D and V between Bar-N and DnaB IntN in case of plasmid pICH13688) were removed. Furthermore, vectors pICH25301 and pICH27371 contain flexible linker sequences that are introduced in frame between the dnaB InteinC and the Barnase-C fragment. The linkers should not exhibit a propensity for ordered secondary structure or any tendency to interfere with domain folding. Thus, the sequence Gly-Gly-Gly-Gly-Ser was selected to bridge the 5'- and 3' barnase fragments either in a double [(Gly-Gly-Gly-Gly-Ser$_2$); pICH25301] or triple [(Gly-Gly-Gly-Gly-Ser)$_3$; pICH27371] configuration). In order to avoid repetitiveness of the sequences, a different codon usage was used for each of the GGGGS units.

Vectors for Transient Barnase Expression Assays

Vector pHW21 (N-terminal vector for transient assays) contains a fusion of Bar-N and DnaB IntN, as described for the vectors pICH24581, pICH25301, pICH27371 and pICH25881 (FIG. 1). The expression of the barnase-intein fusion was controlled by the cauliflower mosaic virus 35S promoter and an octopine synthase terminator. Using PCR site-directed mutagenesis, the N-terminal amino acid of DnaB Int (C1) was changed from cysteine in pHW21 to alanine, resulting in vector pHW211. The C-terminal vectors for transient assays contain a fusion of DnaB IntC and Bar-C. The intein-barnase fusion sequence is cloned between an *Arabidopsis* actin 2 promoter and a nopaline synthase terminator. In pICH24591, pICH24601, pICH24612 and pHW231, flexible linkers composed of one to three GGGGS stretches were cloned in frame between the extein stretch SEEQD and Bar-C. By PCR site-directed mutagenesis, the C-terminal amino acid of DnaB Int (Asn154) and the following residue of the C-terminal extein stretch (Ser+1) were both changed to alanine in the case of pICH24431 (resulting in pHW221, FIG. 3g) and pICH24612 (resulting in pHW231, FIG. 3g).

4) Genetic Transformation of Wheat Plants Via Biolistic Particle Bombardment Callus Culture Maintenance Immature seeds of wheat were surface-sterilized by immersing them in 70% ethanol for 3 min. The procedure was followed by incubation in 2.5% sodium hypochlorite solution, including 0.01% SDS, with shaking at 125 rpm for 7 min and subsequently by three washing steps in sterile distilled water. Immature embryos (1.0-2.5 mm in length, semitransparent) were excised aseptically and placed, with scutellum-side up, on MS culture medium (Duchefa, MO222; (Murashige and Skoog (1962) Physiol Plant 15(3): 473-497), containing 30 g/l sucrose, 2 mg/l 2,4-D (2,4-dichlorophenoxyacetic acid) and 0.25% phytagel for solidification. Embryos that develop compact nodular calli were selected using a stereomicroscope and used for bombardment 14-21 days after isolation. The cultures were kept in the dark at 25° C.

Microprojectile Bombardment of Immature Embryos

The gold coating procedure was done according to Sanford et al. (1993) Methods Enzymol. 217: 483-503 and following the original protocol of Bio-Rad (Munich, Germany).

Standard Procedure

For particle coating, 50 µl of gold suspension (0.6 Micron gold in 50% glycerol, 60 mg/ml) was mixed with 10 µl (1 µg/µl) plasmid-DNA, 50 µl 2.5 M $CaCl_2$ and 20 µl 0.1 M spermidine. The mixture was shaken for 2 min, followed by incubation at room temperature for 30 min, brief centrifugation and washing with 70% and 99.5% ethanol. Finally, the gold particle pellet was suspended in 60 µl of 99.5% ethanol. For one bombardment procedure, 6 µl of the suspension was used. All manipulations were done at room temperature.

Microprojectile bombardment was performed utilizing the Biolistic PDS-1000/He Particle Delivery System (Bio-Rad, Munich, Germany). Prior to the bombardment, the immature embryos were pre-treated for four hours on MS medium supplemented with 100 g/l sucrose.

Approximately 50 Embryos were placed in the centre of a plate to form a circle with a diameter of about 10 mm. The shooting was carried out using a helium pressure of 900 psi, with 15 mm distance from a macrocarrier launch point to the stopping screen and 60 mm distance from the stopping screen to the target tissue. The distance between rupture disk and launch point of the macrocarrier was 12 mm. Finally, 16 hours after treatment, the calli were transferred to MS medium containing 60 g/l sucrose and grown in dark conditions for one week at 25° C.

Selection and Regeneration

For obtaining plants transgenic for all vectors except pICH13688, callus selection was carried out in vitro on medium containing primisulphuronmethyl (PSM) and imazethapyr (IMA), both belonging to the class of pyrimidinylsulphonylurea herbicide. Concentrations: 0.5 µM PSM+ 1.0 µM IMA (first selection); 1.0 µM PSM+1.0 µM IMA (second selection), 0.5 µM PSM+1.5 µM IMA (subsequent selections) Selection of plants carrying pICH13688 was carried out by callus selection on medium containing 150 mg/l hygromycin B.

The cultures were kept in the dark at 22° C. After 5-6 successive callus selection steps (total time: 4-6 months) callus tissue was subcultured in MS regeneration medium supplemented with 1 mg/l kinetin, 7 mg/l zeatin. Regenerating plantlets were transferred to jars with half strength hormone-free MS medium containing 0.5 µM PSM+1.0 µM IMA or 50 mg/l hygromycin B respectively. Fully developed plantlets were acclimated for 7-10 days at room temperature in liquid medium containing four-fold diluted MS salts. Plants with developed roots were transferred into soil and grown under greenhouse conditions to maturity.

For assaying the herbicide resistance of progeny plants, embryos were isolated from seeds and selected in vitro.

Selection of Transgenic Wheat Plants by a Split ALS Gene System

By callus selection on PSM and IMA, lines carrying the vector pICH25881 displayed an herbicide tolerant phenotype that was indistinguishable from the phenotype of control plants (FIG. 9). The herbicide resistance was stably inherited over three generations ($T_0$-$F_2$) and the plants displayed normal vegetative development. From these results it can be deduced that, despite the low overall efficiency, a functional ALS protein can be produced by the assembly of two precursor proteins and that the chosen barnase-intein junction site is principally suitable for the split ALS system.

5) Analysis of Wheat Transformants Carrying T-DNA pICH13688

In case of *A. thaliana*, transformation of pICH13688 led to a high frequency of male-sterile plants among primary transformants. Therefore, initial wheat transformation experiments were carried out using this vector. To be able to test the system in wheat, and since it was uncertain whether ALS selection would work in this species (given that the ALS of pICH13688 is derived from an *Arabidopsis* gene), the plants were selected on hygromycine. After growing the primary transformants to maturity, the function of the split-barnase system was tested by pollen activity assays. All 83 plants carrying the vector pICH13688 displayed full fertile pollen that was non distinguishable from wildtype control plants (see FIG. 5) and produced seed. Therefore, it can be concluded that the split-barnase system of pICH13688 that is inducing pollen abortion in dicotyledonous species is not efficient in wheat.

6) Delivery of *Agrobacterium* into Plants for Transient Assays

Prior to transforming new vector constructs in wheat plants, the effect of $(GGGGS)_n$ linker sequences was tested by a rapid transient assay based on the agroinfiltration of *Nicotiana benthamiana* leaves.

T-DNA-vectors were transformed into *Agrobacterium* strain GV3101:pMP90. The infiltration of *Agrobacterium* into *N. benthamiana* plants was performed according to a protocol described in Marillonnet et al. (2004) Proc. Natl. Acad. Sci. USA 101: 6852-6857.

Flexible glycine/serine linker sequences of varying length [$(GGGGS)_1$; $(GGGGS)_2$; $(GGGGS)_3$] were introduced into control vectors in such a way that they connect the N- and C-terminal domains of the mature barnase-protein after ligation via trans-splicing (see FIGS. 2 and 3). Combinations of T-DNAs that carry the N- and C-terminal parts of the barnase gene (under the control of constitutively expressed promoters) were introduced into leaves of *N. benthamiana* by syringe infiltration using *Agrobacterium* (FIGS. 2 and 3). Delivered alone, N- or C-terminal vectors do not exhibit cytotoxicity (Gils et al. (2008) Plant Biotechnol J. 6(3):226-35). However, when vectors containing the N- and C-terminal fragments were delivered by mixing the *Agrobacterium* suspensions, lesions are obtained in the affected tissue. The extent of cytotoxicity correlates with the length of the flexible linkers that are introduced in the C-terminal vectors. Infiltration of pICH12795 in combination with pICH14601 (no linker), results in minor effects. When constructs containing linkers were delivered into the plant tissue, first lesions occurred 4-5 days after infiltration. Usually, the tissue was completely destroyed 14 days after infiltration, depending on the linker size.

Furthermore, by site-directed mutagenesis, it could be demonstrated that that a trans-splicing mechanism is responsible for an efficient protein assembly in the split DnaB intein-system. In order to determine whether protein splicing or IPC (intein mediated protein splicing via affinity domains) results in the reconstitution of barnase activity, key residues of the split DnaB Int system were exchanged without manipulating the affinity domain. For the majority of inteins, three conserved residues are essential for trans-splicing (serine, threonine or cysteine at the intein N-terminus; asparagine or glutamine at the intein C-terminus; serine, threonine or cysteine as the first extein residue following the C-terminal splice site; Perler, *Cell*, 92, 1-4, 2002). By using the *Synechocystis* sp. DnaE intein to complement inactive EPSPS precursor proteins in *E. coli*, Chen et al. (*Gene*, 263, 39-48., 2001) demonstrated that the exchange of the three key splicing residues to alanine blocks trans-splicing, but, nevertheless, association of N- and C-terminal splicing domains led to a robust phenotype. However, in the present transient assays, the delivery of vectors carrying DnaB Int mutants did not result in apparent symptoms (see FIGS. 2 e,f). Hence, it can be concluded that the system of the invention requires intein-mediated splicing.

7) Molecular Analysis of Transformants

Isolation of Total Plant DNA

For DNA isolation, 300 mg leaf material of young plants was shock-frozen. Homogenization was carried out using a TissueLyser© from Qiagen (Hilden, Germany). Total plant DNA was isolated following a modified protocol from Dellaporta et al. (1983) Plant. Mol. Biol, Pep. 1: 19-29.

Primers used a) for detection of the N-terminal barnase-Intein fusion were Barnase-N FW (GCATCGATATGGC-CCAAGTG); dnaB Intein-N REV (GAGCTGGAGGGAG-GAGGATTCG) b) for amplification of the C-terminal barnase-intein fusion gene sequence were Barnase-C REV (GATCTT GGTGAAGTCTGTAG); dnaB Intein-C FW (GGGACTCCATCGTGTCCATCC) c) for detection of the N-terminal ALS gene sequence were ALS-N FW (GTCAGC-GACGTGTTCGCCTAC) and ALS-N-REV (GTCCTCCA ATCAAGGACAAG) and d) of the C-terminal ALS gene sequence were RiceALS-C FW (GCAATATGCCATTCAG-GTGC) RiceALS-C REV (CACG GACTGCAG-GAATATTG). Finally, for amplification of an ALS-fragment that covers both N- and C-terminal parts of the ALS sequence, ALS-N-3 FW (GATTCTCTATGTCGGTGGTG) and ALS-N-5'REV (GCGACAGAATTGCTT GAGCAG) were used.

PCR analyses were performed in a thermocycler (DNA Engine™ PTC-0200, Bio-Rad, Munich, Germany). Amplification was carried out for 35 cycles (94° C. for 1 min; 55° C. for 1 min; 72° C. for 1-2 min).

8) Scanning Electron Microscopy (SEM)

Probes of *T. aestivum* were dehydrated in an ethanol series, followed by critical point drying in a Bal-Tec critical point dryer (Bal-Tec AG, Balzers, Switzerland). Dried specimens were attached onto carbon coated aluminium sample blocks and coated in an Edwards 5150B sputter coater (Edwards High Vacuum Inc., Crowlesy, West Sussex, UK). Probes were examined in a Hitachi 54100 SEM (Hisco Europe, Ratingen, Germany) at 5 kV acceleration voltage. Digital recordings were made and saved as tif-files.

9) Fertility Assays

To check for the viability of pollen, anthers of control wild-type and sterile plants were stained with Alexander stain (Alexander (1969) Stain Technol. 44: 117-122). The assays were transformed prior to 2-3 days before anthesis.

10) Cross Pollinations

Pollination of male-sterile plants was performed by tearing anthers of untransformed bobwhite plants with tweezers just before anthesis and placing one anther into the closed flower of the male-sterile crossing partner.

11) Expression of N- and C-Terminal Barnase Fragments from T-DNA pICH24581, 25301 and 27371 Confers Pollen Ablation in Wheat Plants From the results obtained with the transient tests it could be concluded that the cytotoxicity of the split-barnase system can be significantly increased by introducing flexible amino acid stretches. Therefore, T-DNA vectors containing codon optimized barnase-intein fusions and flexible linkers $(GGGGS)_2$ and $(GGGGS)_3$ (FIG. 1) were constructed and delivered into wheat plants by biolistic bombardment. 1385 primary transformants ($T_0$) were assayed for pollen fertility. Pollen of at least three spikes of each $T_0$-plant was stained in double test series according to (Alexander (1969) Stain Technol. 44: 117-122) (FIG. 4). In contrast to pICH13688, it was possible to generate male sterility by transforming pICH24581, pICH25301 or pICH27371. Thus, it could be demonstrated that the constructs are functional with regard to the intein-mediated complementation of the barnase peptide fragments.

Sterile pollen can be identified unambiguously by a transparent phenotype in vitality-staining assays (FIG. 4 *d*) and a degenerated phenotype as been detected in scanning electron microscopy analyses (FIG. 4 *f, h*). The amount of pollen produced by male sterile plants was not reduced compared to that of wildtype plants that were generated by in vitro culture. Expression of barnase does not influence the vegetative phenotype in regard to germination frequency, plant height, leaf size, flowering time and tillering. Typically, to allow cross-pollination, florets of male-sterile plants open as a consequence of inhibited self-fertilization (FIG. 4 *b*).

From these observations it is concluded that trans-splicing of the barnase fragments fosters an efficient ligation of the protein fragments with the concomitant correct folding of the mature protein, that the barnase protein is catalytically functional, and that the activity is limited exclusively to the tapetum.

Strikingly, the frequency of male sterile phenotypes varied among the classes of primary transformed plants, depending on the T-DNA that was introduced. Here, the results obtained from the transient assays (FIGS. 2 and 3) were confirmed (FIG. 5). The highest frequency (45%) of plants displaying complete or partial male sterility is achieved by transforming pICH27371 which contains codon-optimized barnase-intein fusions and a triple GGGGS linker, followed by pICH25301 (double linker GGGGS); optimized barnase-intein fusion sequence: 32%] and pICH24581 (no linker, optimized barnase-intein fusion sequence: 10%).

For exploiting the stability of the phenotype under extreme environmental conditions, plants carrying pICH24581, pICH25301 and pICH27371 were grown in phytochambers from germination to maturity at 35° C. (16 h) and 20° C. (8 h, see material and methods). Although some of the plants displayed stress symptoms like reduced tillering and early senescence, all individuals carrying Bar-N and Bar-C were male-sterile whereas, in contrary, the control plants formed vital pollen and seed.

12) Inheritance of the Male-Sterile Phenotype: Analysis of $T_1$ Generation

The male-sterile plants were backcrossed with wildtype plants. Except a negligible number of cases (<2%), all backcrosses led to vital seed, showing that the sterility was restricted to the male gametes and did not affect reproducibility of the plants in general.

In 69 lines (76% of the cases), the pollen sterile phenotype was inherited to the $T_1$ generation. This demonstrates that pollen ablation caused by tissue culture effects (somaclonal variation) is a rare event and does not affect the overall statistic to a significant extent. None of the T₁ plants displaying male sterility lacked the barnase transgene fragments. In the majorities of T₁ progeny populations, the male-sterile phenotype can be strictly correlated with the presence of both transgene fragments. Segregation of the transgenes leads to reversion of fertility in all cases. Interestingly, some of the plants carry only an N-terminal or a C-terminal fragment of the barnase gene. Such T-DNA-truncation results from a fragmentation of the plasmids caused by physical forces during biolistic delivery. As expected, such individuals form vital pollen.

An example for the proof of a linkage between the male-sterile phenotype and the barnase gene fragments is given for two T₁ populations in FIG. 5. However, a number of lines produced also F₁ plants that were fertile although they inherited both barnase-fragments (as been shown by PCR). Southern blot analysis of the F₁ revealed that the barnase locus of fertile plants differed from that of the male-sterile plants (FIG. 6 *d*; line pICH27371-1058, plants 4, 8, 14). This indicates the presence of an inactive barnase locus. This result is important since it indicates that the phenotypical differences were not due to epigenetic effects (that may cause uncontrollable variations in transgene expression and therefore would limit the applicability of the system).

13) Proof of Site-Specific Recombination at the Stably Integrated Prolocus

Wheat lines carrying *Streptomyces* phage PhiC31 integrase were used to induce irreversible site-specific recombination reactions at the stably integrated T-DNA-loci pICH27371 according to the scheme in FIG. 10). The identification of suitable double haploid integrase wheat lines was performed with a transient test assay and is described in Rubtsova et al. (2008) Plant Cell Rep. 27: 1821-1831 The arrangement of the att sequences allows two alternative recombination reactions that may lead to the deletion of either the 3'- or the 5'-part of the T-DNA-locus.

Exposure of the prolocus to a second T-DNA encoding a *Streptomyces* PhiC31 integrase as a result of sexual hybridization led to a derivatization of the target-T-DNA at a high frequency. In total, 30 wheat transformants carrying independent target-T-DNA integrations displayed intrachromosomal recombination, as been proven by PCR-analyses and product sequencing (FIGS. 11,12). The recombination products could be recovered in subsequent generations; thus an inheritable "genetic switch" was induced by the PhiC31 Integrase in trans. The results demonstrate the feasibility of the att-integrase as a site specific recombination system for the establishment of the hybrid breeding system in wheat.

The invention claimed is:

1. A method of producing a male sterile monocotyledonous plant, comprising the steps of:
   a) introducing into a monocotyledonous plant, or plant cell, a first expression cassette comprising the following elements in 5' to 3' orientation:
      a tapetum-specific promoter functional in cells of a monocotyledonous plant;
      operatively linked thereto, a nucleic acid sequence coding for an N-terminal part of a protein which provides for male sterility;
      a nucleic acid sequence coding for the N-terminal part of a first intein; and
      optionally, operatively linked thereto, a terminator sequence functional in plant cells; and
   b) introducing into said plant or plant cell a second expression cassette comprising the following elements in 5' to 3' orientation:
      a tapetum-specific promoter functional in cells of a monocotyledonous plant;
      operatively linked thereto, a nucleic acid sequence coding for a C-terminal part of said first intein;
      a nucleic acid sequence coding for at least one copy of a flexible linker sequence;
      a nucleic acid sequence coding for a C-terminal part of said protein which provides for male sterility; and
      optionally, operatively linked thereto, a terminator sequence functional in plant cells.

2. The method according to claim 1, wherein the protein which provides for male sterility is an RNase, preferably barnase.

3. The method according to claim 2, wherein the nucleic acid sequence coding for the N-terminal part of the barnase is SEQ ID No. 3 or 13, or a functional fragment thereof, and wherein the nucleic acid sequence coding for the C-terminal part of the barnase is SEQ ID No. 5 or 27, or a functional fragment thereof.

4. The method according to claim 1, wherein the flexible linker sequence essentially consists of glycine and serine residues, preferably is GGGGS.

* * * * *